US012262885B2

United States Patent
Qi et al.

(10) Patent No.: US 12,262,885 B2
(45) Date of Patent: Apr. 1, 2025

(54) SOFT ANCHORING TISSUE REPAIR ASSEMBLY AND SYSTEM

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Zenan Qi, Attleboro, MA (US); Marc Joseph Balboa, Hopkinton, MA (US); Timothy Young, Natick, MA (US); Geoffrey Ian Karasic, Raynham, MA (US); Paul Alexander Torrie, Marblehead, MA (US); Kyle Steven Frederick Turner, Mansfield, MA (US); Nehal Navinbhai Patel, Boston, MA (US); Benjamin Michael Hall, Roslindale, MA (US); Kangqiao Li, Providence, RI (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 660 days.

(21) Appl. No.: 17/617,718

(22) PCT Filed: Jun. 12, 2020

(86) PCT No.: PCT/US2020/037574
§ 371 (c)(1),
(2) Date: Dec. 9, 2021

(87) PCT Pub. No.: WO2020/252372
PCT Pub. Date: Dec. 17, 2020

(65) Prior Publication Data
US 2022/0240918 A1 Aug. 4, 2022

Related U.S. Application Data

(60) Provisional application No. 62/891,553, filed on Aug. 26, 2019, provisional application No. 62/861,389, filed on Jun. 14, 2019.

(51) Int. Cl.
*A61B 17/04* (2006.01)
*A61B 17/06* (2006.01)

(52) U.S. Cl.
CPC ...... *A61B 17/0401* (2013.01); *A61B 17/0482* (2013.01); *A61B 17/06166* (2013.01);
(Continued)

(58) Field of Classification Search
CPC ............ A61B 17/0401; A61B 17/0482; A61B 17/06166; A61B 2017/0414;
(Continued)

(56) References Cited

U.S. PATENT DOCUMENTS

2012/0004669 A1 1/2012 Overes et al.
2013/0123810 A1* 5/2013 Brown .................. A61B 17/04
606/144
(Continued)

FOREIGN PATENT DOCUMENTS

EP 2 430 984 3/2012
WO WO17160589 A1 9/2017
(Continued)

OTHER PUBLICATIONS

European Application Examination Report dated Jan. 21, 2022.
Search Report and WO for PCT/US2020/037574 dated Dec. 1, 2020, 20 pages.

*Primary Examiner* — Tan-Uyen T Ho
*Assistant Examiner* — Bridget E. Rabaglia
(74) *Attorney, Agent, or Firm* — Norman F. Hainer, Jr.; Kate Ryland Tetzlaff

(57) ABSTRACT

A tissue repair assembly is disclosed, including a soft anchor body and at least a first suture operably coupled to the
(Continued)

anchor body. Tensioning on first and/or second ends of first suture may deploy the anchor body to a second configuration, in which the anchor body is axially compressed and radially extended. The tissue repair assembly may also include a means to cinch around a portion of a first and/or second suture and knotlessly lock the tissue repair assembly. Some embodiments may include a pre-formed knot. In some embodiments, the preformed knot may be a nail knot, provided wrapped around an insertion instrument and configured to receive and cinch around a suture extending therethrough.

20 Claims, 37 Drawing Sheets

(52) U.S. Cl.
CPC ............... *A61B 2017/0414* (2013.01); *A61B 2017/0446* (2013.01); *A61B 2017/0464* (2013.01); *A61B 2017/0474* (2013.01); *A61B 2017/0475* (2013.01); *A61B 2017/0496* (2013.01); *A61B 2017/06185* (2013.01)

(58) Field of Classification Search
CPC .... A61B 2017/0446; A61B 2017/0464; A61B 2017/0474; A61B 2017/0475; A61B 2017/0496; A61B 2017/06185; A61B 17/0485; A61B 2017/0406; A61B 2017/0409; A61B 2017/0424; A61B 17/0642; A61F 2002/0852
USPC .................................................. 606/233, 232
See application file for complete search history.

(56) References Cited

U.S. PATENT DOCUMENTS

| | | |
|---|---|---|
| 2013/0296934 A1 | 11/2013 | Sengun |
| 2014/0052178 A1 | 2/2014 | Dooney, Jr. |
| 2014/0052179 A1 | 2/2014 | Dreyfuss et al. |
| 2014/0277133 A1 | 9/2014 | Foerster |
| 2015/0173739 A1* | 6/2015 | Rodriguez ......... A61B 17/0401 606/232 |
| 2015/0201929 A1 | 7/2015 | Dooney, Jr. et al. |
| 2019/0015092 A1 | 1/2019 | Bosworth |

FOREIGN PATENT DOCUMENTS

| | | |
|---|---|---|
| WO | 018085663 | 5/2018 |
| WO | WO18085663 A1 | 5/2018 |

* cited by examiner

SOFT ANCHORING TISSUE REPAIR ASSEMBLY AND SYSTEM

CROSS-REFERENCE TO RELATED APPLICATIONS

This application is a 371 U.S National Stage Application of PCT App No. PCT/US2020/037574 filed Jun. 12, 2020 and titled "SOFT ANCHORING TISSUE REPAIR ASSEMBLY AND SYSTEM", which claims priority to U.S. Provisional App. No. 62/861,389 filed Jun. 14, 2019 and U.S. Provisional App. No. 62/891,553 filed Aug. 26, 2019, both titled SOFT ANCHORING TISSUE REPAIR ASSEMBLY AND SYSTEM, herein incorporated by reference in its entirety.

This application also incorporates by reference commonly owned U.S. Pat. No. 10,182,806 and commonly owned U.S Application 2019/0247039 and commonly owned U.S Application 2018/0228484; herein incorporated by reference in its entirety.

BACKGROUND

Many orthopedic surgeries involve the use of anchoring devices in procedures for attaching soft tissue to bone. Such procedures include attaching tendons to bone, bone to bone, tendons to tendons, and ligaments to bone, as well as ligament reconstruction. Most of these procedures rely on the use of polymeric, metal, or biodegradable rigid anchors with suture attached. The suture is passed through the tissue and a knot secures the construct together. However, the use of these anchors often requires rigid, hard materials to be placed in bone. If the anchors ever loosen, a surgeon or surgical technician is faced with the problem of having a potentially hard device migrate into a patient's joint, placing the patient at risk for arthritis. Accordingly, an anchor that uses only soft materials may pose less risk of anatomical damage in a joint or body cavity, should they be dislodged post-operatively.

Many existing soft flexible anchors available today anchor with tissue by deforming to a radially expanded state, and are locked in this state by tying knots. Since knot-tying may often be difficult, require a higher level of expertise, be time consuming, and/or be more anatomically disruptive to surrounding structures. There is a need for an improved system providing a means for securing the anchor in the deployed or anchored state without the need to tie a knot. There is also a need for an improved system for coupling tissue to the anchor without the need to tie a knot.

Definitions

Described herein are tissue repair systems, which use a soft anchor or soft anchor body construct. The tissue repair systems of this disclosure provide a large locking force, fixing the soft anchor within bone, and have the ability to constrict or lock sutures such as repair sutures with the anchor construct. The sutures may number a single strand or multiple sutures strands. Suture may include suture tape, flattened suture, suture of varying denier or any flexible member that is configured to repair tissue. Tissue repair systems of this disclosure may fixate a single suture passed through labral tissue, or alternatively, laterally fixate multiple repair sutures originating from a medial row during a rotator cuff repair. Locking the suture and suture-anchor constructs disclosed herein may rely on extending the sutures through and along tortuous paths through the system and/or soft anchor. Additionally, locking the suture and suture-anchor constructs may rely on increased friction and/or reducing lumen/opening sizes between a) sutures disposed within internal lumens of other sutures; 2) sutures, anchors and tissue surfaces; and 3) sutures and the braided walls of the soft body anchors. Additionally, a knotless repair may include a knot provided already formed and integrated with the system that may be selectively slid or altered to selectively lock the anchor construct. Some embodiments may include or make use of a suture with a hollow core section located between the free ends of the suture, the hollow core section providing a longitudinal passage in the suture. Some embodiments include a first, a second and sometimes a third suture, generally termed according to their designated task, for example repair suture, expansion suture, locking suture; these sutures formed during manufacturing as separate sutures but within the surgical constructs may be coupled together. Some of the sutures may extend through the longitudinal passage either in the same suture or a separate suture to form a self-locking adjustable suture construct as described herein. Longitudinal passage may be selectively elongated, by applying tension to the longitudinal passage to cinch around a suture disposed along the longitudinal passage, thereby locking a portion of the adjustable suture construct.

"Soft Anchor" is intended to mean a flexible and/or deformable anchor that is readily deformed via a tensioning member that is operatively coupled through a portion of the soft anchor. Soft anchor is not precluded from included some rigid portions; but is substantially formed from a flexible soft material such as suture or suture tape. In some embodiments, the soft anchor is formed entirely of braided suture. Soft anchor deforms to a deployed configuration that changes the soft anchor to a laterally or radially expanded configuration and may also include a longitudinal contraction.

"Deploy" or "deployed configuration" is intended to mean to change the shape of the body of the soft anchor (the "anchor body") such that the anchor body laterally expands to secure it within a hole in a bone or tissue (whereby securing the suture anchor to the bone). Shown in many figures throughout this disclosure, the deployed anchor is shown with a lateral dimension that is smaller than the bone tunnel. This is for ease of viewing the suture paths. In reality, these deployed anchors wedge into and may embed within the bone tunnel softer bone tissue. Stated otherwise the deployed maximum lateral dimension of the anchor is at least as big as the tunnel lateral dimension.

"Lock" or "locked configuration" with respect to the repair suture is intended to mean either locking the repair suture to the anchor body such that the suture may no longer slide along the anchor body and the tissue coupled to the repair suture is secured in place. With respect to the anchor body itself, a locked configuration is intended to mean locking the anchor body in a deployed configuration to inhibit the anchor body from relaxing and moving out of the deployed configuration.

"Expansion Suture" or "tension suture" is intended to mean the suture(s) that upon tension on this suture deploys the anchor body. In some embodiments, this may also directly or indirectly lock the repair suture to the anchor body.

"Repair Suture" is the suture passed through the target soft tissue and used to affix the target tissue to bone;

"Knotless system" is defined as a system wherein a knot is not required to be formed by the user or instrument to place the system or assembly in a locked configuration. A knotless system may include a preformed or pre-tied knot as provided.

SUMMARY

Examples of the tissue repair system of this disclosure may include one or more of the following, in any suitable combination. In examples, the tissue repair system of this disclosure may include a soft anchor body that may be tubular, having a lumen extending therethough, a proximal end, a distal end, and a longitudinal axis extending therebetween. The system may also include an expansion suture coupled to the anchor body such that first and second ends of the expansion suture exit the anchor body adjacent to the proximal end of the anchor body and may form a pre-tied knot, defining an expansion suture first loop length. The pre-tied knot may be associated with a separate suture and not the expansion suture. Expansion suture may be interwoven repeatedly though and along the soft anchor body and in-between fibers or threads of the soft anchor body. Tensioning of the first and second ends of the expansion suture may cause the anchor body to change from a first configuration, in which the anchor body is elongate, to a second configuration, in which the anchor body is axially compressed and radially extended. The elongate configuration may be a first elongate configuration such that the soft anchor body fits within an insertion tube, or a second more relaxed elongate configuration in which the soft anchor body fits within a bone tunnel. In the second configuration, the soft anchor body may at least partially embed with walls of a bone tunnel. Tensioning at least of the first and second ends of the expansion suture may cause the pre-tied knot to slide towards the anchor body to reduce the expansion suture loop length to a second shorter loop length, and may embed the pre-tied knot within the soft anchor body and tighten the pre-tied knot. Alternatively, the pre-tied knot may be pushed along the suture. This secures the soft anchor body in the second configuration.

The expansion suture may also have a longitudinal passage portion (and thereby a non-longitudinal passage portion), the longitudinal passage portion having a first configuration configured to receive and allow sliding of a first and second end of a repair suture therethough and wherein tension on the first and second expansion suture ends elongates the longitudinal passage portion and radially shrinks the longitudinal passage portion to a second configuration, that shrinks around repair suture to inhibit sliding of the repair suture therethough. The tissue repair system may alternatively include a locking suture coupled to the anchor body such that first and second ends of the locking suture exit the anchor body adjacent to the proximal end of the anchor body. Locking suture may be an independently controllable suture. The locking suture may have a longitudinal passage portion with a first configuration configured to receive and allow sliding of a first and second end of a repair suture therethough and wherein tension on the first and second locking suture ends elongates the longitudinal passage portion to a second configuration, that inhibits sliding of the first and second end of the repair suture. The locking suture allows for limited independent repair suture securement before the expansion suture is engaged to deploy the soft anchor body to the second configuration. The longitudinal passage portion may extends orthogonally to a longitudinal axis of the anchor body and across an outer surface of the anchor body. The longitudinal passage portion may extends orthogonally to a longitudinal axis of the anchor body across an outer surface of the anchor body distal end. The expansion suture may extends along a first side wall of the anchor body from the proximal end to the distal end, cross the distal end, and returns along a second side wall opposite the first sidewall from the distal end to the proximal end. The expansion suture may include one or two loops, each loop extending through the anchor body from the proximal end to the distal end, crossing the distal end, and returning along a second sidewall opposite the first sidewall from the distal end to the proximal end.

In further examples, the tissue repair system of this disclosure includes a tissue repair assembly including a soft anchor body having a proximal end, a distal end, and a longitudinal axis extending therebetween. The assembly also includes an expansion suture coupled to the anchor body such that first and second ends of the suture exit the anchor body adjacent to the proximal end of the anchor body. Tensioning of the first and second ends of the expansion suture cause the anchor body to change from a first configuration, in which the anchor body is elongate, to a second configuration, in which the anchor body is axially compressed and radially extended so as to anchor the assembly with a bone tunnel.

The expansion suture may also having a longitudinal passage portion, having a first configuration configured to receive and allow sliding of a first and second end of a repair suture therethough and wherein tension on the first and second expansion suture end elongates the longitudinal passage portion to a second configuration, configured to inhibit sliding of the first and second end of the repair suture. The assembly may include an additional suture, termed the locking suture, coupled to the anchor body. First and second ends of the locking suture may exit the anchor body adjacent to the proximal end of the anchor body and form a pre-tied knot. Tensioning of the first and/or second ends of the locking suture may move the pre-tied knot towards and into the proximal end of the soft anchor body and secures the anchor body in the second configuration. Alternatively or additionally pre-tied knot may be pushed. Longitudinal passage portions may extend orthogonally to a longitudinal axis of the anchor body across an outer surface of the anchor body.

In further examples, the tissue repair system of this disclosure includes a soft anchor body having a proximal end, a distal end, and a longitudinal axis extending therebetween. The system also includes a first suture extending through the soft anchor body such that first and second ends of the suture exit the anchor body adjacent to the proximal end of the anchor body, the first suture further comprising a longitudinal passage length oriented across the anchor body. The longitudinal passage length is defined by a first and second opening into an internal passageway in the suture, and both openings may be disposed at either the proximal or the distal end of the anchor body. Tensioning at least one of the ends of the first suture causes the anchor body to change from a first configuration, in which the anchor body is elongate, to a second configuration, in which the anchor body is axially compressed and radially extended. Tension at least one of the ends of the first suture may also causes the longitudinal passage length to elongate and thereby secure a second suture extending through the longitudinal passage length.

The first and second ends may be coupled via a pre-tied knot, defining a first loop length, the pre-tied knot proximally disposed relative to the anchor body. Tension on the first or second ends of the first suture may slide the pre-tied knot towards the anchor body and secure the first and second suture in a second smaller loop length configuration.

Examples of a method of tissue repair of this disclosure include: coupling a repair suture through a portion of soft tissue, the repair suture may define two free ends; snaring the two free ends through a longitudinal passage length of a second suture, the second suture interwoven through a soft anchor body so that a first and second end of the second suture extend from a proximal end of the soft anchor body; drawing the two free ends through the longitudinal passage length so as to draw the soft tissue closer to the soft anchor body; inserting the longitudinal passage length and soft anchor body into a bone tunnel adjacent the soft tissue; tensioning the first and second ends of the second suture so as to elongate the longitudinal passage length and lock the first suture in place and thereby the soft tissue; tensioning the first and second ends of the second suture to deploy the soft anchor body in to an anchoring configuration; and once the soft tissue is in the desired location, sliding a pre-tied knot associated with both first and second ends of the second suture towards the soft anchor body and away from the soft tissue so as to lock the second suture and thereby the soft anchor body in a locked configuration.

Further examples of a method of tissue repair of this disclosure include coupling a repair suture through a portion of soft tissue, the repair suture defining two free ends; snaring the two free ends through a longitudinal passage length of a second suture, the second suture interwoven through a soft anchor body so that a first and second end of the second suture extend from a proximal end of the soft anchor body; drawing the two free ends through the longitudinal passage length so as to draw the soft tissue closer to the soft anchor body; inserting the longitudinal passage length and the soft anchor body into a bone tunnel adjacent the soft tissue; tensioning the first and second ends of the second suture so as to elongate the longitudinal passage length and lock the first suture in place and thereby the soft tissue; tensioning the first and second ends of a third suture so as to deploy the soft anchor body to an anchoring configuration, the third suture interwoven through the soft anchor body so that a first and second end of the third suture extend from a proximal end of the soft anchor body; and once the soft tissue is in the desired location, sliding a pre-tied knot of the third suture towards the soft anchor body and away from the soft tissue so as to lock the soft anchor body in a locked configuration.

Further examples of the method of this disclosure include forming the bone hole in bone. In examples, tensioning the first and second ends of the suture includes tensioning the first and second ends of the suture by hand. In other examples, tensioning the first and second ends of the suture includes tensioning the first and second ends of the suture with a specialized delivery device. These and other features and advantages will be apparent from a reading of the following detailed description and a review of the associated drawings. It is to be understood that both the foregoing general description and the following detailed description are explanatory only and are not restrictive of aspects as claimed.

In further examples, the tissue repair system of this disclosure includes a surgical construct including a soft anchor body with a longitudinal axis, a first end and a second end and a tensionable construct. The tensionable construct may be a flexible strand that extends through at least a portion of the soft anchor body and along the longitudinal axis of the body, the flexible strand having a lumen. The system may also include a first shuttling device disposed through a portion of the flexible strand lumen, the shuttling device configured to draw a first end of the flexible strand into, through and out of the lumen to form a first loop. The system may also include a second shuttling device disposed through the portion of the flexible strand lumen, to draw a second end of the flexible strand into, through and out of the lumen to cross over the first closed loop and form a second loop.

In further examples, the tissue repair system for coupling a tissue with a bone hole is disclosed. Tissue repair system includes an anchor defining a proximal end, a distal end, and a longitudinal axis extending between the proximal and distal ends. Tissue repair system also includes a suture construct extending through the anchor and including a first and a second loop, both loops extend through a lumen of the suture construct so as to cross over each other within the lumen and emerge at opposite ends to each other; the lumen defining a friction zone configured to selectively knotlessly secure the suture construct with the anchor.

In further examples, the tissue repair system is disclosed including a tubular, soft anchor body having a proximal end, a distal end, and a longitudinal axis extending therebetween. The system also includes a first suture construct extending through the soft anchor body comprising a longitudinal passage length portion, the entire longitudinal passage portion disposed along an outer surface of the tubular soft anchor body. The longitudinal passage portion may receive a first and a second end of the first suture construct to form two loops, each loop crossing over each other within the longitudinal passage portion and emerging at opposite ends of the longitudinal passage portion to each other. The longitudinal passage portion is also configured to selectively elongate and knotlessly secure the suture construct with the anchor body upon tensioning at least one of the ends of the suture construct. Tensioning at least one end of the suture construct also causes the anchor body to change from a first configuration, in which the anchor body is elongate, to a second configuration, in which the anchor body is axially compressed and radially extended. The first of the two loops may extend though the soft anchor body, and a second of the two loops may extend along an outer surface of the soft anchor body. A first of the two loops may extend though the soft anchor body, and a second of the two loops is configured to couple to tissue. The first loop may be configured such that tension on the first loop causes the anchor body to change from a first configuration, in which the anchor body is elongate, to a second configuration, in which the anchor body is axially compressed and radially extended and wherein the second loop may be configured to couple to tissue such that tension on the second loop causes the tissue to approximate the soft anchor body. The tissue repair assembly may also include a second suture construct, extending through the anchor body and tensioning at least one of end of the second suture construct causes the anchor body to change from a first configuration, in which the anchor body is elongate, to a second configuration, in which the anchor body is axially compressed and radially extended. The longitudinal passage portion may be at a proximal end of the soft anchor body. The longitudinal passage portion may be disposed along a side wall—of the soft anchor body. The longitudinal passage portion may be at a distal end of the soft anchor body.

In further examples, the tissue repair system is disclosed including a tubular, soft anchor body having a proximal end, a distal end, and a longitudinal axis extending therebetween. The system also includes a first suture extending through the soft anchor body, the first suture having a first and second end extending from the proximal end of the soft anchor body and an intermediate portion disposed therebetween, the intermediate portion forming a slipknot including one or more loops. First and second ends of the first suture extend through at least one loop of the slipknot. Tensioning at least one of the ends of the suture end causes the anchor body to change from a first configuration, in which the anchor body is elongate, to a second configuration, in which the anchor body is axially compressed and radially extended. Tensioning at least one of the suture ends of the first suture also causes the slipknot to cinch around the first and second ends and thereby secure the anchor body in the second configuration. The system may also include a second suture, formed separately from the first suture. At least one of the loops of the slipknot is further configured to receive an end of the second suture therethrough. Tensioning at least one of the ends of the first suture may also cause the slipknot to cinch around the second suture and thereby secure the second suture to the anchor body. The one or more loops may include a first loop and a second loop and wherein the first end of the first suture extends through the first loop and the second end of the first suture extends through the second loop and not the first. Tensioning on both ends of the first suture may cause the first loop to cinch around the first end and the second loop to cinch around the second end (and not the first end) and thereby secure the anchor body in the second configuration. The first loop and the second loops may be separated by a length of suture therebetween that extends from one side of the anchor, across the midline to the other side of the anchor. This length of suture may be coupled with the soft anchor body. The slipknot maybe disposed external to the anchor and at a proximal end thereof.

A method of repairing tissue is also disclosed including coupling a repair suture to a portion of soft tissue, the repair suture having at least one free end. The at least one free end may then be snared through at least one loop of a slip knot formed in a tensioning suture construct, the tensioning suture construct formed from a suture formed separately from the repair suture. Tensioning suture construct may be interwoven through a soft anchor body. A slipknot is formed by a portion of the tensioning suture construct between first and second ends of the tensioning suture construct. The first and second ends of the tensioning suture construct may extend from the slipknot, through the soft anchor body followed by through at least one of the plurality of loops. The at least one free end of the repair suture is drawn through the slipknot to draw the soft tissue closer to the soft anchor body. The first and second ends of the tensioning suture construct are then pulled or tensioned to deploy the soft anchor body to an anchoring configuration that is radially expanded and axially shorted. Tensioning the first and second ends of the tensioning suture construct also cinches the slipknot around the first and second ends of the tensioning suture construct and repair suture, and thereby secures the soft tissue with the soft anchor body and the soft anchor body in the anchoring configuration. The at least one loop of the slip knot may comprise a first loop and a second loop, and wherein the first end of the tensioning suture extends through the first loop and not the second loop and the second end of the tensioning suture extends through the second loop and not the first loop. Tensioning the first and second ends of the tensioning suture construct may cause the first loop to cinch around the first end and the second loop to cinch around the second end and not the first end and thereby secure the anchor body in the second configuration.

A further example embodiment of a tissue repair assembly is disclosed, including a soft anchor having a proximal end, a distal end, and a longitudinal axis extending therebetween. The assembly also includes a first suture extending woven through and along the longitudinal axis of soft anchor body, the first suture defining a first and second end extending from the proximal end of the soft anchor. The assembly also includes a second suture formed separately from the first suture, coupled to the soft anchor and formed in a nail knot comprising a plurality of loops and a first suture tail. The plurality of loops is configured to receive the first and second ends of the first suture extending from the proximal end of the soft anchor and also a third suture operatively coupled to repair tissue. The third suture is also formed separately from the first and second suture. Tensioning at least one of the ends of the first suture causes the anchor body to change from a first configuration, in which the anchor body is elongate, to a second configuration, in which the anchor body is axially compressed and radially extended. Tensioning the first suture tail of the second suture causes the nail knot to cinch around the first and second ends and also cinch around the third suture, and thereby secure the soft anchor in the second configuration and secure the repair tissue to the soft anchor. Cinching around the third suture may include cinching around at least limb of the third suture, and in some embodiments two limbs of the third suture.

A further example of a tissue repair system includes an insertion instrument comprising a tube, a soft anchor operatively coupled to the insertion instrument, the soft anchor having a proximal end, a distal end, and a longitudinal axis extending therebetween. The system also includes a first suture extending through the soft anchor body, the first suture defining a first and second end extending from the proximal end of the soft anchor and through the tube. The system also includes a second suture coupled to the soft anchor and wrapped around an outer circumferential surface of the tube to form a nail knot construct having a plurality of loops and a first suture tail extending through a first elongate slot of the tube and along an inner lumen of the tube, the second suture formed separately from the first suture. The first and second end of the first suture extend from the proximal end of the soft anchor and through the plurality of loops. The tube is configured to place the soft anchor into a bone hole. The first suture tail is operatively coupled to the soft anchor. The tube may optionally comprise a second elongate slot, circumferentially spaced from the first elongate slot. The second suture further comprises a second suture tail extending through the second elongate slot and along an inner lumen of the tube. The first elongate slot may be longer than that the second elongate slot. The first elongate slot may extend up to a proximal end of nail knot. The first elongate slot may be further configured to receive a suture snare to draw a repair suture operatively coupled to tissue through the slot and through the nail knot.

A method of tissue repair may include coupling a repair suture to a portion of soft tissue, the repair suture defining at least one free end. The at least one free end maybe drawn through a plurality of loops of a nail knot, the nail knot at least partially wrapped around a tube of an anchor insertion instrument. The at least one free end may be further drawn through the nail knot so as to draw the soft tissue closer to a soft anchor body disposed within the anchor insertion instrument. The soft anchor may then be inserted into a prepared bone hole. The soft anchor may then be deployed. The nail knot may then be pushed off or removed from the insertion instrument and a first end of the nail knot tensioned to cinch the nail knot around the at least one free end and thereby secure the soft tissue with the soft anchor.

BRIEF DESCRIPTION OF THE DRAWINGS

The disclosure will be more fully understood by reference to the detailed description, in conjunction with the following figures, wherein.

DETAILED DESCRIPTION

Figure 1A:
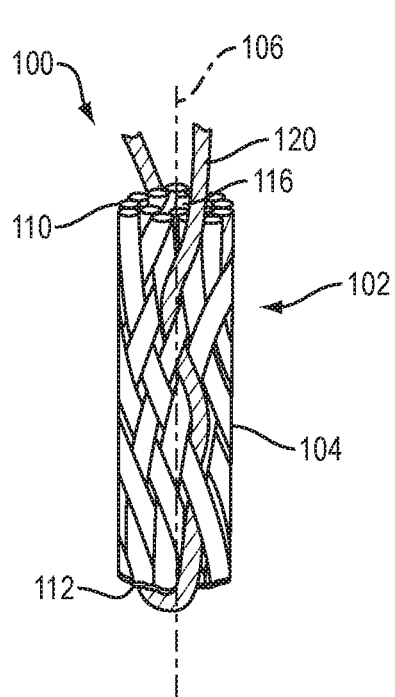
FIGS. 1A-C illustrate a prior art tissue repair system using a soft anchor.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

Comprise, include, and/or plural forms of each are open-ended and include the listed parts and can include additional parts that are not listed. And/or is open-ended and includes one or more of the listed parts and combinations of the listed parts.

Referring now to FIG. 1A, an exemplary tissue repair assembly 100 known in the art is shown. Generally described, tissue repair assembly 100 comprises a soft anchor 102 (also can be called an anchoring implant) and a tension/expansion suture 120 that is operatively coupled to the soft anchor 102. The soft anchor 102 has a three-dimensional, tubular shaped body 104 extending along a longitudinal axis 106. The anchor body 104 includes a proximal end 110, which may be open and in communication with an internal or resident volume 116, and a distal end 112, which may be open or closed. In the example of FIG. 1A, the expansion suture 120 passes through the wall of the soft anchor body 104 to the outside for a short distance before it passes back between fibers of the soft anchor body 104 to the inside of the soft anchor body 104, and possibly into the internal volume 116, then out again by passing between the fibers or braids and around the distal end 112 of the soft anchor body 104 before repeating the penetrations and exiting back out around the proximal end 110 of the soft anchor body 104. In other examples, not shown, the suture 120 may extend along the interior or the exterior of the soft anchor body 104 without penetrating the walls of the soft anchor body 104. Notably, as provided, the suture 120 is not locked into place with respect to the soft anchor body 104, but rather remains slideable through or along the walls of the soft anchor body 104.

The soft anchor 102 may lock the expansion suture 120 within bone or other hard tissue (not shown here) and allow for the further attachment of soft tissue to the expansion suture 120. Preferably, the soft anchor 102 is loaded into a dedicated delivery system 115, which may include an inserter tube 108 and soft anchor pusher 114 and deployed into the hard tissue to facilitate a repair. Non-limiting examples of such specialized delivery systems 115 are generally described in U.S. Publication No. 2013/0123810 (Brown et al.), commonly owned and incorporated by reference herein. In other examples, not shown, the soft anchor 102 may be deployed as a retaining anchor for two pieces of soft tissue.

Examples of the soft anchor 102 may be formed from a soft, flexible construct of braided yarns or fibers that has been rolled into a tube or cone shape. Typical materials that would be used to construct the soft anchor 102 may be, but are not restricted to, ultra-high molecular weight polyethylene (UHMWPE), polyester, polypropylene, silk or bio absorbable materials typically used for suturing applications. A rolled structure may be held together with adhesive or stitches and the free edge of the braided material may be bound further in similar methods. Alternatively, the structure may be braided suture or yarn and cut/sealed with a heat knife. Other non-limiting examples of soft anchor 102 include the Q-Fix soft anchoring implant, manufactured by Smith and Nephew and generally described in U.S. Publication No. 2013/0123810 (Brown et al.), incorporated by reference herein. Other non-limiting examples may include non-tubular constructs that are a flexible tape with the expansion suture back and forth therethrough.

Figure 1B:
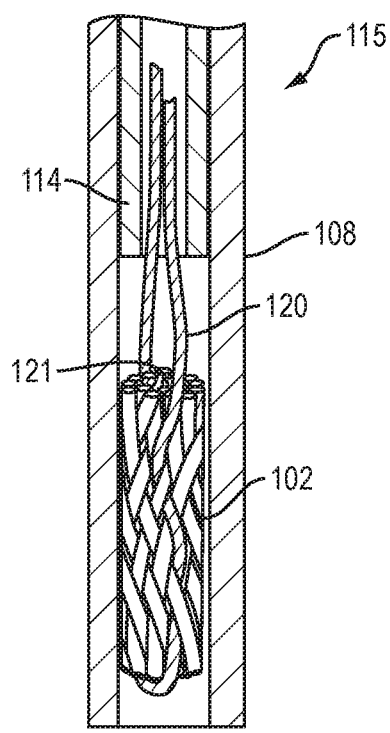
Figure 1C:
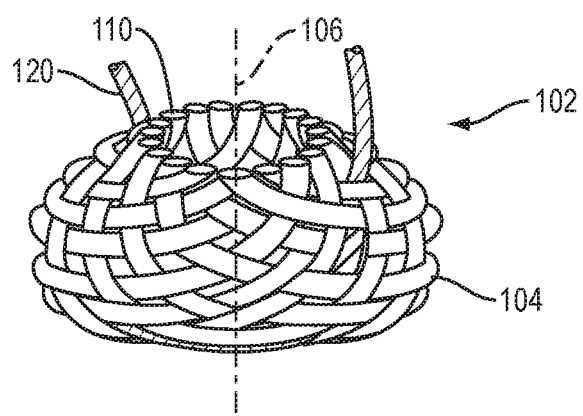

Continuing with the example soft anchor shown in FIGS. 1A-1B, in the predeployed state, the fibers of the soft anchor body 104 are relaxed in an orientation neither substantially parallel with the longitudinal axis 106 nor orthogonal to the longitudinal axis 106 of the soft anchor body 104. Turning now to FIG. 1C, when the expansion suture 120 is tensioned; the soft anchor body 104 shortens along its longitudinal axis 106 and, in doing so, expands radially. This radial expansion forces the soft anchor body 104 to assume a larger effective diameter than it had prior to deployment, which may be larger than the hole into which it was inserted. In the case of bone, the anchor 102 is typically placed beyond the cortical bone and into the cancellous bone portion, which is soft such that anchor deployment radially expands the anchor into the cancellous bone and may deform the cancellous bone somewhat. In this deployed state, the fibers of the soft anchor body 104 are more aligned in an orientation parallel to the longitudinal axis 106 and are generally more compacted. Thus, the anchoring aspect of the soft anchor 102 is achieved.

Generally, the exemplary soft anchoring implant 102 is in the form of a three dimensional structure either like that of a sock with a closed end tube or an open ended tube, or a combination of both. This three-dimensional structure preferably defines or includes a predefined inner space or resident volume 116. The "resident volume" is a volume that is intentionally formed by the three-dimensional anchoring implant structure in its manufactured, predeployed or relaxed state. A resident volume as defined herein may be inherently thicker and/or wider than the thickness of the material from which the structure is fabricated. For example, a flat piece of braided material with a hole in it may not define a resident volume (the hole), because the hole is only as deep as the thickness of the braided material. It is not necessarily a permanently open or enclosed volume. For example, as in the case of soft flexible braided materials, said resident volume 116 may exist upon manufacture and inherently in the structure, but when the sides of the structure are compressed, the resident volume 116 may become smaller or disappear altogether. The resident volume 116 may exist as manufactured in the structure of the soft anchor body 104 when the soft anchor resides in an upright configuration but tend to disappear when the structure is on its side due to the forces of gravity on the soft, flexible braided material of the structure. However, the resident volume 116 always exists within the structure when the structure is returned to its original position and configuration. The term as it is used herein does not necessarily preclude the resident volume 116 from being filled with some other substance at a given time nor does it preclude the structure folding or collapsing in on itself to temporarily obscure the presence of the resident volume. The biaxial braided material of the soft anchoring soft anchor can be configured to define a resident volume when in a relaxed state, a substantially reduced resident volume when loaded into an insertion device, and substantially no resident volume when fully deployed to tissue. Further discussion of the resident volume is generally described in U.S. Publication No. 2013/0123810 (Brown et al.), incorporated by reference herein.

The discussion will now turn to FIGS. 2A-2D, illustrating a tissue repair system and a method of use. Shown is a distal end portion of a tissue repair system 200, which may generally include a tissue repair assembly 201, insertion instrument 210 and may include a snare tool 240. Insertion instrument 210 may include an outer tube 202 and inner tube 204, slideably disposed along the outer tube 202. Insertion instrument 210 may be similar to that generally described in U.S. Publication No. 2013/0123810 (Brown et al.), and U.S. Publication 2019/0247039 (Gregoire et al), both commonly assigned and herein incorporated by reference herein. The tissue repair assembly 201 may include a soft anchor 220 and expansion suture 230 similar to the tissue repair assembly 100 of FIGS. 1A-C, except as described below. A portion of the expansion suture 230 may include a longitudinal passage portion 232, which may be provided dilated, configured to receive a repair suture therethrough (described later). Expansion suture 230 may define a lumen along its entire length (hollow core) and therefore in some embodiments, longitudinal passage 232 is formed simply by the presence of a snare tool (described later) or length of suture that extends into, along and out of a portion of the expansion suture lumen. In other embodiments, a portion of the expansion suture is provided with a preformed longitudinal passage tunnel that may hold this tunnel form with or without a snare tool or second suture present.

As shown, tissue repair system 200 may also include a snaring tool 240 that may draw a repair suture through longitudinal passage 232. Snaring tool 240 may be provided already extended through the longitudinal passage 232, or may be provided separately. In alternative embodiments, no snaring tool may be provided. Snaring tool 240 generally may include a loop at one end to receive ends of the repair suture 250 and may extend through longitudinal portion 232 and then route proximally through a portion of insertion instrument 210 (not shown). Snare handle 242 may be incorporated with other portions of a handle portion of insertion instrument 210 for example (not shown). In other embodiments, snaring tool 240 may be a loop of suture where a bight of this suture may form a snaring suture loop to capture the repair suture 250. The snaring suture ends may extend through the longitudinal passage 232, configured to grasp and draw the repair suture through the longitudinal passage 232.

Expansion suture 230 includes two ends 234 and 236 that may come together to form a sliding knot 238 at a proximal side of soft anchor 220, defining an expansion suture loop length that extends through and around the soft anchor 220 and knot 238. Preferably, the sliding knot 238 is one that allows the expansion-suture loop length to decrease. Knot may move towards the soft anchor 220. Sliding knots may be configured to reduce the suture loop length while the longitudinal passage 232 remains stationary. Alternatively, some knot embodiments may slide while applying a unilateral tension to one side of the longitudinal passage 232 to draw the longitudinal passage 232 to one side of the anchor 220. During radial expansion of the anchor 220, the anchor distal end tends to move proximally, and potentially reduces tension on the repair suture 250. Drawing longitudinal passage 232 away from soft tissue 252 while sliding the knot 238 may therefore counteract some of the slack that may develop during anchor deployment. Example sliding knots may include a tautline hitch knot, Duncan loop, Roeder Knot.

Figure 2A:
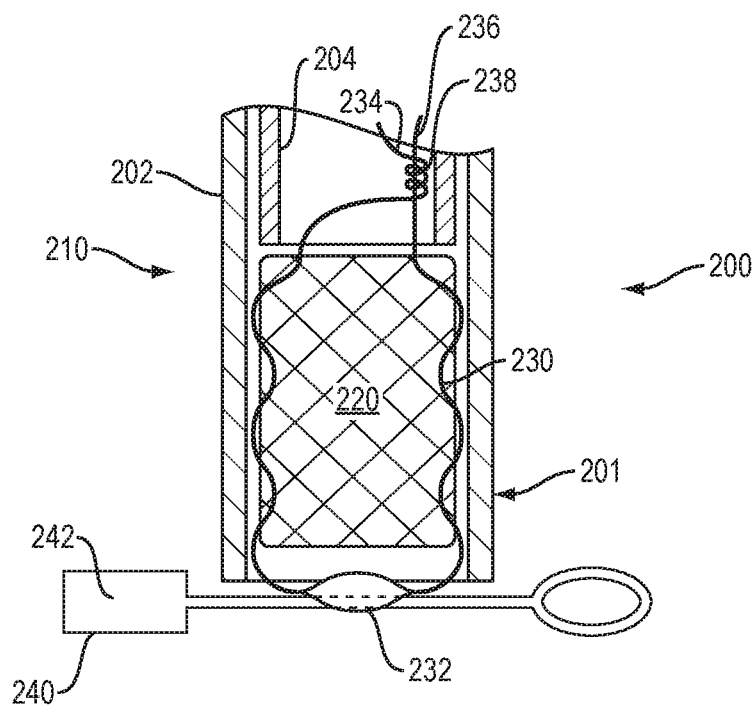
FIGS. 2A-2D illustrate a first example of a tissue repair system of this disclosure with a longitudinal passage portion.
Figure 2B:
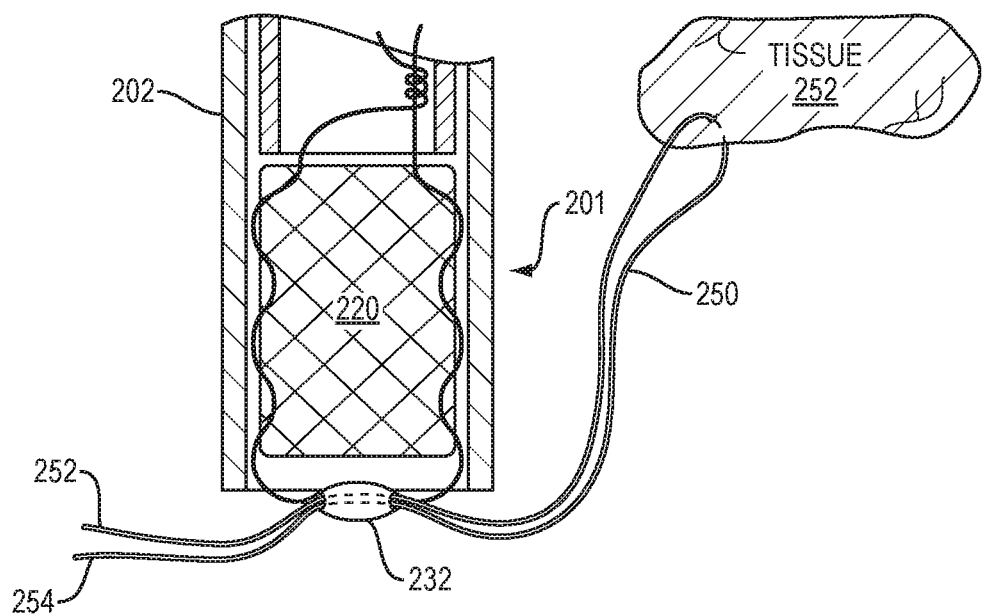
Figure 2C:
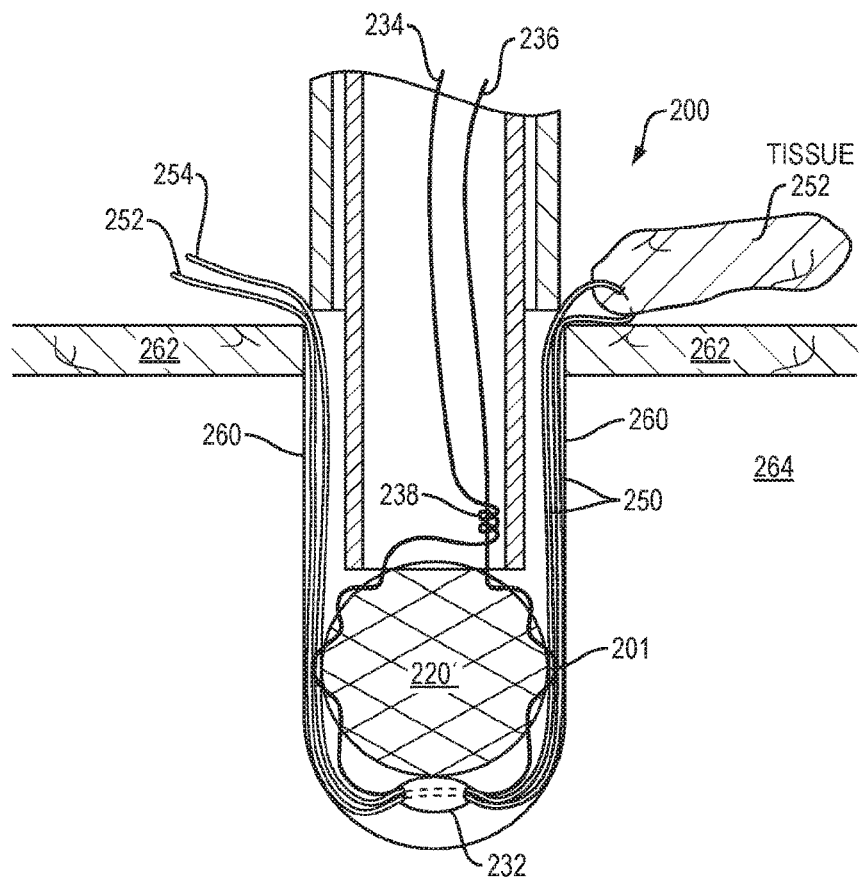
Figure 2D:
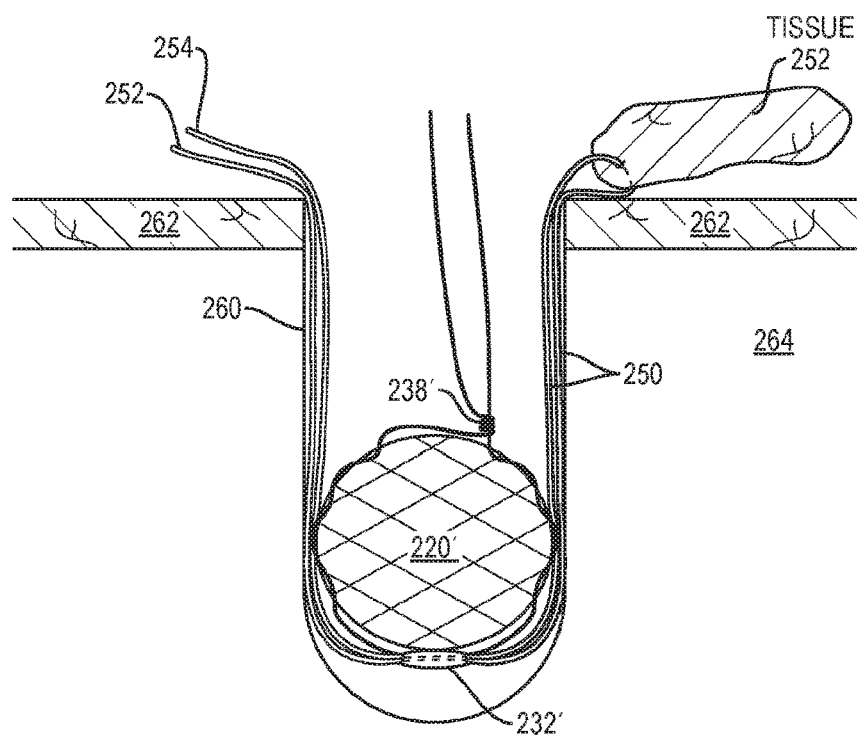

Shown in FIG. 2B a repair suture 250 may be selectively coupled to tissue 252 and then drawn or threaded through longitudinal passage 232. Repair suture 250 may be a similar length of flexible material to expansion suture, or may be different in braid, material and dimensions. For example repair suture may include a braided core, as opposed to the expansion suture which preferably includes a hollow core to form the longitudinal passage 232. The repair suture 250 is configured to couple with tissue 252 and slide through longitudinal passage 232. Once tension on the longitudinal passage 232 has caused the longitudinal passage 232 to cinch around repair suture 250, repair suture 250 is preferably knotlessly secured within longitudinal passage 232 and thereby knotlessly secured with anchor 220. A higher coefficient of friction along an outer surface of repair suture 250 or within the longitudinal passage 232 of the expansion suture 230 may help with knotless securement. In this configuration seen in FIG. 2A and FIG. 2B the soft anchor 220 is mostly contained in the insertion tube 202 and therefore is in an elongate configuration. Some minimal or partial deployment may be necessary to expose the longitudinal passage 232; however, the soft anchor 220 is still in an elongate configuration. Longitudinal passage 232 may be provided in a radially expanded (dilated) configuration to receive a snare tool or two ends of a repair suture 250 and longitudinal passage 232 may extend across a distal end of soft anchor and orthogonal to the soft anchor longitudinal axis. In some embodiments, longitudinal passage 232 may be a length of expansion suture lumen that is operable to better grip or secure a suture extending therethrough. For example, longitudinal passage 232 may be braided so as to preferable reduce to a smaller lumen diameter than other portions of the expansion suture 230, which may be smaller than the suture extending therethrough. In another example, longitudinal passage 232 may include an inner lumen surface defined by the braided wall that has a higher coefficient of friction. This may be in the form of an additional element threaded through the longitudinal passage 232, the additional element having a higher coefficient of friction, or an additional coating added to the internal surface. The additional element may include a series of angled barbs that are oriented to allow the repair suture 250 to slide in a first direction and inhibit retraction. Longitudinal passage 232 may extend across a substantial portion of the soft anchor width or diameter. Longitudinal passage 232 includes an entrance opening and exit opening, both openings in this embodiment at the distal end of anchor 220. A longer longitudinal passage 232 generally increases friction between the longitudinal passage and suture that extends therethrough. Longitudinal passage 232 may therefore be approximately equivalent to a diameter of the soft anchor 220, or potentially longer to bend around and extend along the sides of soft anchor for example. Friction may also however be increased by increasing tension on the longitudinal passage 232, and potentially in this embodiment how tight the pre-tied knot 238 is cinched down. Therefore, the inventors envision a series of combinations of tension on the expansion suture and length of longitudinal passage 232, whereby the longer the longitudinal passage 232, the less tension may be required on the longitudinal passage in order to secure the system in a locked configuration. Longitudinal passage 232 may vary from 1-8 mm, and may preferable between 2-3 mm. The repair suture 250 may be USP #1, OD 0.4-0.499 mm or USP #2, OD 0.5-0.599 mm. The outer diameter of the portion of expansion suture 230 not including the longitudinal passage may be USP #2, 0.5-0.599 mm Both ends (252 and 254) of repair suture 250 may be drawn through longitudinal passage 232 and proximally along an external surface of insertion instrument 210 or through an internal portion of insertion instrument 210, by a snare tool for example. FIG. 2C shows the tissue repair assembly 200 in a partially deployed configuration, having been pushed out of insertion tube 202 (or insertion tube having been retracted). Tissue 252 has been approximated to bone by drawing two repair suture ends 252 and 254 further through longitudinal passage 232. At least one of the expansion suture ends 234 and/or 236 has been withdrawn proximally so as to alter the configuration of the soft anchor to a radially expand state 220', configured to engage the walls of the tunnel 260 and wedge the tissue repair assembly 201 within the pre-formed tunnel 260, similar to configuration shown in FIG. 1C. Of note longitudinal passage, 232 may still be radially expanded. Repair suture 250 may extend along an outer surface portion of soft anchor 220. Therefore, it may be at least partially locked in position between the expanded soft anchor 220' and tunnel wall. Tissue 252 may therefore be at least partially locked in position in this partially deployed configuration. FIG. 2D shows a fully deployed configuration, wherein in addition to the soft anchor 220' being radially expanded, further tension on the expansion suture 230 may elongate longitudinal passage 232' and cinch around repair suture 250 further locking the tissue 252 in place. Finally, slipknot 238' may be slid distally and tightened securing expansion suture 230. Slip knot 238' may be first slid to reduce the expansion suture loop length so that the knot 238' may abut or at least partially embed within a proximal end of soft anchor 220'. It is preferable that slipknot 238' is positioned in its final configuration within the bone tunnel and not protruding or external from the tunnel entrance. A knot protruding from or on the bone outer cortical surface 262 may irritate local tissues. In addition, expansion suture loop length may be reduced such that longitudinal passage 232' may also abut and may be at least partially drawn into a portion of the soft anchor 220. Slipknot 238' may then be locked to prevent loosening of the assembly. Expansion suture ends 234 and 236 may be operably coupled to a control in insertion instrument handle (not shown) that may be operable to control knot translation along the expansion suture 230 and the selective knot tightening to lock the assembly in a locked configuration. As such, FIG. 2D shows a locked configuration in the form of an assembly bundle or ball including soft anchor in deployed form 220', expansion suture loop at a minimum loop length, knot 238' and longitudinal passage 232' both abutting and preferably at least partially amalgamated or wedged into a portion of the soft anchor. The knot 238' or longitudinal passage 232' may be partially disposed within lumen of the soft anchor 220' or between anchor fibers for example. Slipknot 238' is configured to tighten and limit relative motion between the two expansion suture ends 234 and 236. At least one of the sutures (repair suture 250 or expansion suture 230) may be form with a high coefficient of friction material. Expansion suture 230 may have a high coefficient of friction than repair suture. Higher coefficient of friction suture can be PE or PE coated to UHMWPE.

Figure 3A:
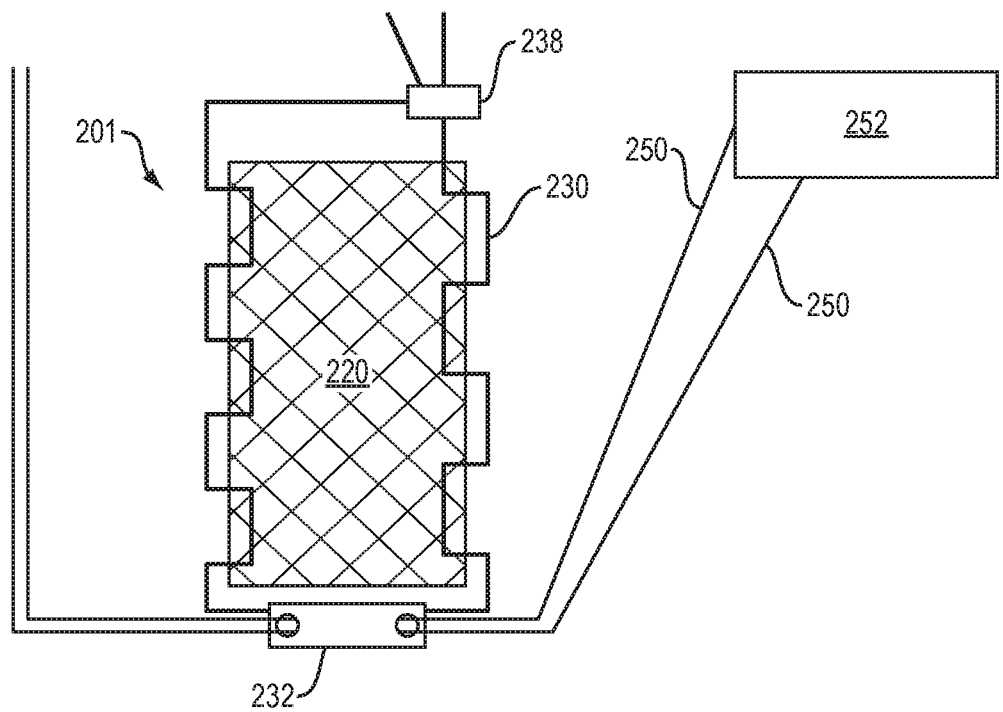
FIGS. 3A and 3B schematically show the tissue repair system of FIGS. 2A-2D including an expansion suture and repair suture in an un-deployed configuration and deployed configuration respectively, in accordance with this disclosure.
Figure 3B:
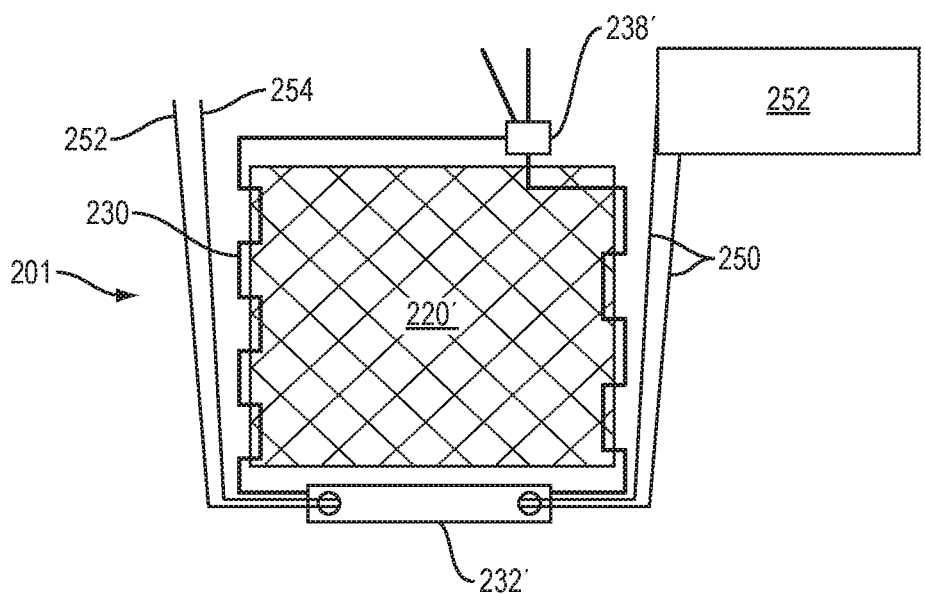
Figure 4:
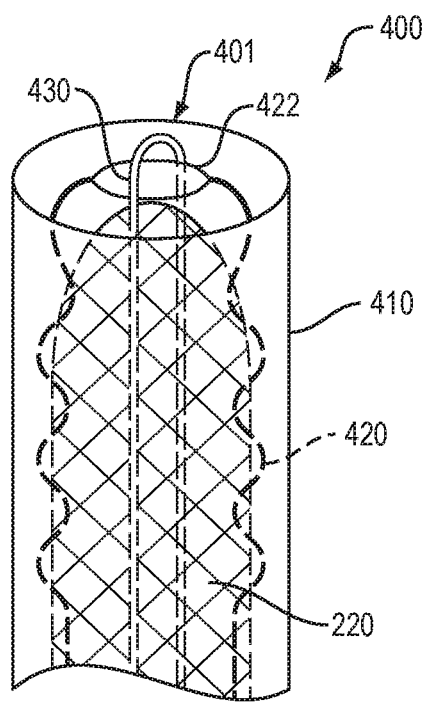
FIG. 4 illustrates another embodiment of a tissue repair assembly, in accordance with this disclosure.
Figure 5:
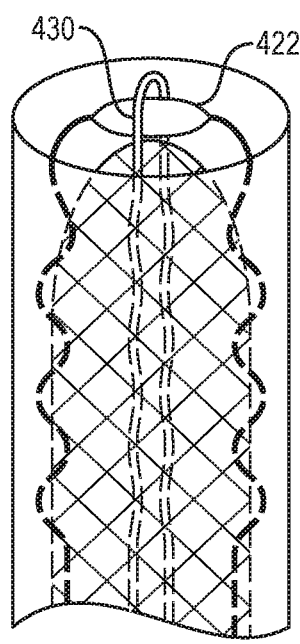
FIG. 5 illustrates a different view of a tissue repair assembly, in accordance with this disclosure.

FIGS. 3A and 3B schematically shows the suture routing of tissue repair assembly 201. Although not drawn to scale, the relative sizes are intended to be representative of the configuration changes. Tissue repair assembly 201 may include soft anchor 220 in a first elongate state in FIG. 3A when disposed within the insertion tube, or a relaxed state when released into bone tunnel. In FIG. 3A, longitudinal passage 232 of expansion suture 230 is in a radially expanded configuration to receive a repair suture 250 therethrough and allow repair suture 250 to slide therethrough and approximate tissue 252. Knot 238 is in a loose, slipping configuration. Expansion-suture loop is in a loose longer length configuration; with minimal tension such that soft anchor 220 is in a relaxed or elongate state. Full deployment of tissue repair assembly 201 is shown in FIG. 3B wherein the soft anchor 220' is in a deployed radially expanded configuration, soft tissue 252 is approximated to the bone tissue, the longitudinal passage 232 is in an elongate and radially reduced configuration 232' so as to frictionally secure repair suture 250 and inhibit repair suture 250 from sliding. Slipknot 238' has been moved towards the soft anchor 220' to reduce the expansion-suture loop length and knot 238' has been tightened to prevent loosening of expansion suture 230 and thereby lock assembly in anchored and locked configuration.

Figure 6:
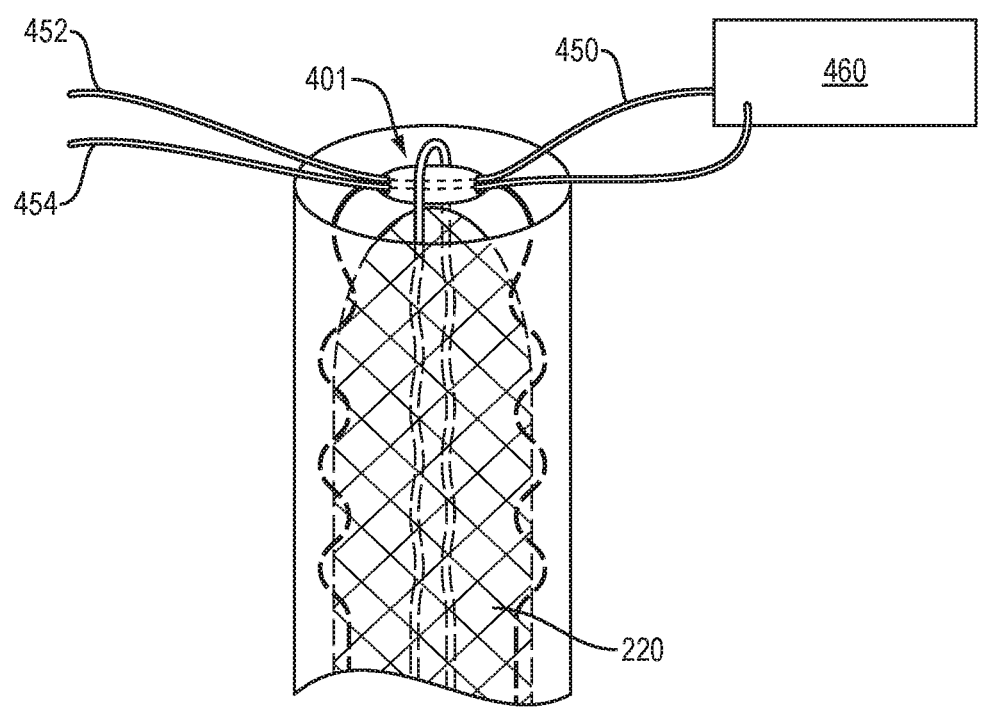
FIG. 6 illustrates the embodiment as shown in the FIGS. 4 and 5 with a repair suture threaded through a longitudinal passage portion, in accordance with this disclosure.
Figure 7A:
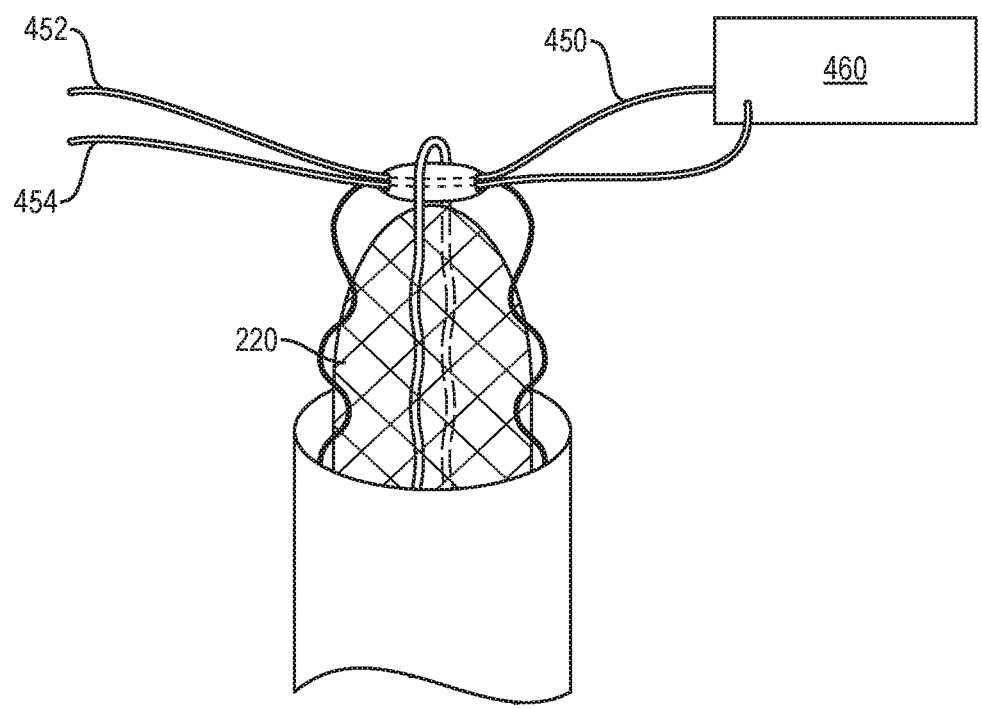
FIGS. 7A and 7B show successive stages of deployment of a tissue repair assembly, in accordance with this disclosure.
Figure 7B:
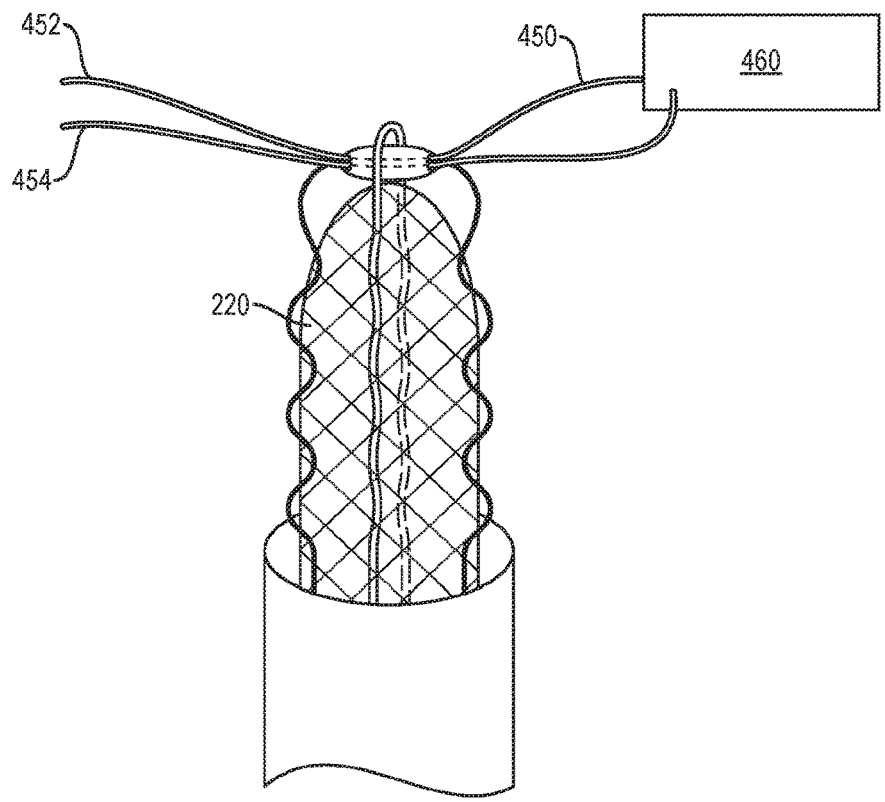
Figure 8A:
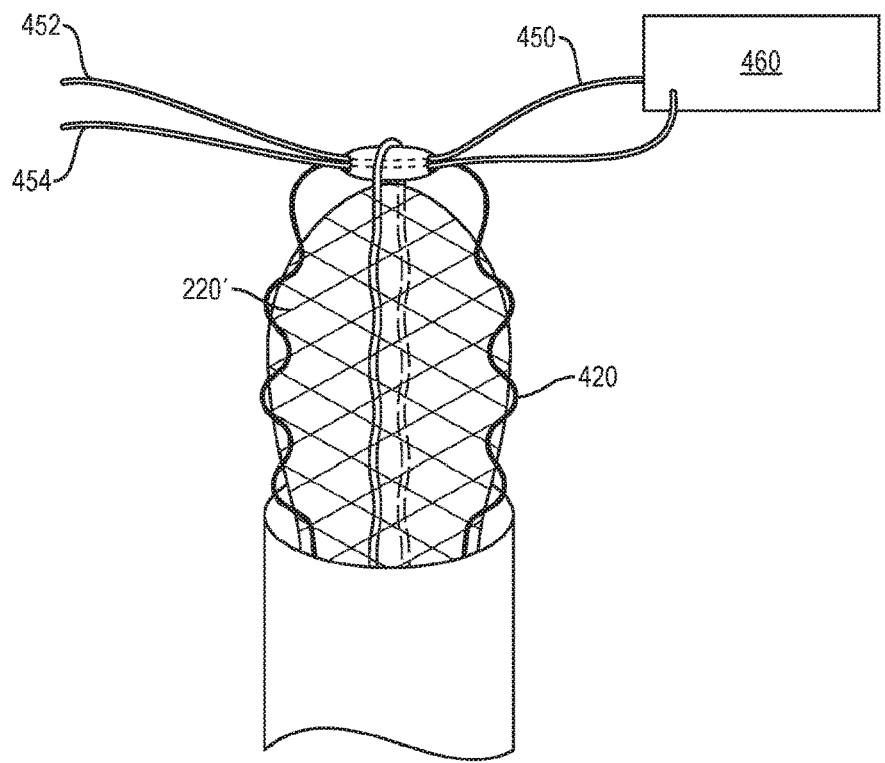
FIG. 8A illustrates a partial expansion of a soft anchor of a tissue repair assembly, in accordance with this disclosure.
Figure 8B:
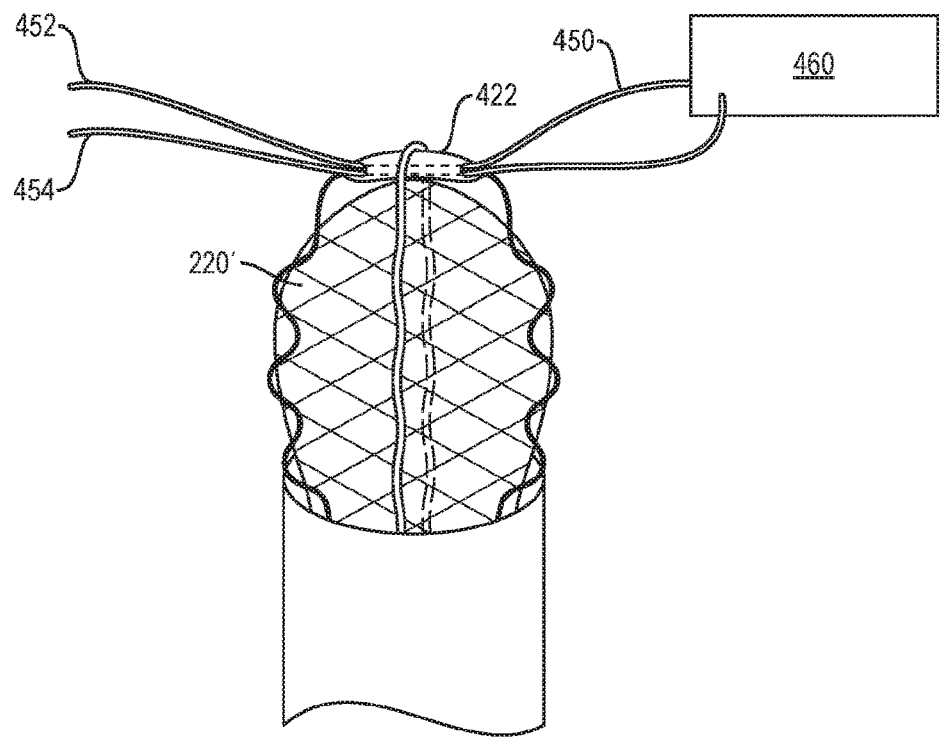
FIGS. 8B and 8C illustrates a full expansion of soft anchor of a tissue repair assembly, with a repair suture knotlessly cinched to soft anchor, in accordance with this disclosure.
Figure 8C:
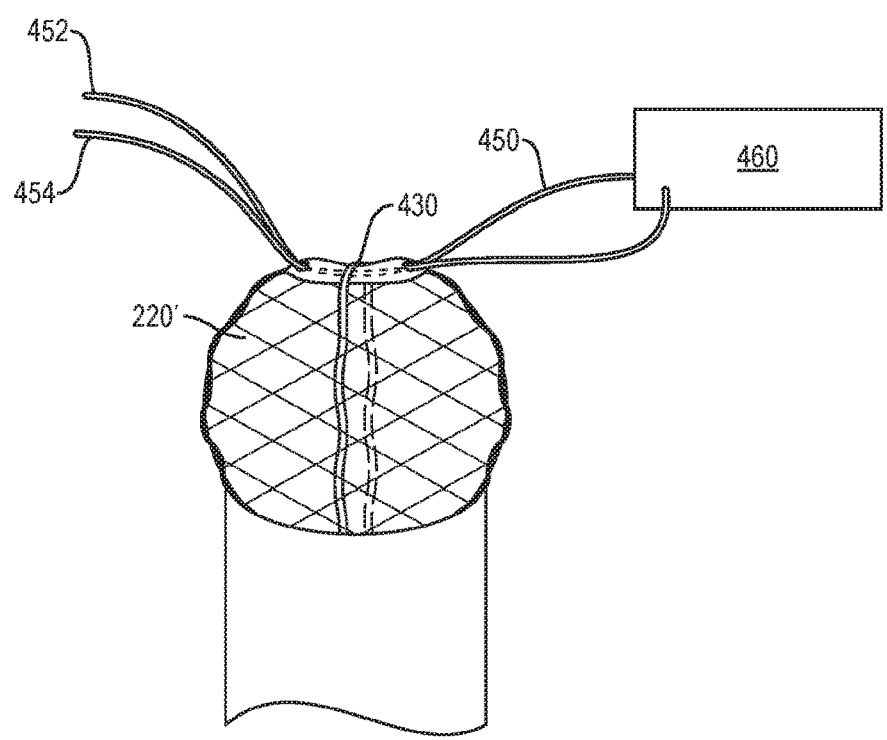

Another example of a tissue repair system 400 of this disclosure is shown in FIG. 4-8C. The tissue repair system 400 is similar to the tissue repair system 200, except that the expansion suture may not include a pre-tied knot; a separate suture, independently controlled extends through the soft anchor and may include the pre-tied knot. This provides a system therefore that may be independently deployed before a final knotless locking suture is employed. Expansion suture includes a longitudinal passage. This may further increase reliability of the locked assembly. Shown in FIG. 4, a tissue repair system 400 may include a soft tissue repair assembly 401 and insertion instrument 410. Assembly 401 may include soft anchor 220, expansion suture 420 and locking suture 430. As described in previous embodiments, a snare tool may also be provided. Expansion suture 420 and locking suture 430 may include MAGNUMWIRE◊, an ultra-high strength braided polyethylene suture available in multiple colors to facilitate suture management. Locking suture 430 may loop over a distal-most end of expansion suture 420, best seen in FIG. 5. Expansion suture 420 may include a longitudinal passage 422 in the form of a Chinese finger trap type of construct. Locking suture 430 may loop over the longitudinal passage 422. Similar to the previous embodiment, repair suture may be drawn or passed between threads of the expansion suture 420 and along the lumen of longitudinal passage 422 construct. FIG. 6 show a view of the repair suture 450 threaded through longitudinal passage 422, two repair suture ends 452 and 454 extending therefrom. Repair suture 450 has been threaded through tissue 460 and tension on the repair suture 450 may adjust the soft tissue 460 position relative to the anchor 220. FIGS. 7A and 7B shown partial and full release of soft anchor 220 from the inserter tube respectively; in FIG. 7A the anchor 220 is in the elongate state (partially within the inserter tube) and in FIG. 7B the anchor is moved to a relaxed state (released from inserter tube). The soft anchor 220 is typically inserted into a pre-formed bone tunnel. Tension on the expansion suture 420 may then begin to radially expand soft anchor 220' as shown in FIGS. 8A and 8B, showing progressive expansion. In FIG. 8B, tension on the expansion suture has mostly deployed anchor 220', longitudinal passage portion 422 is radially reduced to secure the repair suture 450. At this point, tension on the locking suture 430 further secures repair suture by compressing or crimping the longitudinal passage portion 422 and drawing longitudinal passage portion 422 and expansion suture 430 into the distal end of deployed soft anchor 220'. Further tension on either or both the locking suture 430 or expansion suture 420 may draw repair suture 450 into a distal end of soft anchor 220' further inhibiting the assembly 401 from loosening, seen best in FIG. 8C. Locking suture 430 may include a knot similar to knot 238 (not shown) which may then be slid down the locking suture 430 and employed to further secure the assembly 401 in a locked configuration. In alternative configurations expansion suture 420 may include the knot 238 and the locking suture 430 may include the longitudinal passage.

Figure 9:
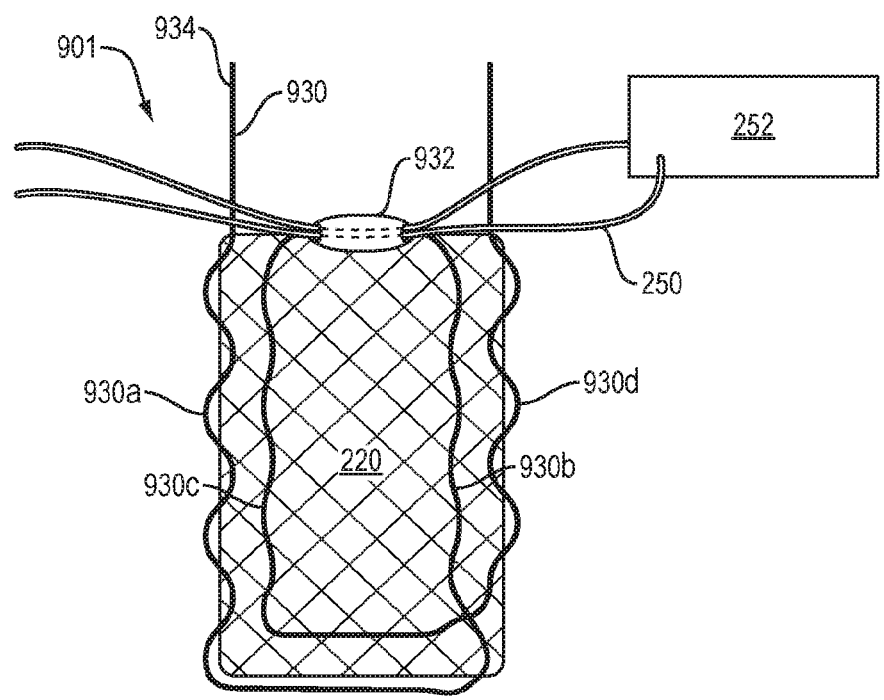
FIG. 9 illustrates an embodiment having an alternative expansion suture routing, in accordance with this disclosure.
Figure 10:
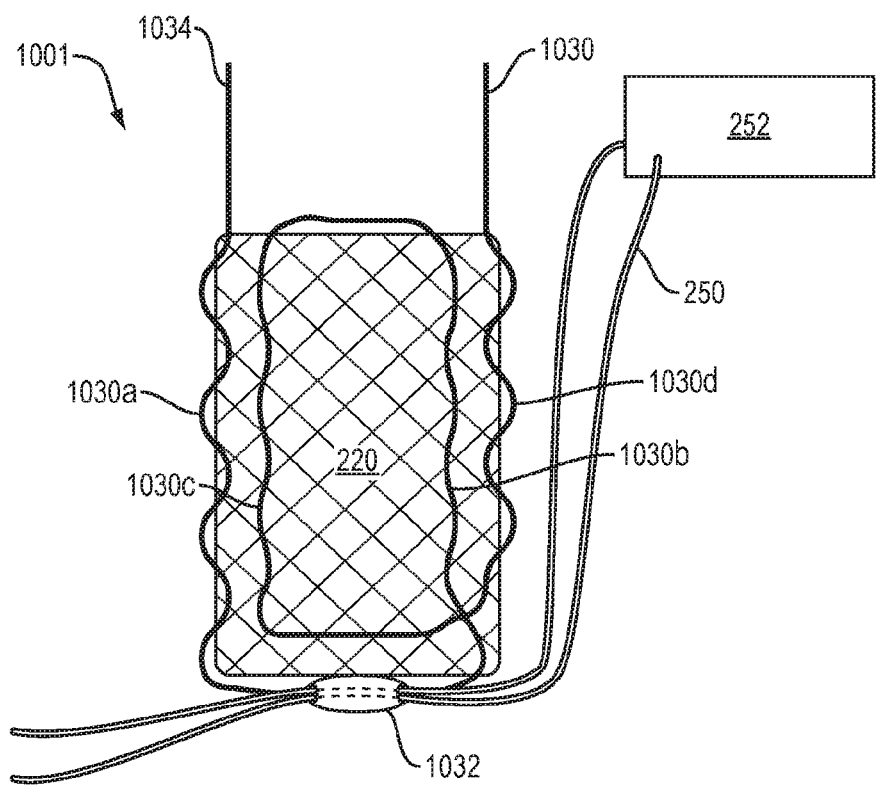
FIG. 10 illustrates an embodiment with a distally disposed longitudinal passage region location, in accordance with this disclosure.

FIG. 9 and FIG. 10 illustrate an assembly with an expansion suture 930 having a double loop, to increase the tortuous path of the expansion suture 930 through the anchor, such that friction between suture/bone and suture/anchor may be sufficient to lock repair suture 250 in place. This may potentially eliminate the need for a pre-tied knot to secure the configuration. FIG. 9 shows an alternative embodiment wherein the longitudinal passage portion 932 is at a proximal most end of the soft anchor 220. This embodiment is similar to previously described embodiments and includes a tissue repair assembly 901 including an soft anchor 220 and expansion suture 930 interwoven therethrough and a longitudinal passage portion 932. A knot may couple ends of expansion suture 920 (not shown in FIG. 9) defining an expansion-suture loop length. Expansion suture 930 may include a proximally disposed longitudinal passage 932 that lies approximately orthogonal to a longitudinal axis of the soft anchor 220 and across a proximal end of the soft anchor 220. In this case, an inserter instrument (not shown) may need an opening or slot that provides passage of a suture snaring means to draw repair suture 250 through the longitudinal passage portion 932 while the assembly 901 is at least partially disposed within the inserter tube. In this embodiment the repair suture 250 does not extend along a pre-formed bone tunnel as disclosed in previous embodiments and may allow easier adjustment of repair suture 250 and thereby location of the tissue 252. This may avoid slack in the repair suture 250. Two loops of expansion suture 930 may extend through soft anchor 220. Extending from first end 934, a first portion 930a may interweave through a first side of soft anchor 220 up to and including a distal-most end of soft anchor 220 and extend across a portion of the distal-most end diameter of soft anchor 220. Expansion suture 930 may then return proximally defining portion 930b, that extends between the distal-most end up to and including the proximal-most end and transition to form the longitudinal passage portion 932. Portion 930b may also interweave between threads of soft anchor 220, similar to that shown in FIGS. 1A-1C. Alternatively portion 930b may extend solely along an outer wall of suture anchor 220 and thereby not interweave with anchor 220. Portion 930c may extend from the opposing side of longitudinal passage portion 932 and between the proximal-most end of soft anchor 220 towards the distal end and preferably up to and including the distal end. Portion 930c may also interweave between threads of soft anchor 220, or along an internal lumen of anchor 220 or along an outer wall of suture anchor 220. Portion 930d may extend therefrom and interweave through a length of soft anchor 220 as shown. Between portion 930c and 930d, the expansion suture may extend across a portion of soft anchor diameter either within the soft anchor 220 or external to the soft anchor 220. FIG. 9 shows an embodiment with an expansion suture comprising two suture loops and a longitudinal passage 932 disposed between the first and second loops of the two loops.

FIG. 10 shows an alternative embodiment with an expansion suture comprising two suture loops and a longitudinal passage. This embodiment is similar to previously described embodiments with a tissue repair assembly 1001 including an soft anchor 220 and expansion suture 1030 interwoven therethrough, a longitudinal passage locking portion 1032 and a knot (not shown in FIG. 10) defining an expansion-suture loop length. Knot may couple both ends of expansion suture 1030 similar to the embodiment disclosed in FIG. 2A-2D for example. Expansion suture 1030 may include a distally disposed longitudinal passage portion 1032 that lies approximately orthogonal to a longitudinal axis of the soft anchor and across a proximal end of the soft anchor 220. Longitudinal passage portion 1032 is preferably external to the soft anchor 220. Two loops of expansion suture 1030 may extend through soft anchor 220. Extending from expansion suture first end 1034, a first portion 1030a may interweave through a first side of soft anchor 220 up to and including a distal-most end of soft anchor 220 and transition to form a first side of the longitudinal passage portion 1032. Portion 1030b may then extend from the other side of longitudinal passage portion 1032 from the distal-most end up to the proximal end of soft anchor. Portion 1030b may also interweave between threads of soft anchor 220, or may extend along an internal lumen or external sidewall and thereby not interweave with the soft anchor 220. Portion 1030c may extend from portion 1030b between the proximal end of soft anchor 220 to the distal end again and possibly up to and including the distal-most end, so as to extend across an outer surface of distal-most end of soft anchor. Portion 1030d may extend therefrom and interweave through a length of soft anchor as shown. Between portion 1030c and 1030d, the expansion suture may extend across a portion of soft anchor diameter either within the soft anchor 220 or external to the soft anchor 220. FIG. 10 generally discloses a double loop through the soft anchor, with at least a portion of the expansion suture 1030 interwoven through the anchor 220. Expansion suture 1030 also defines a longitudinal passage portion disposed at distal-most end of anchor 220.

When the tissue repair system is used in a bone anchoring scenario such as a rotator cuff repair or a labral repair, a hole or tunnel 260 may be drilled into the bone where the soft anchor assembly or tissue repair assembly such as assembly 201 or 401 described earlier is to be placed. This may be done using a standard orthopedic drill to a predetermined depth. The depth of the hole is typically about the same as or slightly longer than the length of the assembly 201 or 401. Before placing the tissue repair assembly 201 or 401 into the prepared bone hole, a repair suture 250 may be coupled to soft tissue 252 and then threaded through the longitudinal passage of a suture such as portion 232, 422, 932 or 1032 for example. This may be achieved with a preassembled snare, suture passer (not shown) that extends through the at least one longitudinal passage portion 232, 422, 932 or 1032. Repair suture 250 may then be drawn through the longitudinal passage to at least approximate tissue 252 to the desired location. As shown in FIG. 1B or 2A-2C, an inserter tube with assembly 201, 401, 901 or 1001 housed inside may be slid into or pushed into the drilled hole. A soft anchor pusher may also move with the inserter tube and remains close to or touching the proximal end of the soft anchor 220. Repair suture 250 may extend along an outer surface of inserter tube while anchor is recessed within the inserter tube, and may therefore may be radially separated from expansion suture during soft anchor insertion.

Assembly 201, 401, 901 or 1001 with repair suture extended though the longitudinal passage portion may be placed into the bone hole such that a longitudinal axis of soft anchor 220 is coaxial with bone tunnel longitudinal axis. This may be achieved by retracting the inserter tube such as tube 108 or 202 in an axial direction to reveal the soft anchor pusher 114 or 204, which remains adjacent the anchor proximal end. The soft anchor pusher 114 or 204 may be fixed relative to a first portion of the handle (not shown here), while the inserter tube 108 or 202 may be attached at its proximal end to a moveable block coupled to a knob, slide, or trigger (not shown here) housed on a handle which can be activated by the user. Once the inserter tube 108 or 202 has been retracted to the outermost level of the bone, the soft anchor is left inside the preformed hole, exposed to the bone as shown in FIG. 2C. Drawing or applying tension on the repair sutures 250 may approximate tissue 252 to bone 264 or fine-tune tissue location.

Once tissue 252 is adjacent bone tunnel 260, expansion suture may be tensioned, with the soft anchor pusher 114 or 204 remaining stationary within the bone space. The soft anchor pusher 114 or 204 ideally extends into the bone to the bottom of the cortical layer, typically 0.02" to 0.05" below the bone/tissue surface. As the expansion suture 230 is tensioned, the soft anchor 220 may retract upon itself with the end of the soft anchor pusher 114 or 204 providing counter traction and assumes a shorted, expanded state with an increased effective diameter. By "counter traction," we mean a backstop is provided resisting movement of the proximal end of the soft anchor proximally, thus causing the soft anchor to bunch and expand. As the suture 230 is tensioned, in some embodiments the longitudinal passage length 232 may elongate and may reduce in lumen diameter, and/or be pulled into a distal opening of the soft anchor 220, and/or be pulled up against a closed distal end of soft anchor 220 so as to lock the repair suture 250 relative to the soft anchor 220 and thereby the bone. In alternative embodiments, the longitudinal passage length is a portion of a separate locking suture that may be independently controlled (preferably before the soft anchor is moved to the expanded configuration).

Before tensioning expansion suture 230, repair suture free ends 252 and 254 may be drawn through the longitudinal passage to better place soft tissue closer to bone. In some embodiments, the option to tension a locking suture independently from the expansion suture may elongate the longitudinal passage length and secure the repair suture 250 and thereby the soft tissue 252 in place. Tensioning the expansion suture 230 may then deploy the soft anchor 220 and further lock the repair suture 250 and thereby the soft tissue 252 in place. In some embodiments tensioning the expansion suture 230 may simultaneously expand the soft anchor and elongate the longitudinal passage to lock the repair suture. In addition, the inventors also envision a partially deployed configuration with the anchor within the bone tunnel (not illustrated here) wherein the expansion suture 230 is pulled so to partially expand the soft anchor 220 radially, at which point ends of repair suture 254 and 252 may be further withdrawn to finely tune the position of the soft tissue 252 relative to the bone and soft anchor assembly 201, 401 etc. For example radially expanding and axially contracting the soft anchor 220 may naturally move the longitudinal passage length 232 in a proximal direction in the embodiment shown in FIG. 2A-2D for example, creating some slack in the repair suture 250 between the bone 264 and the tissue 250, which may be compensated for with this fine tuning in a partial deployed configuration. Therefore partial deployment is defined as a longitudinal passage length configuration sufficient to allow the repair suture 250 to slide there through, and a partial anchor deployment that also allows the repair suture 250 to slide and adjust tension along the repair suture 250 and thereby adjust location of the soft tissue 252.

Expansion suture ends may be coupled in a sliding knot defining an expansion suture closed or continuous loop having a first length. Once assembly has been moved to a deployed configuration with soft tissue in the desired location and the longitudinal passage length elongated to secure the repair suture in place, tension on at least one end of the expansion suture may slide the knot towards the soft anchor and reduce the expansion-suture loop length. Alternatively, a separate knot pushing device could be used to slide the pre-configured knot down.

Tension on both suture ends may tighten the knot to lock the expansion suture in a second minimum loop length configuration. Sliding knot may be at least partially embedded within the soft anchor. Sliding knot when locked may be directly adjacent the soft anchor and flush with or recessed within the entrance to the bone tunnel. Having a portion of the knot protrude from the bone tunnel may irritate local tissues post procedure.

Expansion is accomplished primarily by the orientation change of the fibers as discussed earlier. When the soft anchor 220 increases in diameter, the anchor becomes larger than the hole through which it was inserted in the cortical bone 262, thus resisting pull out. The soft anchor 220 also embeds itself to some degree into the cancellous bone 264 that makes up the majority of the walls of the bone tunnel 260. This is possible because in most cases, the cancellous bone 264 is significantly softer than the associated cortical bone layer 262 above it. This "embedding" of the soft anchor 220 into the cancellous bone may also contribute to resistance of the soft anchor to pull out. The assembly 201 or 401 is preferably placed into the bone in a lengthwise or axial orientation, such that one of the ends enters the bone first, with the opposite end entering last. Of note, repair sutures 250 that lie along the outer surface of soft anchor 220 will also be at least partially embedded into the bone as the anchor deploys, providing a supplemental repair suture lock means.

Sutures may also be tensioned by hand or with the use of some other tensioning mechanism. Tensioning sutures to a high force by hand can be difficult. Alternate mechanisms are described in U.S. Publication No. 2013/0123810 (Brown et al.), incorporated by reference herein.

Figure 11A:
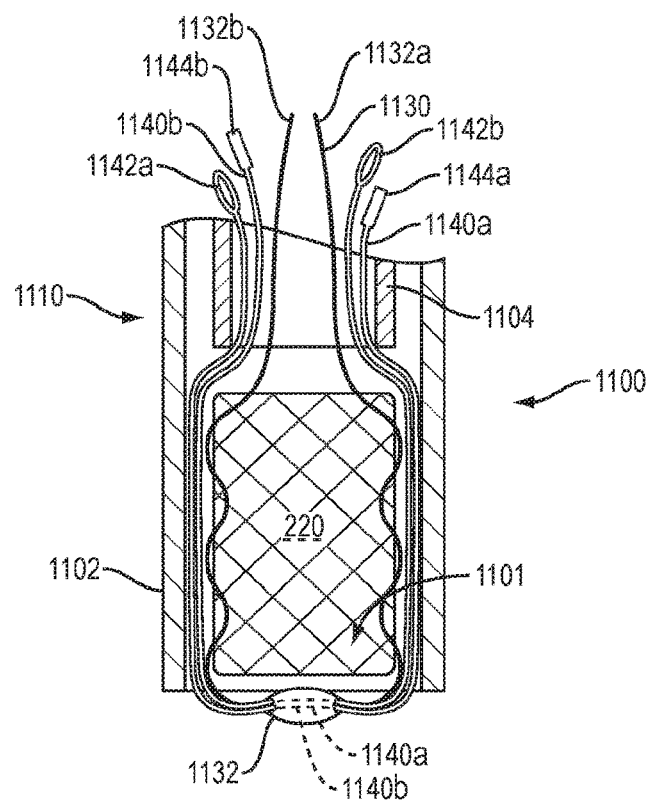
FIGS. 11A-11B illustrates an alternative embodiment of a tissue repair assembly before and after deployment respectively, in accordance with this disclosure.
Figure 11B:
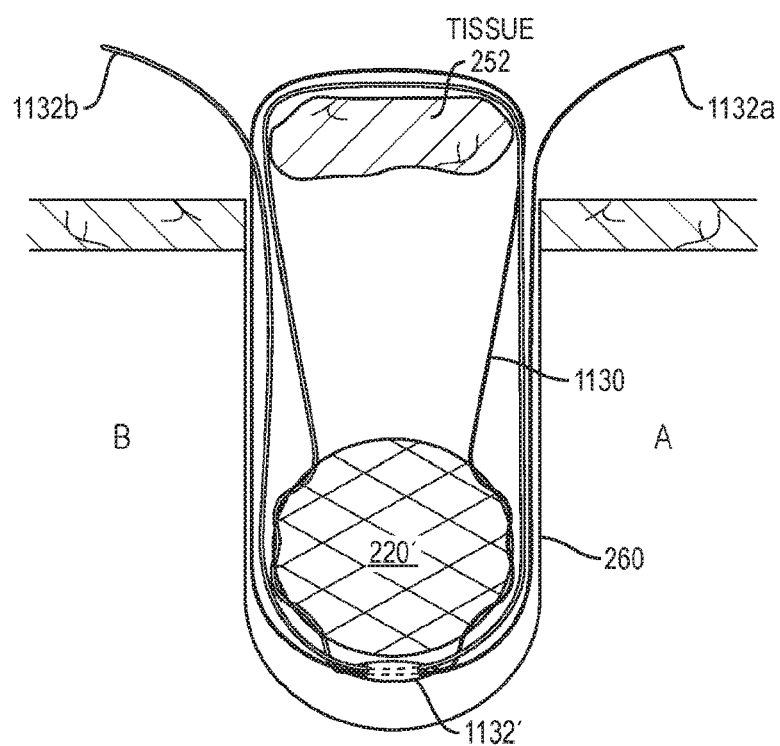
Figure 11C:
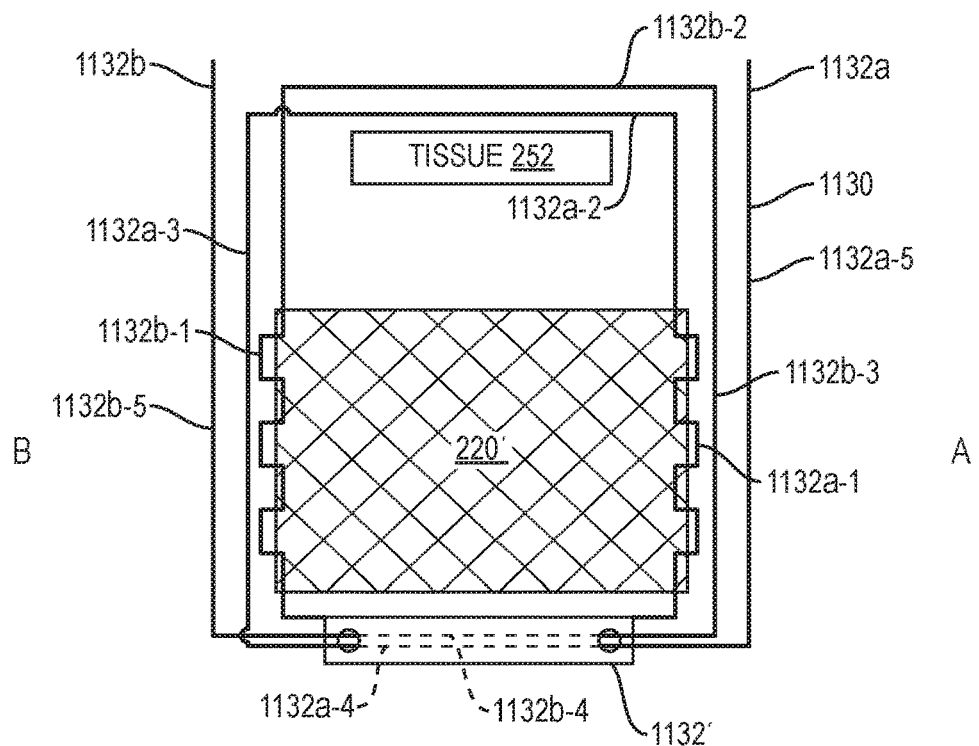
FIG. 11C schematically shows suture routing through a deployed anchor shown in FIG. 11B.

The discussion will now turn to FIGS. 11A-11C, illustrating a tissue repair system and a method of use that may be knotless. In general, FIGS. 11A-11C disclose a double loop simultaneous activation tissue repair system that has a single suture that forms a double loop and acts as an expansion suture, repair suture and locking suture. Shown in FIG. 11A is a distal end portion of a tissue repair system 1100 as provided, which may generally include a tissue repair assembly 1101, insertion instrument 1110 and may include two snare tools 1140a and 1140b. Insertion instrument 1110 may include an outer tube 1102 and inner tube 1104, slideably disposed along the outer tube 1102. Insertion instrument 1110 may be similar to that generally described in U.S. Publication No. 2013/0123810 (Brown et al.), herein incorporated in its entirety by reference. The tissue repair assembly 1101 may include a soft anchor 220 similar to the tissue repair assembly 100 of FIGS. 1A-C. As illustrated shown in FIG. 11A, soft anchor 220 may be provided contained within insertion instrument 1110, with an expansion suture 1130 interwoven therethrough, in a similar manner to that shown and described in FIGS. 1A-1C, except that a portion of the expansion suture 1130 may include a longitudinal passage length 1132, and may include two snaring tools 1140a and 1140b extended therethrough. Expansion suture 1130 may define a lumen along its entire length and therefore in some embodiments, longitudinal passage length 1132 is formed or defined simply by the presence of a snare tool therethrough (described later). In other embodiments, a portion of the expansion suture is provided deformed into an expanded or dilated form (as shown in FIGS. 5A-5C for example) that may hold this longitudinal passage form with or without a snare tool present. Tension on at least one end of the longitudinal passage portion 1132 is operable to reduce the suture lumen diameter of the longitudinal passage form and cinch around any flexible member extending therethrough, to aid in knotlessly locking the assembly.

Each snaring tool 1140*a* and 1140*b* generally may include a loop end 1142*a* and 1142*b* to receive ends of the expansion suture 1132*a* and 1132*b*. Each snaring tool 1140*a* and 1140*b* may extend along an external surface of the soft anchor 220, through longitudinal passage length 1132 before extending proximally along an opposing side of the anchor 220 and through a portion of insertion instrument 1110. (Alternatively snaring tool 1140*a* and 1140*b* may extend through longitudinal passage length 1132 similar to the routing shown in FIG. 2A. In this case the soft tissue 252 may necessarily be coupled while the instrument 1110 is disposed outside the patient, and the suture ends are first coupled to tissue and then drawn out of the patient for threading through snares 1140*a* and 1140.)

Each snaring tool 1140*a* and 1140*b* may have a corresponding handle end 1144*a* and 1144*b*. Snare handle ends 1144*a* and 1144*b* may alternatively be connecting ends to a mechanism incorporated with other portions of a handle portion of insertion instrument 1110 for example (not shown). In other embodiments, snare tool may be a length of suture that extends through the longitudinal passage length 1132 including a bight loop end defining the snaring suture loop configured to capture the expansion suture 1130 suture therethrough. Expansion suture 1130 may be provided at least partially interwoven along the soft anchor 220 resulting in two ends 1132*a* and 1132*b* extending as provided from a proximal end of anchor 220.

FIG. 11B represents the tissue repair assembly 1101 in a deployed and knotlessly locked configuration. In deployed state anchor 220' is anchored be wedged against and potentially into tunnel walls. The inventors envision that the double loop configuration, as described later, together with a cinched longitudinal passage portion may knotlessly lock the assembly 1101. The steps between the configuration shown in FIG. 11A and FIG. 11B are as follows. With the assembly 1101 still contained within the instrument 1110, ends 1132*a* and 1132*b* may be looped around or stitched through tissue 252. Each end 1132*a* and 1132*b* may then extend through a snare loop, end 1132*a* through snare loop 1142*a* and end 1132*b* through 1142*b* and snare handle ends (1144*a* and 1144*b*) drawn so as to draw suture ends 1132*a* and 1132*b* over each other to opposing sides of and along an external surface of the soft anchor 220. Stated otherwise, expansion suture end 1132*a* may extend from a proximal end of side A of the soft anchor 220, defining a starting point for expansion suture end 1132*a*. Expansion suture end 1132*a* may engage tissue and extend through a loop end 1142*a* of snaring tool 1140*a*. Snaring tool 1140*a* may then draw expansion suture end 1132*a* in a full loop around an external surface of the soft anchor 220 to return to the proximal end of side A. More specifically snaring tool 1140*a* may draw expansion suture end 1132*a* to a proximal end of side B of the soft anchor 220 and along a pathway including, along the anchor 220 and towards a distal end of anchor 220, through longitudinal passage length 1132 crossing over to side A followed by along the anchor 220 on side A and extending out of the proximal end of anchor so as to form a first expansion suture loop. Expansion suture end 1132*b* may essentially make an equivalent loop in the opposite direction than expansion suture end 1132*a* to return to a suture end 1132*b* starting point seen in FIG. 11A. More specifically snaring tool 1140*b* may draw expansion suture end 1132*b* over to a proximal end of side A of the soft anchor 220 and along a pathway including along the anchor 220 and towards and over a distal-most end of anchor 220, through longitudinal passage length 1132 crossing over the suture end 1132*a* to side B followed by along the anchor 220 on side B and extending out of the proximal end of anchor so as to form a second expansion suture loop. The first and second expansion suture loop may extend through the longitudinal passage length 1132 to cross over each other. Formation of these two expansion suture loops may be preferably formed with the assembly 1101 contained within the insertion instrument 1110 and therefore in an elongate configuration. Both ends 1132*a* and 1132*b* of expansion suture 1130 may be drawn further through longitudinal passage portion 1132 to draw tissue 252 towards the system 1100 while tissue repair assembly 1101 is contained within the insertion instrument 1110 and also before insertion instrument is inserted into a bone tunnel 260.

Longitudinal passage length 1132 may be provided in a radially expanded configuration to receive a snare tool. Longitudinal passage length 1132 may extend across a distal end of soft anchor 220 and orthogonal to the soft anchor longitudinal axis. Longitudinal passage length 1132 may extend across a substantial portion of the soft anchor 220 width or diameter. Longitudinal passage length 1132 includes an entrance opening and exit opening, both openings at the distal end of anchor 220. A longer longitudinal passage length 1132 generally increases friction between the longitudinal passage length 1132 and suture loops that extends therethrough.

Longitudinal passage length 1132 may therefore be approximately equivalent to a diameter or width of the all-suture anchor 220, or potentially longer to wrap around and extend along the lateral sides of soft anchor 220 for example. Friction may also however be increased by increasing tension on the longitudinal passage length 1132. Therefore, the inventors envision a series of combinations of tension on the expansion suture 1130 and length of longitudinal passage length 1132, whereby the longer the longitudinal passage length 1132, the less tension may be required on the longitudinal passage length in order to secure the system in a locked configuration. Longitudinal passage length 1132 may vary from 1-8 mm, and may preferable between 2-3 mm. The outer diameter of the expansion suture may be USP #2, 0.5-0.599 mm The tissue repair system 1100 may then be placed into bone tunnel 260 and some further approximation of the tissue 252 may be preferable at this point before ejecting the assembly 1101 from the insertion instrument 1110. A first tension may be applied to ends 1132*a* and 1132*b* while assembly 1101 is disposed within the insertion instrument 1110 and insertion instrument is disposed within or along the bone tunnel 260, as this limits deformation of the soft anchor 220 and may draw tissue 252 towards soft anchor 220. The inventor envisions an additional option including partial deployment of the assembly 1101 or partial retraction of the outer tube 1102 to partially expand the suture anchor 220. A second higher tension may then be applied on the ends 1132*a* and 1132*b* with the soft anchor 220 partially expelled from outer tube 1102 and within the bone tunnel 260 to alter the configuration of the soft anchor 220 to a partially radially expand state 220' and possibly further approximate the tissue 252 towards the bone. A third high tension may then be applied with the soft anchor 220 fully expelled from the outer tube 1102, the third higher tension configured to deform the anchor 220 to engage the walls of the tissue tunnel 260 and wedge the tissue repair assembly 1101 within the pre-formed tunnel 260, similar to configuration shown in FIG. 1C. Of note longitudinal passage length 1132 may still be partially radially expanded. Applying a fourth tension on the expansion suture ends 1132a and 1132b may elongate longitudinal passage portion 1132' to cinch around the first and second expansion loops further locking the tissue 252 in place. In addition, the fourth tension on the expansion suture 1130 may draw longitudinal passage length 1132' at least partially into a portion of the soft anchor 220'. Each successive tension may be higher relative to the previous tension. Expansion suture ends 1132a and 1132b may be operably coupled to a control in insertion instrument handle (not shown) that may be operable to control the first through fourth tensions on the expansion suture 1130. Ends 1132a and 1132b may then be trimmed, with no further knots or securing means required.

FIG. 11C is a schematic of tissue repair assembly 1101 in a deployed and locked configuration as shown in FIG. 11B showing the pathway of the expansion suture 1130 to form the double suture loops. Tissue repair assembly 1101 is shown with soft anchor 220' in a deployed and expanded configuration. Soft tissue 252 is approximated to the bone tissue 260; the longitudinal passage length 1132 is in an elongate and radially reduced (lesser dilated) configuration 1132' to secure the two expansion suture loops. Longitudinal passage length 1132' is disposed at a distal-most end of soft anchor 220'. Expansion suture 1130 defines longitudinal passage length 1132 with two limbs 1132a and 1132b extending from opposing ends of longitudinal passage length 1132, both limbs 1132a and 1132b extending through walls of the soft anchor 220' towards a proximal end of anchor 220' defining lengths 1132a-1 and 1132b-1. Limb 1132a defines a first loop that extends over tissue 1132a-2, along an external surface of anchor (220') 1132a-3, through the lumen of the longitudinal passage length 1132a-4 and then along an external surface of anchor 220' to extend from the anchor proximal end 1132a-5. 1132b defines a second loop that extends over tissue 1132b-2, crossing over 1132a-2, along an external surface of anchor 220' 1132b-3, through the lumen of the longitudinal passage length 1132b-4 and then along an external surface of anchor 220' to extend from the anchor proximal end 1132b-5.

Figure 12A:
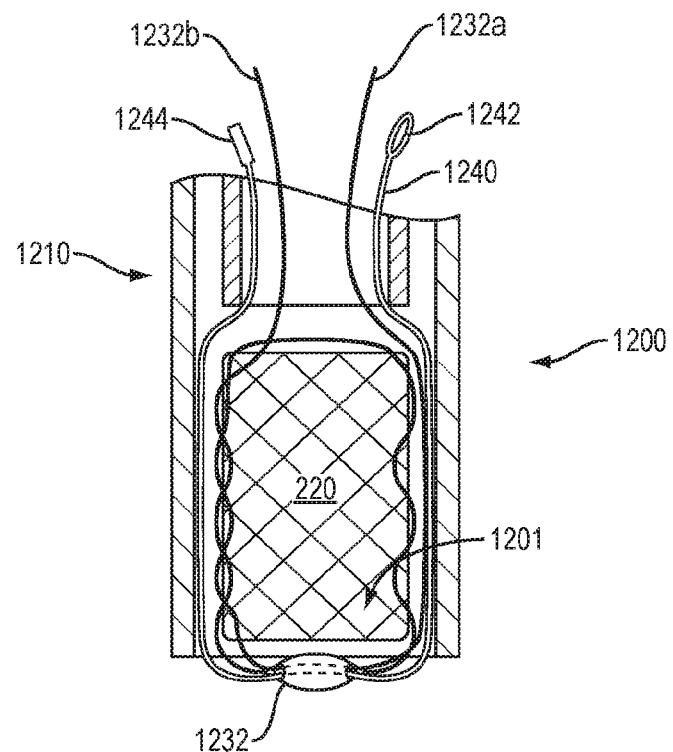
FIGS. 12A-12B illustrates an alternative embodiment of a tissue repair assembly with two suture loops, only one coupled to soft tissue, before and after deployment respectively in accordance with this disclosure.
Figure 12B:
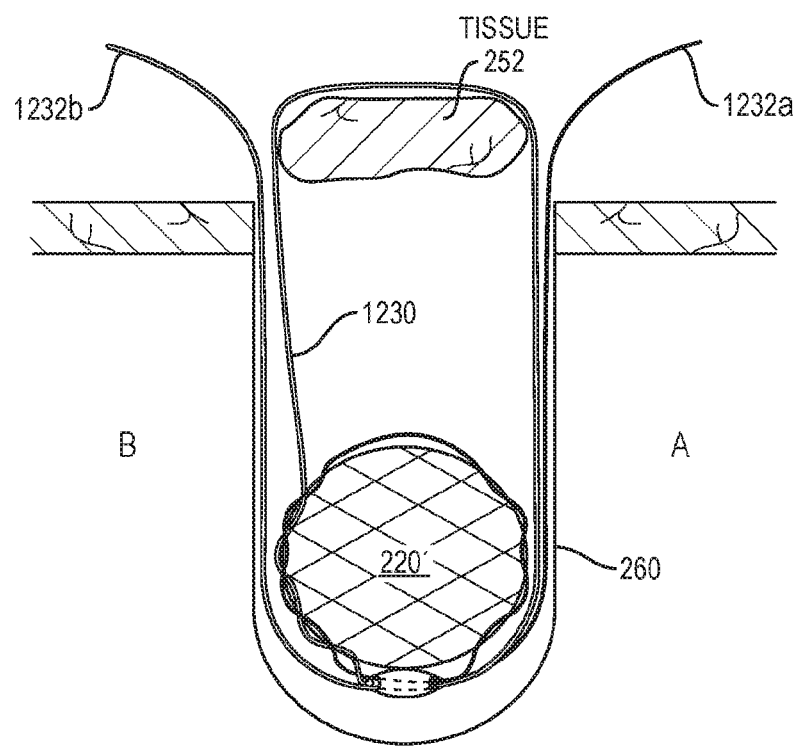
Figure 12C:
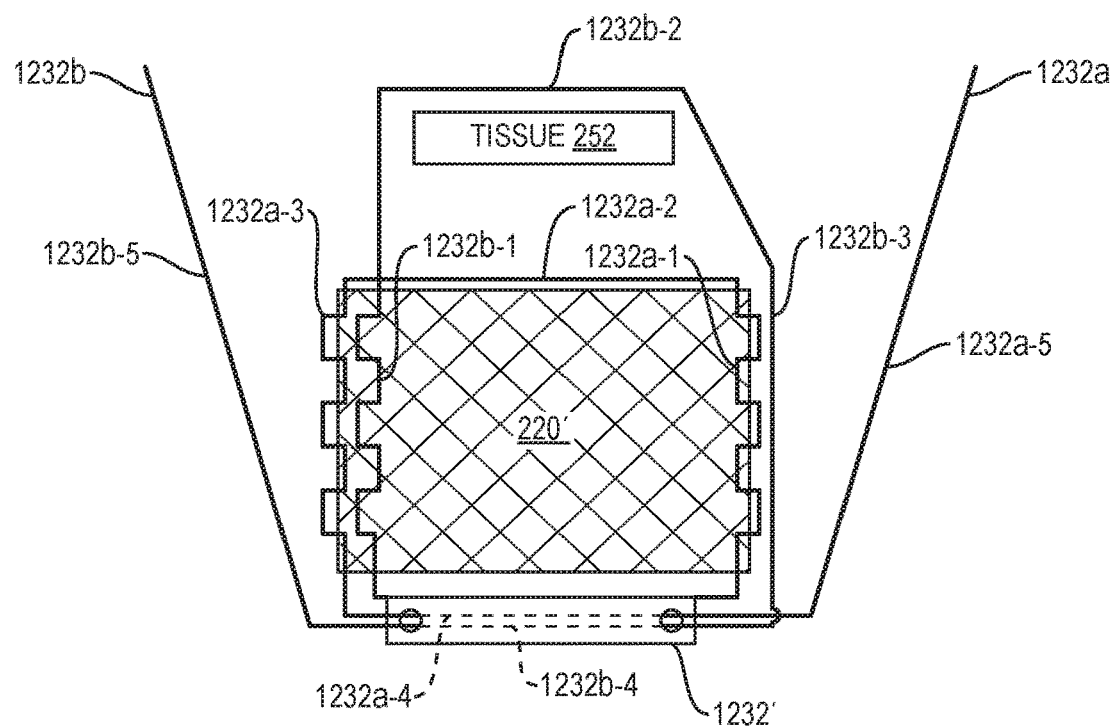
FIG. 12C schematically shows suture routing through a deployed anchor shown in FIG. 12B.

An alternative routing embodiment is shown in FIGS. 12A-12C, illustrating a tissue repair system and a method of use with a continuous loop of expansion suture with both free ends passed through longitudinal passage length at distal end and a single loop around tissue 252. This may allow a degree of control emphasis; tension on one suture limb may be preferably configured to radially expand or deploy the anchor 220, and tension on the other suture limb may preferably approximate the tissue 252. Shown in FIG. 12A is a distal end portion of a tissue repair system 1200 as provided, which may generally include a tissue repair assembly 1201, insertion instrument 1210 and may include one snare tool 1240. Insertion instrument 1210 may be similar to that generally described in U.S. Publication No. 2013/0123810 (Brown et al.), herein incorporated in its entirety by reference. The tissue repair assembly 1201 may include a soft anchor 220 similar to the tissue repair assembly 100 of FIGS. 1A-C. As schematically shown in FIG. 12A, soft anchor 220 may be provided contained within insertion instrument 1210, with an expansion suture 1230 interwoven therethrough. A portion of the expansion suture 1130 may include a longitudinal passage length 1232, and may include a snaring tool 1240. Expansion suture 1230 may define a lumen along its entire length and therefore in some embodiments, longitudinal passage length 1232 is formed or defined simply by the presence of a snare tool therethrough (described later). In other embodiments, a portion of the expansion suture 1230 is provided deformed into a longitudinal passage form (as shown in FIGS. 5A-5C for example) that may hold this longitudinal passage form with or without a snare tool present.

Snaring tool 1240 generally may include a loop end 1242 to receive an end 1232b of the expansion suture. Snaring tool 1240 as provided may extend along an external surface of the soft anchor 220, through longitudinal passage length 1232 before extending proximally along an opposing side of the anchor 220 and through a portion of insertion instrument 1210. Snaring tool 1240 may have a handle end 1244 that connect to a mechanism incorporated with other portions of a handle portion of insertion instrument 1210 for example (not shown). In other embodiments, snare tool may be a length of suture that extends through the longitudinal passage length 1232 including a bight loop end defining the snaring suture loop configured to capture the expansion suture 1230 suture therethrough. Expansion suture 1230 may be provided interwoven along the soft anchor 220 resulting in two ends 1232a and 1232b extending as provided from a proximal end of anchor 220. In this embodiment, expansion suture 1230 may be provided interwoven to form one complete loop around soft anchor 220. Seen best in FIG. 12C, expansion suture defines longitudinal passage length 1232 with two ends 1232a and 1232b extending from opposing ends of longitudinal passage length, both ends 1232a and 1232b extending through walls of the soft anchor 220 towards a proximal end of anchor 220 defining length 1232a-1 and 1232b-1. 1232a may define a first expansion suture loop already routed through anchor as provided, that extends over anchor 1232a-2, and interwoven back through anchor 1232a-3, through the lumen of the longitudinal passage length 1232a-4 and then along an external surface of anchor 220 to extend from the anchor proximal end 1232a-5.

With the assembly 1201 still contained within the instrument 1210, end 1232b may be looped around or stitched through tissue 252. End 1232b may then extend through snare loop 1242 and snare handle end 1244 drawn to draw suture end 1232b over to an opposing side of and along an external surface of the soft anchor 220. Stated otherwise, expansion suture end 1232b may extend from a proximal end of side B of the soft anchor 220, defining a starting point for a second loop of expansion suture end 1232b. Expansion suture end 1232b may engage tissue and extend through a loop end 1242 of snaring tool 1240. Snaring tool 1240 essentially may then draw expansion suture end 1232b in a full loop around an external surface of the soft anchor 220 to return to the proximal end of side B. More specifically snaring tool 1240 may draw expansion suture end 1232b to a proximal end of side A of the soft anchor 220 and along a pathway including along the anchor 220 and towards a distal end of anchor 220, through longitudinal passage length 1232 crossing over to side B followed by along the anchor 220 on side B and extending from the proximal end of anchor to form second expansion suture loop. The first and second expansion suture loops may extend through the longitudinal passage length 1232 to cross over each other. Second expansion suture loop may be preferably formed with the assembly 1201 contained within the insertion instrument 1210 and therefore in an elongate configuration. End 1232b of expansion suture 1230 may be drawn further through longitudinal passage portion 1232 to draw tissue 252 towards the anchor 220 while tissue repair assembly 1201 is contained within the insertion instrument 1210 and also before insertion instrument is inserted into a bone tunnel 260. Longitudinal passage length 1232 may be provided in a radially expanded configuration to receive a snare tool and longitudinal passage length may extend across a distal end of soft anchor 220 and orthogonal to the soft anchor longitudinal axis. The inventor also envisions that the longitudinal passage length 1232 may alternatively be along a side of the soft anchor or proximally disposed, across a width of a proximal end of the soft anchor 220. Longitudinal passage length 1232 may extend across a substantial portion of the soft anchor width or diameter and may have similar options for lengths to control frictional hold between the longitudinal passage length and sutures extending there-along.

The tissue repair system 1200 may then be placed into bone tunnel 260 and some further approximation of the tissue 252 may be preferable at this point before ejecting the assembly 1201 from the insertion instrument 1210. Therefore a first tension may be applied to end 1232b while assembly 1201 is disposed within the insertion instrument 1210, as this limits deformation of the soft anchor 220 and may draw tissue 252 towards soft anchor 220. The inventor envisions an additional option including partial deployment of the assembly 1201 or partial retraction of the outer tube to partially expand the suture anchor 220 to further approximate tissue 252. A second tension may then be applied on the end 1232a (and possibly also 1232b) with the soft anchor 220 partially expelled from outer tube 1202 and within the bone tunnel 260 to alter the configuration of the soft anchor 220 to a partially radially expand state 220' and possibly further approximate the tissue 252 towards the bone. Generally, tension on end 1232a may more preferably or more directly radially expand anchor 220, while tension on end 1232b may both draw tissue 252 closer to anchor 220 and contribute to the deployment of anchor 220. A third tension may then be applied with the soft anchor 220 fully expelled from the outer tube 1202, the third higher tension configured to engage the walls of the tissue tunnel 260 and wedge the tissue repair assembly 1201 within the pre-formed tunnel 260, similar to configuration shown in FIG. 1C. Of note longitudinal passage length, 1232 may still be partially radially expanded. Applying a fourth tension on the expansion suture ends 1232a and 1232b may elongate longitudinal passage portion 1232' to cinch around the first and second expansion loops further locking the tissue 252 in place. In addition, the fourth tension on the expansion suture 1230 may draw longitudinal passage length 1232' at least partially into a portion of the soft anchor 220'. Each successive tension may be higher relative to the previous tension. Expansion suture ends 1232a and 1232b may be operably coupled to a control in insertion instrument handle (not shown) that may be operable to control the first through fourth tensions on the expansion suture 1230.

FIG. 12C is a schematic of tissue repair assembly 1201 in an anchoring and locked configuration as shown in FIG. 12B showing the pathway of the expansion suture 1230 to form the two suture loops. Tissue repair assembly 1201 is shown with soft anchor 220' in a deployed and expanded configuration. Soft tissue 252 is approximated to the bone tissue; the longitudinal passage portion 1232 is in an elongate and radially reduced (lesser dilated) configuration 1232' to secure the two expansion suture loops. Longitudinal passage length 1232' is disposed at a distal-most end of soft anchor 220'. Expansion suture defines longitudinal passage length 1232 with two ends 1232a and 1232b extending from opposing ends of longitudinal passage length, both ends 1232a and 1232b extending between braids of the soft anchor 220' towards a proximal end of anchor 220' defining length 1232a-1 and 1232b-1. 1232a defines a first loop that extends over anchor 220' 1232a-2, along an external surface of anchor 220', 1232a-3, through the lumen of the longitudinal passage length 1232a-4 and then along an external surface of anchor 220' to extend from the anchor proximal end 1232a-5. This first loop may be provided pre-routed through anchor in the first loop. 1232b defines a second loop that extends over or through tissue 1232b-2, along an external surface of anchor 220' 1232b-3, through the lumen of the longitudinal passage length 1232b-4 and then along an external surface of anchor 220' to extend from the anchor proximal end 1232b-5. Lengths 1232a-3 and 1232b-1 may extend through the same portion of anchor 220, extending between the same braided portions. Alternatively, 1232a-3 and 1232b-1 may be circumferentially spaced from each other, extending between braided portions of anchor 220 that are spaced apart. Alternatively 1232b-1 may extend along an external surface of the anchor 220 and may not necessarily interweave along the anchor 220. Ends 1232a and 1232b may then be trimmed without the need for further means of securement such as a knot or clip.

Figure 13A:
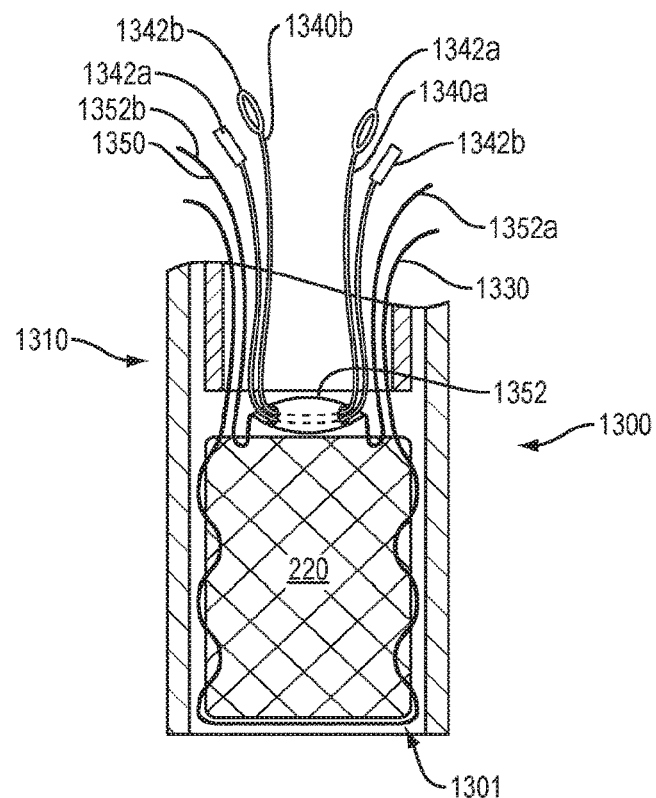
FIGS. 13A-13B illustrates an alternative embodiment with two suture loops and a proximally disposed longitudinal passage portion, before and after deployment respectively, in accordance with this disclosure.
Figure 13B:
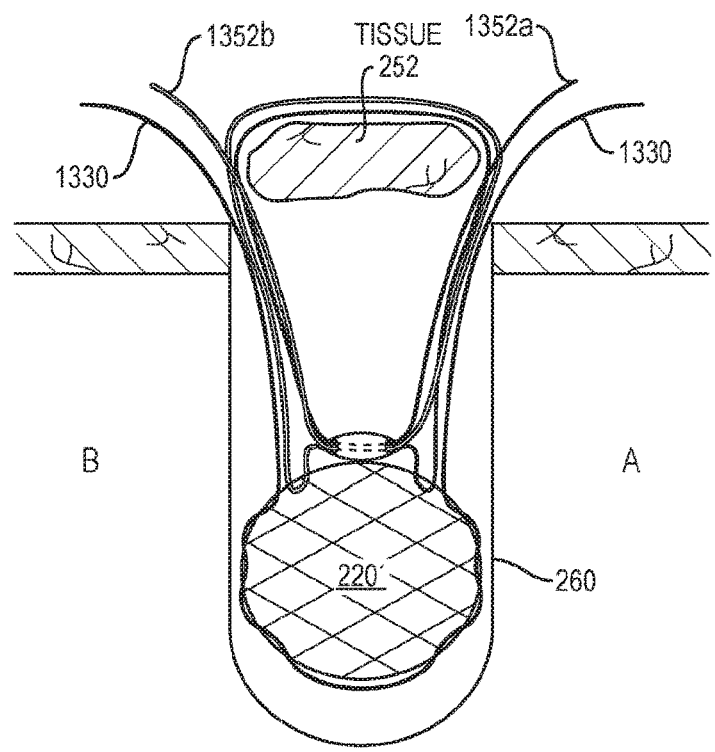
Figure 13C:
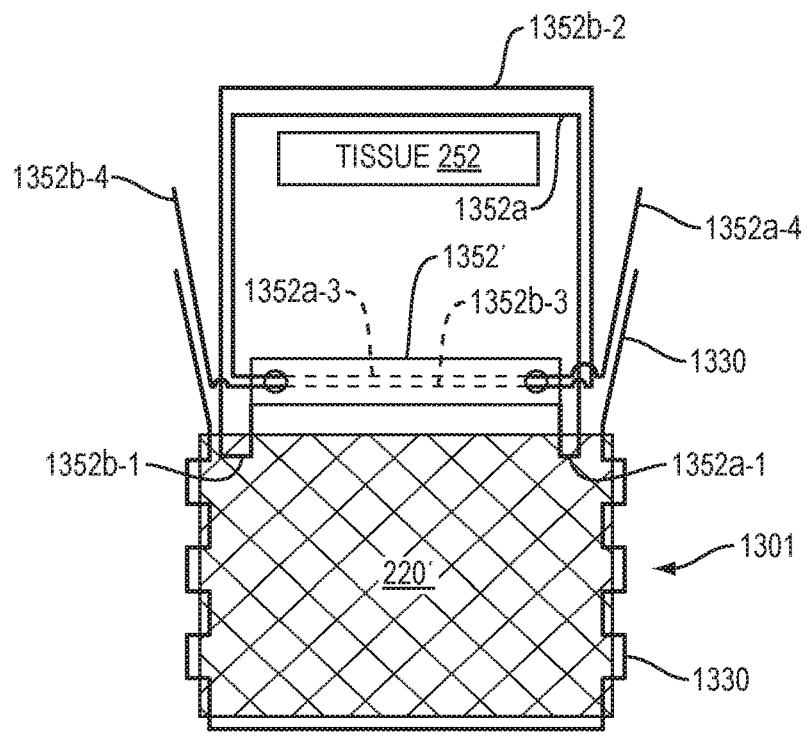
FIG. 13C schematically shows suture routing through a deployed anchor shown in FIG. 13B.

An alternative suture routing embodiment is disclosed in FIGS. 13A-13C, illustrating a tissue repair system and a method of use. This embodiment includes a longitudinal passage portion 1352 towards the proximal end of anchor 220, which may allow for tissue attachment after the anchor has been inserted into bone. This embodiment also represents a separate expansion suture 1330 that may not include a longitudinal passage portion, the longitudinal passage portion formed in a separate suture and therefore expansion and repair suture securement may be more independently controlled. Expansion suture 1330 and repair suture 1350 are therefore separately formed and independently operatively coupled to the anchor 220. Shown in FIG. 13A is a distal end portion of a tissue repair system 1300, as provided which may generally include a tissue repair assembly 1301, insertion instrument 1310 and may include two snare tools 1340a and 1340b. Insertion instrument 1310 may be similar to that generally described in U.S. Publication No. 2013/0123810 (Brown et al.), herein incorporated in its entirety by reference. The tissue repair assembly 1301 may include a soft anchor 220 similar to the tissue repair assembly 100 of FIGS. 1A-C. As shown in FIG. 13A, soft anchor 220 may be provided contained within insertion instrument 1310, with an expansion suture 1330 interwoven therethrough, in a similar manner to that shown and described in FIGS. 1A-1C. In this embodiment, a separate repair suture 1350 may include a longitudinal passage length 1352 and may include two snaring tools 1340a and 1340b extended therethrough. Repair suture 1350 may define a lumen along its entire length and therefore in some embodiments, longitudinal passage length 1352 is formed or defined simply by the presence of a snare tool therethrough (described later). In other embodiments, a portion of the repair suture is provided deformed into a dilated form (as shown in FIGS. 5A-5C for example) that may hold this dilated form with or without a snare tool present.

Each snaring tool 1340a and 1340b generally may include a loop end 1342a and 1342b to receive ends of the repair suture 1152a and 1352b and may also extend through longitudinal passage length 1352 before extending proximally and through a portion of insertion instrument 1310. Each snaring tool 1340a and 1340b may have a corresponding handle end 1344a and 1344b. Snare handle ends 1344a and 1344b may alternatively be connected to a mechanism incorporated with other portions of a handle of insertion instrument 1310 for example (not shown). In other embodiments, snare tool may be a length of suture that extends through the longitudinal passage length 1352 including a bight loop end defining the snaring suture loop configured to capture the repair suture 1350 suture therethrough. Expansion suture 1330 may be provided interwoven along the soft anchor 220 resulting in two ends extending as provided from a proximal end of anchor 220.

System 1300 may include a longitudinal passage length 1352 disposed at a proximal end of anchor 220 and thereby the assembly 1301 may be first inserted to a bone tunnel 260 and also deployed or radially expanded before coupling repair suture to tissue 252. This may allow for independent activation of the anchor deployment and independent tissue approximation, which may be preferable. Ends 1352*a* and 1352*b* may therefore be looped around or through tissue 252, with the assembly 1301 either still contained within the instrument 1310 or disposed within the bone tunnel 260. Ends 1352*a* and 1352*b* may then extend through snare loops, end 1352*a* through snare loop 1342*a* and end 1332*b* through 1342*b* and snare handle ends (1344*a* and 1344*b*) drawn so as to draw suture ends 1352*a* and 1352*b* over each other to opposing sides of the soft anchor 220. Stated otherwise, repair suture end 1352*a* may extend from a proximal end of side A of the soft anchor 220, defining a starting point for repair suture end 1352*a*. Repair suture end 1352*a* may engage tissue and extend through a loop end 1342*a* of snaring tool 1340*a*. Snaring tool 1340*a* essentially may then draw repair suture end 1352*a* in a loop, the entire loop disposed adjacent a proximal end of anchor 220. More specifically snaring tool 1340*a* may draw repair suture end 1352*a* to a proximal end of side B of the soft anchor 220 through longitudinal passage length 1352 crossing over to side A followed by extending out of the proximal end of anchor 220 so as to form a first repair suture loop. Repair suture end 1352*b* may essentially make an equivalent loop in the opposite direction to repair suture end 1352*a* to return to a suture end 1352*b* starting point seen in FIG. 13A. FIG. 13B represents the tissue repair assembly 1301 in a deployed and locked configuration with both repair suture loops around tissue 252. All-suture anchor is shown in a deployed state 220' and should wedge up against and potentially into the surrounding tissue 260, similar to FIG. 2D for example It is shown separated from the tissue to better show the suture routing. More specifically snaring tool 1340*b* may draw repair suture end 1352*b* over to a proximal end of side A of the soft anchor 220, through longitudinal passage length 1352 crossing over the suture end 1352*a* to side B and out of the proximal end of anchor so as to form a second repair suture loop. The first and second repair suture loops may extend through the longitudinal passage length 1352 to cross over each other. Formation of these two repair suture loops may be preferably formed with the assembly 1301 already locked with the bone tunnel 260. Longitudinal passage length 1352 may be provided in a radially expanded configuration to receive a snare tool and longitudinal passage length may extend across a distal end of soft anchor 220 and orthogonal to the soft anchor longitudinal axis. Longitudinal passage length 1352 may extend across a substantial portion of the soft anchor width or diameter. Longitudinal passage length 1352 includes an entrance opening and exit opening, both openings at the proximal end of anchor 220. Dilation length 1352 may define a length sufficient to cooperate with a coefficient of friction of the repair suture and/or tension on the longitudinal passage length 1352 similar to other longitudinal passage lengths described in previous embodiments.

The method of use may therefore start with system 1300 into a bone tunnel 260 and expelling the anchor 220 from the instrument 1310. Tension on ends of expansion suture 1330 may then be applied to radially expand anchor 220 and anchor the system 1301 within the tunnel 260. Repair suture 1350 may then be routed through or around tissue and through longitudinal passage length as described above. Tension on ends of repair suture 1352*a* and 1352*b* may then be applied to approximate the tissue 252 towards the bone. Increased tension may then be applied on ends of repair suture 1352*a* and 1352*b* to further elongate longitudinal passage portion 1352' to cinch around the first and second repair loops further locking the tissue 252 in place. Expansion suture ends 1330 may be operably coupled to a control in insertion instrument handle (not shown) that may be operable to control the applied tension. In some embodiments the tissue repair system 1300 may be placed into bone tunnel 260 with the tissue attached via repair suture; additional openings in the insertion instrument 1310 may be required in order to access longitudinal passage length in this case.

FIG. 13C is a schematic of tissue repair assembly 1301 in an anchoring and locked configuration as shown in FIG. 13B, illustrating the pathway of the expansion suture 1330 and repair suture 1350 to form the two suture loops. Tissue repair assembly 1301 is shown with soft anchor 220' in a deployed and expanded configuration. Soft tissue 252 is approximated to the bone tissue; the longitudinal passage portion 1352 is in an elongate and radially reduced (lesser dilated) configuration 1352' to secure the two repair suture loops. Longitudinal passage length 1352' is disposed at a proximal-most end of soft anchor 220'. Repair suture defines longitudinal passage length 1352 with two ends 1352*a* and 1352*b* extending from opposing ends of longitudinal passage length 1352, at least one end (1352*a* or 1352*b*) extending through a portion of the soft anchor 220' so as to couple the repair suture 1350 to the anchor 220. This portion is shown as 1352*a*-1 and 1352*b*-1. In alternative embodiments portion only a single repair loop of suture may couple to tissue 252 and 1352*a*-1 for example may be provided extending around and through the soft anchor, similar to the path taken by expansion suture 1330 for example. 1352*a* defines a first loop that extends over tissue 1352*a*-2, through the lumen of the longitudinal passage length 1352*a*-3 and then proximally extends away from the anchor proximal end 1352*a*-4. 1352*b* defines a second loop that extends over tissue 1352*b*-2, crossing over 1352*a*-2, through the lumen of the longitudinal passage length 1352*b*-3 and then extends proximally away from the anchor proximal end 1352*b*-4.

Figure 14A:
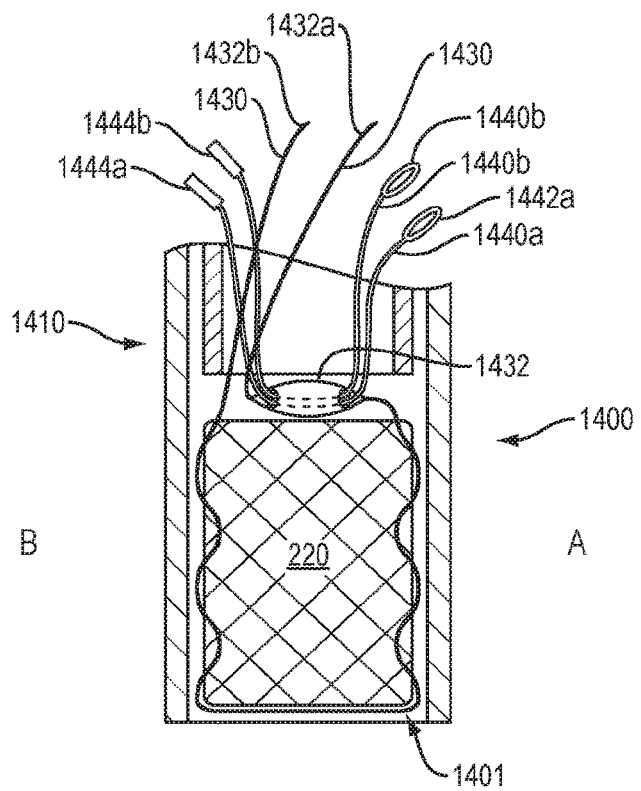
FIGS. 14A-14B illustrates an alternative embodiment with two suture loops and a proximally disposed longitudinal passage portion, before and after deployment respectively, in accordance with this disclosure.
Figure 14B:
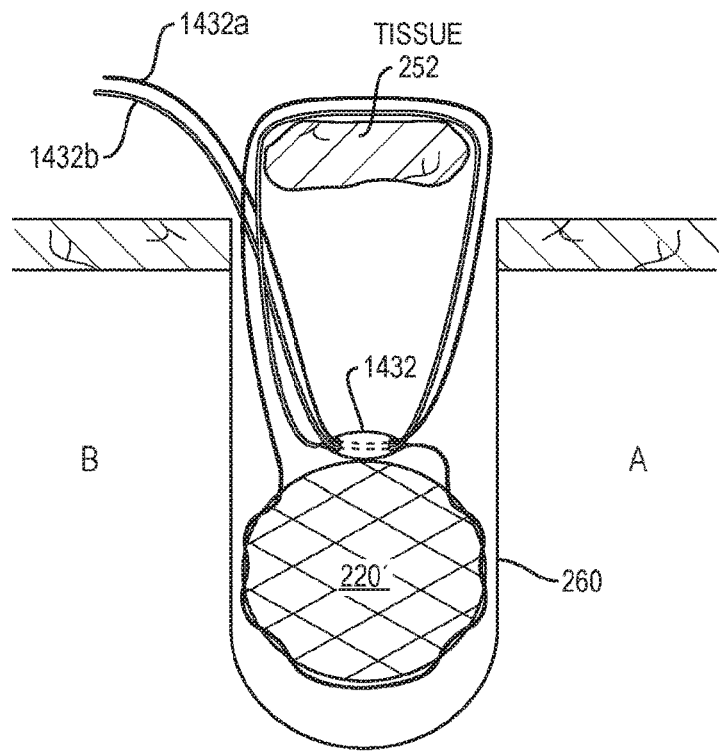
Figure 14C:
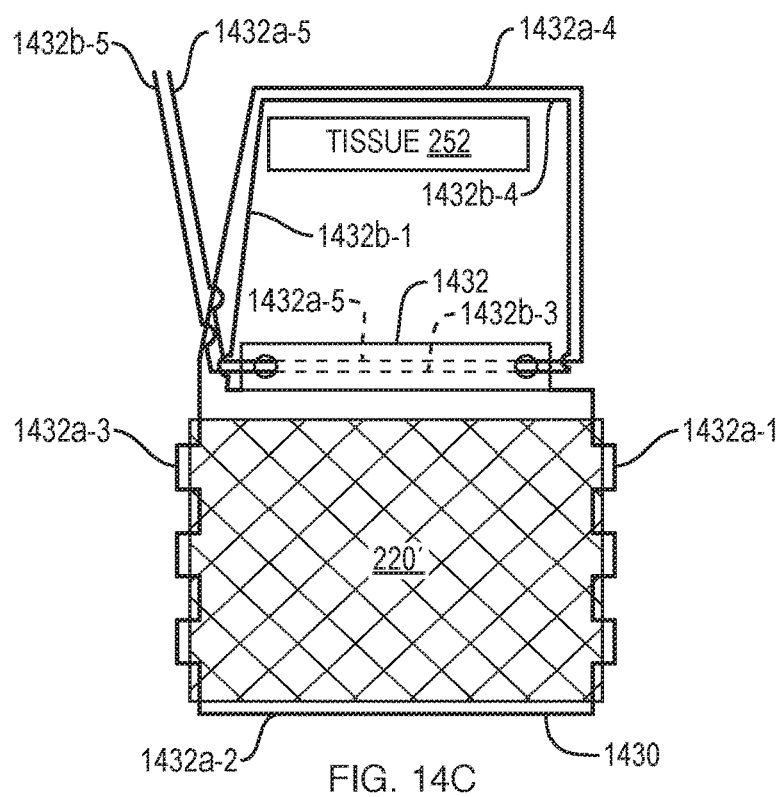
FIG. 14C schematically shows suture routing through a deployed anchor shown in FIG. 14B.

FIGS. 14A-14C, illustrating an alternative embodiment of tissue repair system and a method of use with alternative suture routing, with a single continuous suture. Shown in FIG. 14A is a distal end portion of a tissue repair system 1400 as provided, which may generally include a tissue repair assembly 1401, insertion instrument 1410 and may include two snare tools 1440*a* and 1440*b*. Insertion instrument 1410 may be similar to that generally described in U.S. Publication No. 2013/0123810 (Brown et al.), herein incorporated in its entirety by reference. The tissue repair assembly 1401 may include a soft anchor 220 similar to the tissue repair assembly 100 of FIGS. 1A-C. As schematically shown in FIG. 14A, soft anchor 220 may be provided contained within insertion instrument 1410, with an expansion suture 1430 interwoven therethrough. A portion of the expansion suture 1430 may include a longitudinal passage length or region 1432, and may include two snaring tools 1440*a* and 1440*b* extended therethrough. Longitudinal passage length 1432 is disposed at a proximal end or anchor 220. Expansion suture 1430 may defines a lumen along its entire length and therefore in some embodiments, longitudinal passage length 1432 is formed or defined simply by the presence of a snare tool therethrough (described later). In other embodiments, a portion of the expansion suture is provided deformed into a dilated form (as shown in FIGS. 5A-5C for example) that may hold this dilated form with or without a snare tool present.

Each snaring tool 1440*a* and 1440*b* generally may include a loop end 1442*a* and 1442*b* to receive ends of the expansion suture 1432*a* and 1432*b*. In this embodiment both snare loop ends 1442*a* and 1442*b* may extend through longitudinal passage length and both from the same side, side A of longitudinal passage length 1432. Each snaring tool 1440*a* and 1440*b* may have a corresponding handle end 1444*a* and 1444*b*. Snare handle ends 1444*a* and 1444*b* may alternatively be connecting ends to a mechanism incorporated with other portions of a handle portion of insertion instrument 1410 for example (not shown). In other embodiments, snare tool may be a length of suture that extends through the longitudinal passage length 1432 including a bight loop end defining the snaring suture loop configured to capture the expansion suture 1430 suture therethrough. Expansion suture 1430 may be provided interwoven along the soft anchor 220 resulting in two ends 1432*a* and 1432*b* extending as provided from a proximal end of anchor 220.

Similar to the embodiment disclosed in FIGS. 13A-13C, this assembly may be first deployed into the bone tunnel and then tissue attached. Once the anchor 220 has been expelled, it may then be radially expanded to the form 220' and anchor within the tunnel by applying tension on ends 1432*a* and 1432*b*. One or both suture ends 1432*a* and 1432*b* may then loop around or stitched through tissue 252. Ends 1432*a* and 1432*b* may then extend through snare loops; end 1432*a* through snare loop 1442*a* and end 1432*b* through 1442*b* and snare handle ends (1444*a* and 1444*b*) drawn so as to draw suture ends 1432*a* and 1432*b* over or through the tissue 252, in the same direction as each other, from side B to side A in this embodiment. Stated otherwise, expansion suture end 1432*a* may extend from a proximal end of side B of the soft anchor, defining a starting point for expansion suture end 1432*a*. Expansion suture end 1432*a* may engage tissue and then extend through a loop end 1442*a* of snaring tool 1440*a*. Snaring tool 1440*a* essentially may then draw expansion suture end 1432*a* in a full loop through the longitudinal passage length 1432 to return to the proximal end of side B. More specifically snaring tool 1440*a* may draw expansion suture end 1432*a* towards a proximal end of side A of the soft anchor 220 and along a pathway through longitudinal passage length 1432 crossing over to side B and extending out of the proximal end of anchor 220 to form a first expansion suture loop. Expansion suture end 1432*b* may essentially make an equivalent loop in the same direction as expansion suture end 1432*a* to return to a suture end 1432*b* starting point seen in FIGS. 14A and 14B. More specifically snaring tool 1440*b* may draw expansion suture end 1432*b* over to a proximal end of side B of the soft anchor 220 and along a pathway including through longitudinal passage length 1432 towards side B followed by out of the proximal end of anchor to form a second expansion suture loop. Formation of both expansion suture loops may be preferably formed with the assembly 1401 contained within bone tunnel. Both ends 1432*a* and 1432*b* of expansion suture 1430 may be drawn further through longitudinal passage portion 1432 to draw tissue 252 towards the bone also while tissue repair assembly 1401 is radially expanded. Longitudinal passage length 1432 may be provided in a radially expanded configuration to receive a snare tool and longitudinal passage length 1432 may extend across a proximal end of soft anchor 220 and orthogonal to the soft anchor longitudinal axis. Longitudinal passage length 1432 may extend across a substantial portion of the soft anchor width or diameter. Longitudinal passage length 1432 includes an entrance opening and exit opening, both openings at the distal end of anchor 220. A longer longitudinal passage length 1432 generally increases friction between the longitudinal passage length and suture loops that extends therethrough and may operate similar to longitudinal passage lengths disclosed heretoforth.

Therefore a first tension may be applied to ends 1432*a* and 1432*b* to alter the configuration of the soft anchor 220 to a partially or fully radially expand state 220'. Once tissue is coupled to suture 1430, a second tension may then be applied to approximate the tissue 252 to the bone tunnel 260. Applying a third tension on the expansion suture ends 1432*a* and 1432*b* may elongate longitudinal passage portion 1432' to cinch around the first and second expansion loops further locking the tissue 252 in place. Expansion suture ends 1432*a* and 1432*b* may be operably and selectively coupled to an insertion instrument handle control (not shown) that may be operable to control the first through third tensions on the expansion suture 1430.

FIG. 14C is a schematic of tissue repair assembly 1401 in an anchoring and locked configuration as shown in FIG. 14B showing the pathway of the expansion suture 1430 to form the two suture loops. Tissue repair assembly 1401 is shown with soft anchor 220' in a deployed and expanded configuration. Soft tissue 252 is approximated to the bone tissue; the longitudinal passage portion 1432 is in an elongate and radially reduced (lesser dilated) configuration 1432' to secure the two expansion suture loops. Longitudinal passage length 1432' is disposed at a proximal-most end of soft anchor 220'. Expansion suture defines longitudinal passage length 1432 with two ends 1432*a* and 1432*b* extending from opposing ends of longitudinal passage length, end 1432*a* extending through walls of the soft anchor 220' towards a distal end of anchor 220' defining length 1432*a*-1, loops over a distal end of anchor 220 and extends proximally therefrom defining 1432*a*-2 and 1432*a*-3. End 1432*b* extends proximally from longitudinal passage length 1432 and away from anchor 220. In this configuration, with 1432*a*-1, 1432*a*-2, 1432*a*-3 and 1432*b*-1, the system may be provided within instrument and deployed into a bone tunnel 260. A first loop may then be formed, by end 1432*a* that extends over or through tissue 1432*a*-4, through the lumen of the longitudinal passage length 1432*a*-5 and then proximally from the anchor proximal end 1432*a*-6. Alternatively, the first loop may not loop around tissue and may instead be formed by portion 1432*a*-4 extending through longitudinal passage portion, crossing over 1432*b*-3 followed by exiting the longitudinal passage portion on side A. In this alternative only one loop couples to tissue 252. 1432*b* defines a second loop that extends over tissue 1432*b*-2, through the lumen of the longitudinal passage length 1432*b*-3 and then extends from the anchor proximal end 1432*b*-4. In some alternative embodiments, one of the suture ends may not extend over or through tissue; for example length 1432*a*-4 or 1432*b*-2 may extend over anchor proximal end and not engage tissue. The suture end that does not extend over tissue may then preferably control radial expansion of soft anchor 220, whereas the other suture end that does engage tissue may then preferably control the tissue 252 location.

Figure 15A:
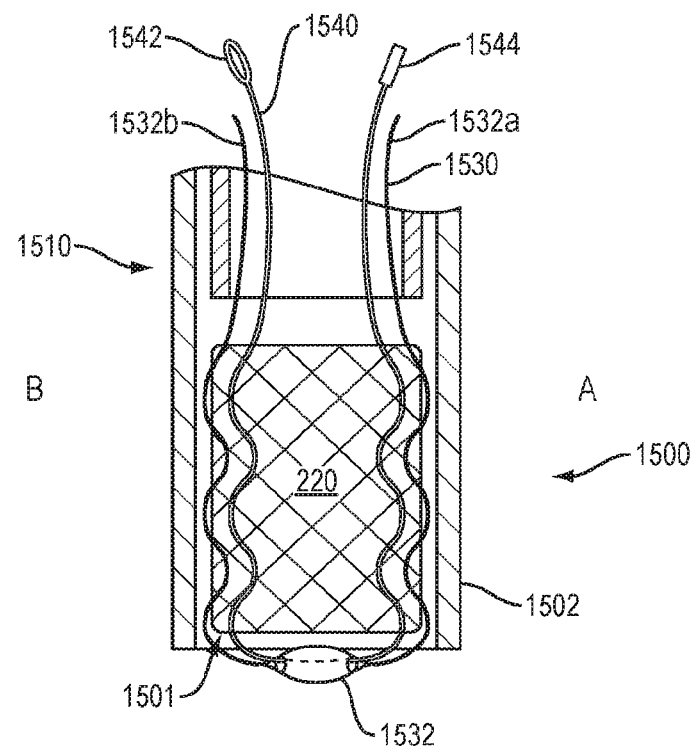
FIG. 15A illustrates an alternative embodiment with a single suture loop, before deployment in accordance with this disclosure.
Figure 15B:
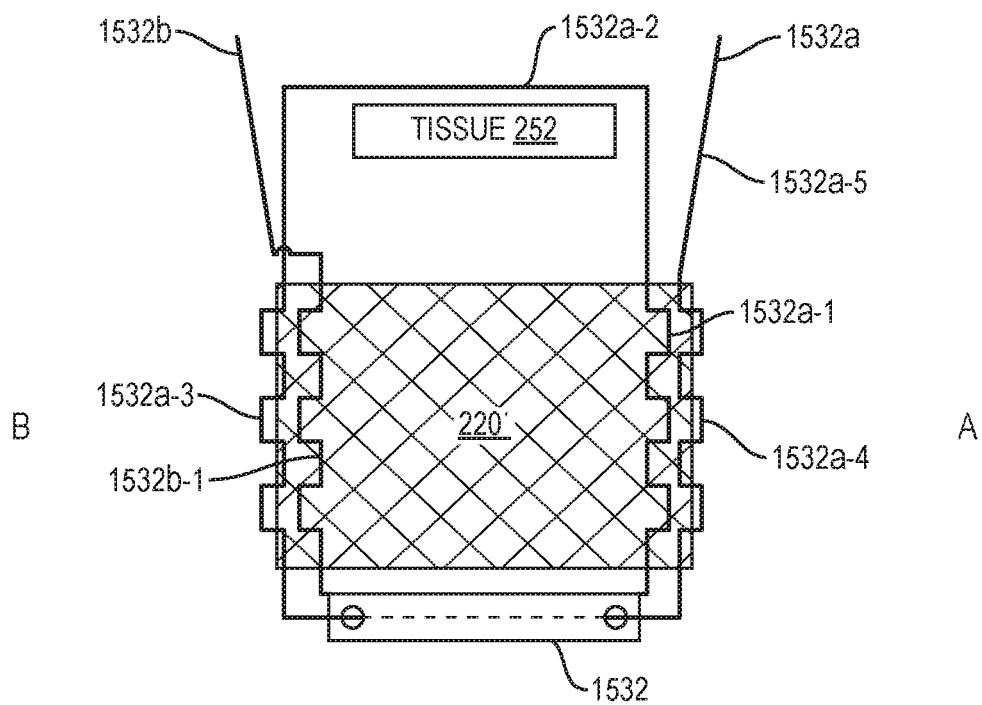
FIG. 15B schematically shows the suture routing of the embodiment shown in the FIG. 15A once deployed, in accordance with this disclosure.

An alternative routing embodiment is shown in FIGS. 15A-15B, illustrating a tissue repair system and a method of use with a continuous loop of expansion suture with one free end passed through longitudinal passage length at distal end and a single loop around tissue. This may allow a degree of separate set of controls; tension on one suture end preferably configured to radially expand or deploy the anchor 220, and tension on the other suture end preferably configured to approximate the tissue. Shown in FIG. 15A is a distal end portion of a tissue repair system 1500 as provided, which may generally include a tissue repair assembly 1501, insertion instrument 1510 and may include one snare tool 1540. Insertion instrument 1510 may be similar to that generally described in U.S. Publication No. 2013/0153810 (Brown et al.), herein incorporated in its entirety by reference. The tissue repair assembly 1501 may include a soft anchor 220 similar to the tissue repair assembly 100 of FIGS. 1A-C, except as described below. As schematically shown in FIG. 15A, soft anchor 220 may be provided contained within insertion instrument 1510, with an expansion suture 1530 interwoven therethrough. A portion of the expansion suture 1530 may include a longitudinal passage length or region 1532, and may include a snaring tool 1540. Expansion suture 1530 may define a lumen along its entire length and therefore in some embodiments, longitudinal passage length 1532 is formed or defined simply by the presence of a snare tool therethrough (described later). In other embodiments, a portion of the expansion suture is provided deformed into a longitudinal passage form (as shown in FIGS. 5A-5C for example) that may hold this longitudinal passage form with or without a snare tool present.

Snaring tool 1540 generally may include a loop end 1542 to receive an end 1532a of the expansion suture. Snaring tool 1540 as provided may weave through and along soft anchor 220, through longitudinal passage length 1532 before extending proximally through and along an opposing side of the anchor 220 and through a portion of insertion instrument 1510. Snaring tool 1540 may have a handle end 1544 that connects to a mechanism incorporated with other portions of a handle portion of insertion instrument 1510 for example (not shown). In other embodiments, snare tool may be a length of suture that extends through the longitudinal passage length 1532 including a bight loop end defining the snaring suture loop configured to capture the expansion suture 1530 suture therethrough. Expansion suture 1530 may be provided interwoven along the soft anchor 220 resulting in two ends 1532a and 1532b extending as provided from a proximal end of anchor 220. Seen best in FIG. 15B, schematically showing a deployed configuration of system 1500, expansion suture defines longitudinal passage length 1532 with two ends 1532a and 1532b extending from opposing ends of longitudinal passage length, both ends 1532a and 1532b extending through walls of the soft anchor 220 towards a proximal end of anchor 220 defining length 1532a-1 and 1532b-1.

With the assembly 1501 still contained within the instrument 1510, end 1532a may be looped around or stitched through tissue 252 defining suture length 1532a-2. End 1532a may then extend through snare loop 1542 and snare handle end 1544 drawn, to draw suture end 1532a over to an opposing side of, along and through the soft anchor 220 1532a-3. Stated otherwise, expansion suture end 1532a may extend from a proximal end of side A of the soft anchor 220, defining a starting point for a first loop of expansion suture end 1532a. Expansion suture end 1532a may engage tissue and extend through a loop end 1542 of snaring tool 1540. Snaring tool 1540 essentially may then draw expansion suture end 1532a in a full loop around and through the soft anchor 220 to return to the proximal end of side A. More specifically snaring tool 1540 may draw expansion suture end 1532a to a proximal end of side B of the soft anchor 220 and along a pathway including along and possible also through the anchor 220 and towards a distal end of anchor 220, through longitudinal passage length 1532 crossing over to side A followed by along the anchor 220 on side A and extending from the proximal end of anchor to form first suture loop. Expansion suture loop may be preferably formed with the assembly 1501 contained within the insertion instrument 1510 and therefore in an elongate configuration. End 1532a of expansion suture 1530 may be drawn further through longitudinal passage portion 1532 to draw tissue 252 towards the anchor 220 while tissue repair assembly 1501 is contained within the insertion instrument 1510 and also before insertion instrument is inserted into a bone tunnel 260. Longitudinal passage length 1532 may be provided in a radially expanded configuration to receive a snare tool and longitudinal passage length may extend across a distal end of soft anchor 220 and orthogonal to the soft anchor longitudinal axis. Longitudinal passage length 1532 may extend across a substantial portion of the soft anchor width or diameter and may have similar options for lengths to control frictional hold between the longitudinal passage length and sutures extending there-along.

The tissue repair system 1500 may then be placed into bone tunnel 260 and some further approximation of the tissue 252 may be preferable at this point before ejecting the assembly 1501 from the insertion instrument 1510. The inventor envisions an additional option including partial deployment of the assembly 1501 or partial retraction of the outer tube to partially expand the suture anchor 220 to further approximate tissue 252. Therefore a first tension may be applied to end 1532a while assembly 1501 is disposed within the insertion instrument 1510, as this limits deformation of the soft anchor 220 and may draw tissue 252 towards soft anchor 220. A second tension may then be applied on the end 1532b (and possibly 1532a) with the soft anchor 220 partially expelled from outer tube 1502 and within the bone tunnel 260 to alter the configuration of the soft anchor 220 to a partially radially expand state and possibly further approximate the tissue 252 towards the bone. Generally, tension on end 1532b may more preferably or more directly radially expand anchor 220, while tension on end 1532a may both draw tissue 252 closer to anchor 220 and contribute to the deployment of anchor 220. A third tension may then be applied with the soft anchor 220 fully expelled from the outer tube 1502, the third higher tension configured to engage the anchor 200 with walls of the tissue tunnel 260 and wedge the tissue repair assembly 1501 within the pre-formed tunnel 260, similar to configuration shown in FIG. 1C. Of note longitudinal passage 532 may still be partially radially expanded. Applying a fourth tension on the expansion suture ends 1532a and 1532b may elongate longitudinal passage portion 1532' to cinch around the first expansion loops further locking the tissue 252 in place. In addition, the fourth tension on the expansion suture 1530 may draw longitudinal passage length 1532' at least partially into a portion of the soft anchor 220'. Each successive tension may be higher relative to the previous tension. Expansion suture ends 1532a and 1532b may be operably coupled to a control in insertion instrument handle (not shown) that may be operable to control the first through fourth tensions on the expansion suture 1530.

FIG. 15B is a schematic of tissue repair assembly 1501 in an anchoring and locked configuration showing the pathway of the expansion suture 1530 to form the suture loop. Tissue repair assembly 1501 is shown with soft anchor 220' in a deployed and expanded configuration. Soft tissue 252 is approximated to the bone tissue; the longitudinal passage portion 1532 is in an elongate and radially reduced (lesser dilated) configuration 1532' to secure the expansion suture loop. Longitudinal passage length 1532' is disposed at a distal-most end of soft anchor 220'. Expansion suture defines longitudinal passage length 1532 with two ends 1532a and 1532b extending from opposing ends of longitudinal passage length, both ends 1532a and 1532b extending through walls of the soft anchor 220' towards a proximal end of anchor 220' defining length 1532a-1 and 1532b-1. 1532a defines a first loop that extends over tissue 252 1532a-2, along and possibly also interwoven through the anchor 220' 1532a-3, through the lumen of the longitudinal passage length 1532a-4 and then along and through anchor 220' to extend from the anchor proximal end 1532a-5. Lengths 1532a-3 and 1532b-1 may extend through the same portion of anchor 220, extending between the same braided portions. Alternatively, 1532a-3 and 1532b-1 may be circumferentially spaced from each other, extending between braided portions that are spaced apart. Lengths 1532a-4 and 1532a-1 may extend through the same portion of anchor 220, extending between the same braided portions. Alternatively, 1532a-1 and 1532a-4 may be circumferentially spaced from each other, extending between braided portions that are spaced apart.

Figure 16A:
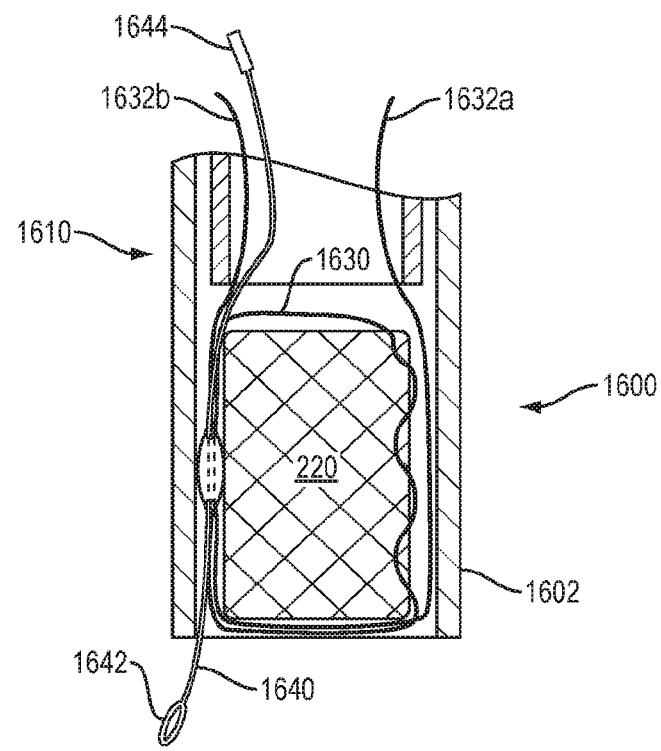
FIG. 16A illustrates an alternative embodiment with a longitudinal passage portion disposed along a sidewall of anchor and before deployment, in accordance with this disclosure.
Figure 16B:
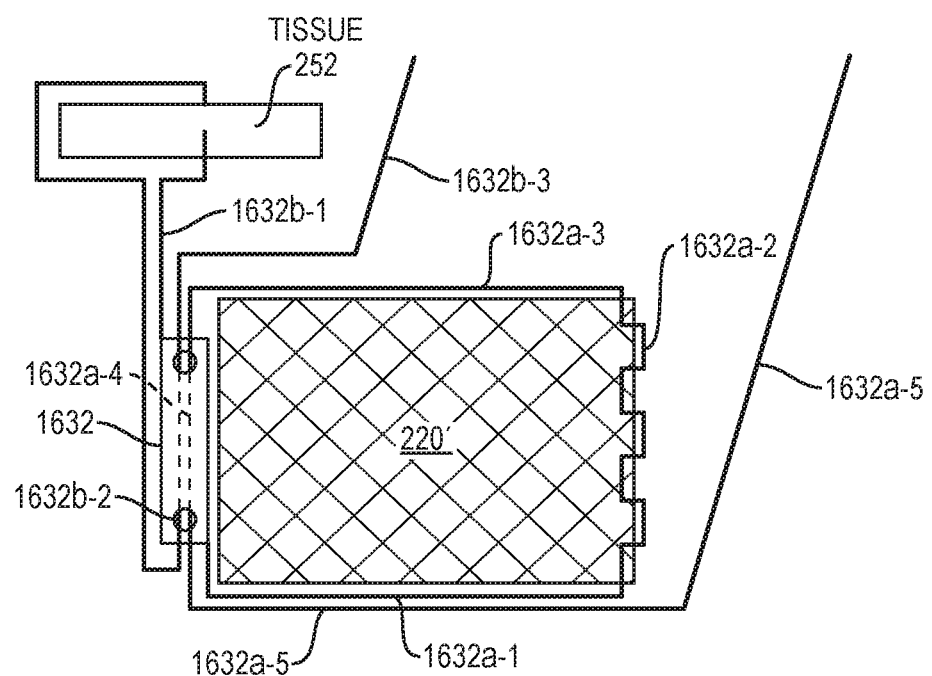
FIG. 16B schematically shows the suture routing of the embodiment shown in the FIG. 16A once deployed, in accordance with this disclosure.

An alternative routing embodiment is shown in FIGS. 16A-16B, illustrating a tissue repair system and a method of use with a continuous loop of expansion suture with both free ends passed through longitudinal passage length disposed on a side of anchor 220 and a single loop around tissue. This may allow a degree of separate emphasis of controls; tension on one suture end preferably configured to radially expand or deploy the anchor 220, and tension on the other suture end preferably configured to approximate the tissue. Shown in FIG. 16A is a distal end portion of a tissue repair system 1600, as provided which may generally include a tissue repair assembly 1601, insertion instrument 1610 and may include one snare tool 1640. Insertion instrument 1610 may be similar to that generally described in U.S. Publication No. 2013/0163810 (Brown et al.), herein incorporated in its entirety by reference. The tissue repair assembly 1601 may include a soft anchor 220 similar to the tissue repair assembly 100 of FIGS. 1A-C. As schematically shown in FIG. 16A, soft anchor 220 may be provided contained within insertion instrument 1610, with an expansion suture 1630 interwoven therethrough. A portion of the expansion suture 1630 may include a longitudinal passage length or region 1632, and may include a snaring tool 1640. Expansion suture 1630 may define a lumen along its entire length and therefore in some embodiments, longitudinal passage length 1632 is formed or defined simply by the presence of a snare tool therethrough (described later). In other embodiments, a portion of the expansion suture is provided deformed into a longitudinal passage form (as shown in FIGS. 5A-5C for example) that may hold this longitudinal passage form with or without a snare tool present.

Snaring tool 1640 may include a loop end 1642 to receive an end 1632b of the expansion suture. Snaring tool 1640 as provided may extend through longitudinal passage length 1632. Snaring tool 1640 may have a handle end 1644 that may connect to a mechanism incorporated with other portions of a handle portion of insertion instrument 1610 for example (not shown). In other embodiments, snare tool may be a length of suture that extends through the longitudinal passage length 1632 including a bight loop end defining the snaring suture loop configured to capture the expansion suture 1630 suture therethrough. Expansion suture 1630 may be provided interwoven along the soft anchor 220 resulting in two ends 1632a and 1632b extending as provided from a proximal end of anchor 220. Seen best in FIG. 16B, schematically showing a deployed configuration of system 1600, expansion suture defines longitudinal passage length 1632 with two ends 1632a and 1632b extending from opposing ends of longitudinal passage length. End 1632a is provided as a first loop, extending around the anchor, including through walls of the soft anchor (1632a-2) over a proximal end of anchor 220 (1632a-3) and through longitudinal passage length 1632 (1632a-4) towards a distal end of anchor 220 and then over a distal end of anchor (1632a-5) before extending proximally (1632a-6).

With assembly 1601 within insertion instrument 1610, suture end 1632b may be coupled to tissue 252 followed by through snare loop 1642 and snare handle end 1644 drawn, to draw suture end 1632a through longitudinal passage length 1632 towards a proximal end of anchor 220. End 1632b of expansion suture 1630 may be drawn further through longitudinal passage portion 1632 to draw tissue 252 towards the anchor 220 while tissue repair assembly 1601 is contained within the insertion instrument 1610 and also before insertion instrument is inserted into a bone tunnel 260. Longitudinal passage length 1632 may be provided in a radially expanded configuration to receive a snare tool and longitudinal passage length may extend along the entire length of soft anchor 220 from the proximal to distal-most end. Longitudinal passage length 1632 may similar options for lengths to control frictional hold between the longitudinal passage length and sutures extending therealong.

The tissue repair system 1600 may be placed into bone tunnel 260 and some further approximation of the tissue 252 may be preferable at this point before ejecting the assembly 1601 from the insertion instrument 1610. Assembly 1601 may then be inserted into the bone tunnel 260 and tension on end 1632a may radially expand and anchor assembly 1601 within bone tunnel 260. The inventor envisions an additional option including partial deployment of the assembly 1601 or partial retraction of the outer tube to partially expand the suture anchor 220 to further approximate tissue 252. Therefore, a first tension may be applied to end 1632b while assembly 1601 is disposed within the insertion instrument 1610, as this limits deformation of the soft anchor 220 and may allow for easier sliding of suture and thereby approximation of tissue to preferentially draw tissue 252 towards soft anchor 220. A second tension may then be applied on the end 1632a (and possibly 1632a) with the soft anchor 220 partially expelled from outer tube 1602 and within the bone tunnel 260 to alter the configuration of the soft anchor 220 to a partially radially expand state and possibly further approximate the tissue 252 towards the bone. Generally, tension on end 1632a may more preferably or more directly radially expand anchor 220, while tension on end 1632b may both draw tissue 252 closer to anchor 220 and contribute to the deployment of anchor 220. A third tension may then be applied with the soft anchor 220 fully expelled from the outer tube 1602, the third higher tension configured to engage the anchor 220 with walls of the tissue tunnel 260 and wedge the tissue repair assembly 1601 within the pre-formed tunnel 260, similar to configuration shown in FIG. 1C. This third tension may also frictionally secure longitudinal passage length 1632 between walls of tunnel 260 and anchor, further securing the assembly 1601 in a locked configuration. Of note longitudinal passage 1632 may still be partially radially expanded. Applying a fourth tension on the expansion suture ends 1632a and 1632b may elongate longitudinal passage portion 1632' to cinch around the first expansion loops further locking the tissue 252 in place. Each successive tension may be higher relative to the previous tension. Expansion suture ends 1632a and 1632b may be operably coupled to a control in insertion instrument handle (not shown) that may be operable to control the first through fourth tensions on the expansion suture 1630.

FIG. 16B is a schematic of tissue repair assembly 1601 in an anchoring and locked configuration showing the pathway of the expansion suture 1630 to form the suture loops. Tissue repair assembly 1601 is shown with soft anchor 220' in a deployed and expanded configuration. Soft tissue 252 is approximated to the bone tissue; the longitudinal passage portion 1632 is in an elongate and radially reduced (lesser dilated) configuration 1632' to secure the expansion suture loop. Longitudinal passage length 1632' is disposed along a side wall of soft anchor 220'. Expansion suture defines longitudinal passage length 1632 with two ends 1632a and 1632b extending from opposing ends of longitudinal passage length. End 1632a wraps around the anchor, including extending across a distal end of anchor 220, interweaving through anchor 1632a-2, over a proximal end of anchor 1632a-3, through longitudinal passage length 1632a-4, back around distal end of anchor 1632a-5 and along the anchor to extend from an anchor proximal end 1632a-6. Suture end 1632b extends through tissue 252 (1632b-1), into a distal end of longitudinal passage length 1632 (1632b-2) and extends proximally through longitudinal passage length and proximally from assembly 1601 (1632b-3).

Figure 17A:
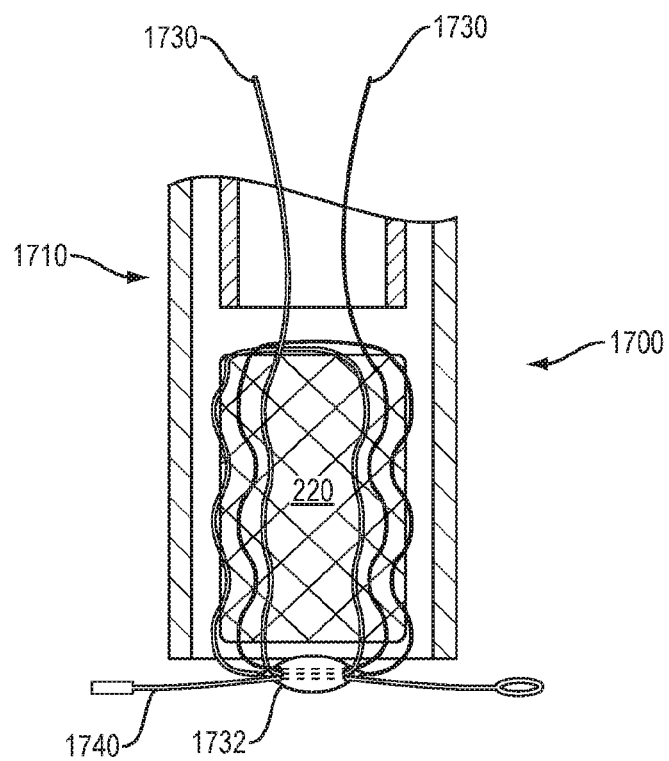
FIG. 17A illustrates an alternative embodiment with a double expansion suture loop and separate repair suture, before deployment in accordance with this disclosure.
Figure 17B:
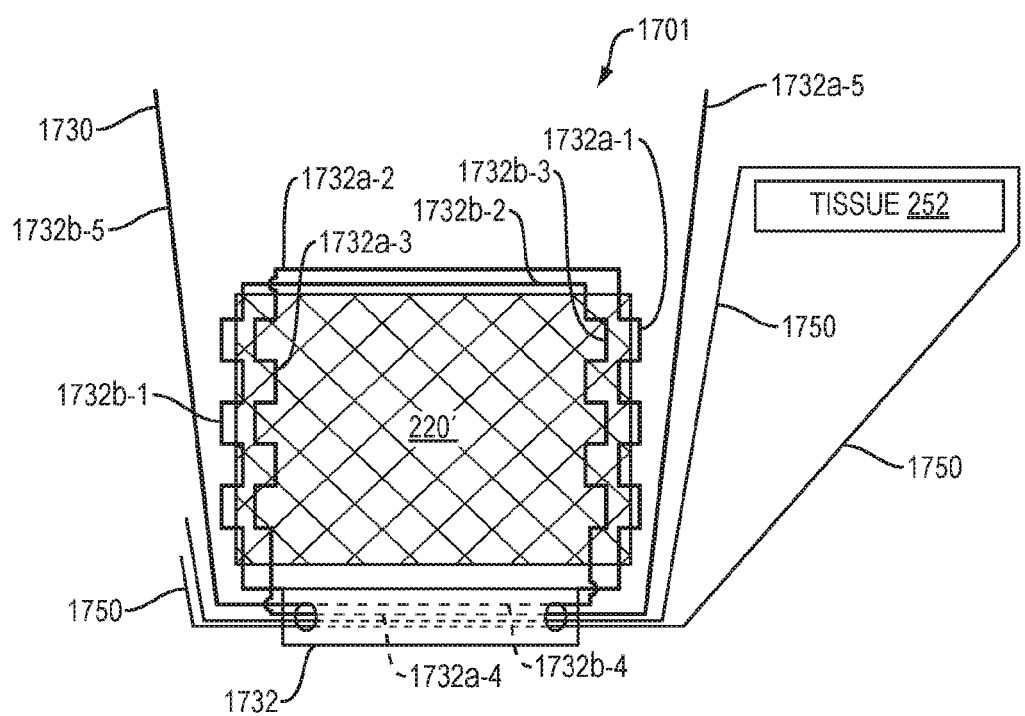
FIG. 17B schematically shows the suture routing of the embodiment shown in the FIG. 17A once deployed, in accordance with this disclosure.

An alternative suture routing embodiment is disclosed in FIGS. 17A and 17B, illustrating a tissue repair system and a method of use, with many similar aspects to those described previously. This embodiment discloses an expansion suture 1730 including a longitudinal passage portion 1732 that is configured to receive at least 3 lengths of suture therethrough, and as shown may receive 4 or 6 lengths of suture therethrough. Similar to previous embodiments shown, anchor may be provided disposed within an insertion instrument 1710. In this embodiment, two expansion suture loops may be pre-routed around and through anchor 220 with a longitudinal passage length 1732 at a distal end of the anchor 220. As shown both loops interweave through and along anchor 220, although in some other embodiments only on portion of each loop may interweave, while other portions may extend along outer portions or anchor 220. A snare tool 1740 may extend through the longitudinal passage length 1732, and may be routed in a similar manner to the embodiment shown in FIG. 2A. In this embodiment, a separate repair suture 1750 may be snared by snaring tool 1740, in a manner similar to the embodiment described in FIG. 2A.

Snaring tool 1740 generally may include a loop end to receive at least one end of the repair suture 1150 and may extend through longitudinal passage length 1752. Snaring tool 1740 may have a handle end or alternatively be connected to a mechanism incorporated with other portions of a handle of insertion instrument (not shown). In other embodiments, snare tool may be a length of suture that extends through the longitudinal passage length 1752 including a bight loop end defining the snaring suture loop configured to capture the repair suture 1750 suture therethrough. Expansion suture 1730 may be provided interwoven along the soft anchor 220 resulting in two ends extending as provided from a proximal end of anchor 220.

FIG. 17B represents a schematic of the tissue repair assembly 1701 in a deployed and knotlessly locked configuration. The inventors envision that the double loop configuration of expansion suture 1730, together with a cinched longitudinal passage portion 1732 may be sufficient to knotlessly lock the assembly 1701. With the assembly 1701 still contained within the instrument, repair suture 1750 may be looped around or stitched through tissue 252. At least one end of repair suture 1750 may then extend through snare 1740.

Longitudinal passage length 1732 may be provided in a radially expanded configuration to receive a snare tool and longitudinal passage length may extend across a distal end of soft anchor 220 and orthogonal to the soft anchor longitudinal axis. In alternative embodiments longitudinal passage length 1732 may extend along a side of anchor 220 or across a proximal end, orthogonal to the soft anchor 220. Longitudinal passage length 1732 may extend across a substantial portion of the soft anchor width or diameter. Longitudinal passage length 1732 includes an entrance opening and exit opening, both openings at the distal end of anchor 220. A longer longitudinal passage length 1732 generally increases friction between the longitudinal passage length and suture loops that extends therethrough. Longitudinal passage length 1732 may therefore be approximately equivalent to a diameter or width of the all-suture anchor 220, or potentially longer to wrap around and extend along the sides of soft anchor 220 for example. Friction may also however be increased by increasing tension on the longitudinal passage length 1732. Therefore, the inventors envision a series of combinations of tension on the expansion suture 1730 and length of longitudinal passage length 1732, whereby the longer the longitudinal passage length 1732, the less tension may be required on the longitudinal passage length in order to secure the system in a locked configuration. Longitudinal passage length 1732 may vary from 1-8 mm, and may preferable between 2-3 mm. The repair suture may be USP #1, OD 0.4-0.499 mm or USP #2, OD 0.5-0.599 mm. The outer diameter of the expansion suture is USP #2, 0.5-0.599 mm The tissue repair system 1700 may then be placed into bone tunnel 260 and some further approximation of the tissue 252 may be preferable at this point before ejecting the assembly 1701 from the insertion instrument 1710. Tension may be applied to ends of repair suture 1750 while assembly 1701 is disposed within the insertion instrument 1710 and insertion instrument is disposed within or along the bone tunnel 260, as this limits deformation of the soft anchor 220 and may draw tissue 252 towards soft anchor 220. The inventor envisions an additional option including partial deployment of the assembly 1701 or partial retraction of the outer tube 1702 to partially expand the suture anchor 220. Tension may then be applied on the ends of expansion suture 1730 with the soft anchor 220 partially expelled from outer tube instrument 1710 and within the bone tunnel 260 to alter the configuration of the soft anchor 220 to a partially radially expand state 220'. Tension may then be re-applied to the repair suture ends 1750 to draw repair suture 1750 through longitudinal passage portion 1732 and further approximate tissue 252, as radially expanding the anchor 220 may induce slack in the repair suture 1750. More tension may then be applied with the soft anchor 220 fully expelled from the instrument 1710, configured to engage the walls of the tissue tunnel 260 and wedge the tissue repair assembly 1701 within the pre-formed tunnel 260, similar to configuration shown in FIG. 1C. Of note longitudinal passage length 1732 may still be partially radially expanded. Applying further tension on the expansion suture ends 1730 may elongate longitudinal passage portion 1732' to cinch around the first and second expansion loops and repair suture 1750 further locking the tissue 252 in place. In addition, this tension on the expansion suture may draw longitudinal passage length 232' at least partially into a portion of the soft anchor 220'. Expansion suture ends 1730 may be operably coupled to a control in insertion instrument handle (not shown) that may be operable to control the first through fourth tensions on the expansion suture 1730. Ends 1730 may then be trimmed, with no further knots or securing means required.

FIG. 17B is a schematic of tissue repair assembly 1701 in an anchored and locked configuration showing the pathway of the expansion suture 1730 to form the two suture loops. Tissue repair assembly 1701 is shown with soft anchor 220' in a deployed and expanded configuration. Soft tissue 252 is approximated to the bone tissue; the longitudinal passage portion 1732 is in an elongate and radially reduced (lesser dilated) configuration 1732' to secure the two expansion suture loops and repair suture 1750. Longitudinal passage length 1732' is disposed at a distal-most end of soft anchor 220'. Expansion suture defines longitudinal passage length 1732 with two ends 1732a and 1732b extending from opposing ends of longitudinal passage length, both ends 1732a and 1732b extending through walls of the soft anchor 220' towards a proximal end of anchor 220' defining length 1732a-1 and 1732b-1. 1732a defines a first loop that extends over tissue 1732a-2, along an external surface of anchor (220') 1732a-3 or interwoven through the anchor 1732a-3, through the lumen of the longitudinal passage length 1732a-4 and then along an external surface of anchor 220' or interwoven therethrough to extend from the anchor proximal end 1732a-5. 1732b defines a second loop that extends over tissue 1732b-2, crossing over 1732a-2, either along an external surface of anchor 220' or interwoven therethough 1732b-3, through the lumen of the longitudinal passage length 1732b-4 and then along an external surface of anchor 220' (or interwoven therethrough) to extend from the anchor proximal end 1732b-5.

Figure 18A:
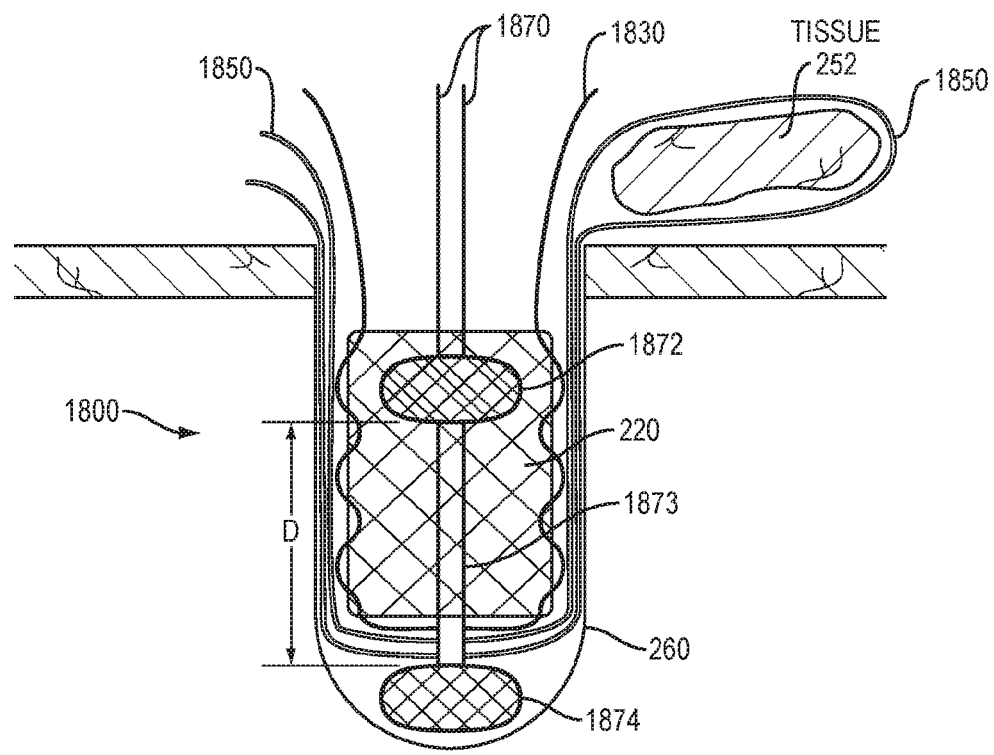
FIGS. 18A and 18B illustrates an alternative embodiment of a tissue repair assembly with an I-lock, before deployment and once deployed, in accordance with this disclosure.
Figure 18B:
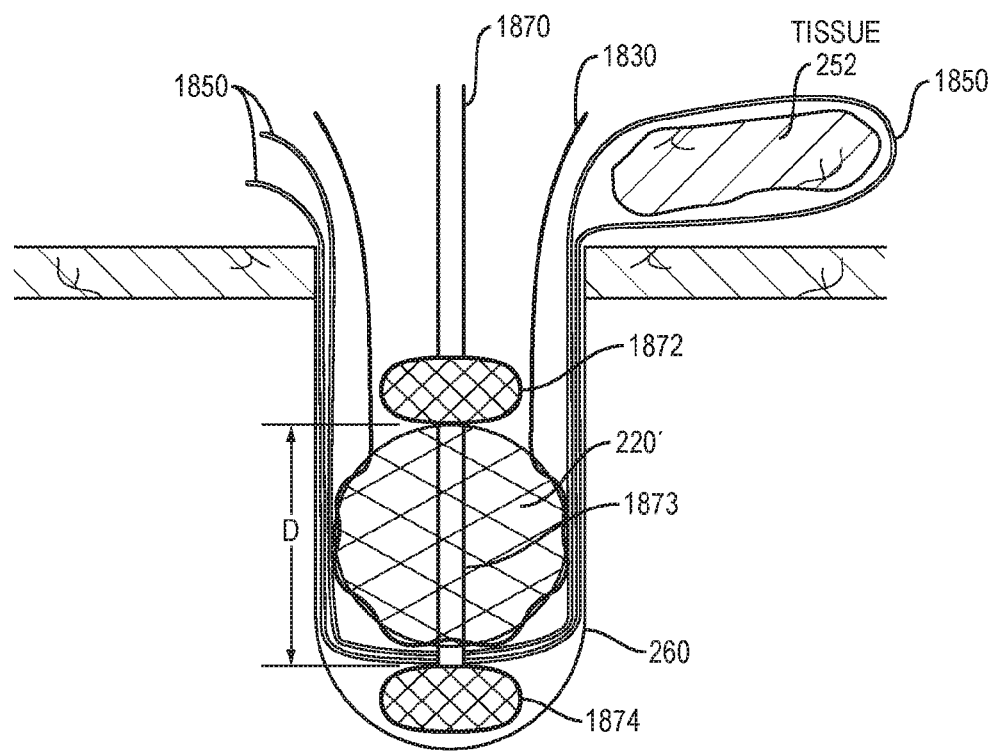

FIGS. 18A and 18B schematically show a further embodiment with an I-lock 1870. Shown is a distal end portion of a tissue repair assembly 1800. Assembly 1800 may be inserted with insertion instrument (not shown) similar to previously shown embodiments. Repair suture 1850 may be routed around external portion of anchor 220 using a snare tool (not shown). The tissue repair assembly 1801 may include a soft anchor 220 and expansion suture 1830 similar to the tissue repair assembly 100 of FIGS. 1A-C, except as described below. A portion of the expansion suture 1830 may include a longitudinal passage length similar to longitudinal passage lengths previously described (not shown in these figures), configured to receive and cinch around repair suture. Alternatively, repair suture 1850 may extend around a distal-most end of anchor 220 and possible through and in-between braids of anchor 220.

Assembly 1800 also includes an I-lock 1870 that may comprise a length of suture having two locking portions 1872 and 1874. Locking portions 1872 and 1874 may be enlarged portions of the I-lock suture 1870, formed by multiple overlapping knots of the suture 1870, or interwoven clusters. As provided a first locking portion 1872 may be disposed within the lumen of anchor 220 and between the proximal-most and distal-most end of anchor 220. Second locking portion 1874 may be disposed external to the anchor 220 at a distal most end. Bridging suture 1873 couples first and second locking portion 1872 and 1874 to maintain a distance "D" between the locking portions. Distance "D" is approximately the length of anchor 220 when anchor is axially reduced to its deployed configuration.

Shown in FIGS. 18A and 18B a repair suture 1850 may be selectively coupled to tissue 252 and then drawn or threaded through longitudinal passage portion (if present) and in-between second locking portion 1874 and distal-most end of anchor 220. Repair suture 1850 may be a similar flexible material to expansion suture 1830, or may be different in braid, material and dimensions. The repair suture 1850 is configured to couple with tissue 252, and preferably be knotlessly secured with anchor 220, between second locking portion 1874 and anchor distal end.

FIG. 18B shows the tissue repair assembly 1800 in a deployed configuration. At least one of the expansion suture ends 1830 has been withdrawn proximally so as to alter the configuration of the soft anchor to a radially expand state 220', configured to engage the walls of the tissue tunnel 260 and wedge the tissue repair assembly 1800 within the pre-formed tunnel 260, similar to configuration shown in FIG. 1C. While deploying assembly 1800, tension on the at least one suture end 1870 maintains distance "D" between the two locking portions. As the soft 220 moves to an axially reduced state, the anchor lumen slides over the first locking portion 1872 and in the deployed configuration first locking portion 1872 is ejected from the anchor 220 and disposed on an outer surface of anchor 220 as shown. First locking portion 1872 is therefore configured to allow the soft anchor lumen to slide over it, and have sufficient cross sectional dimension to inhibit reentry of first locking portion 1874 back into the anchor lumen. Lumen openings at the distal and proximal-most end may shrink during radial expansion, or may be provided with some heat treatment to keep braided ends from wearing, as disclosed in U.S. Publication No. 2013/0123810 (Brown et al.), incorporated by reference herein. Second locking portion 1874 may have an equivalent cross sectional dimension or diameter to first locking portion 1872. Second locking portion 1874 is configured to remain external to the anchor 220 and not enter anchor lumen. In the deployed configuration, the preferred axial length is substantially equivalent to distance "D". Repair suture 1850 may extend along an outer surface portion of soft anchor 220, and thereby be at least partially locked in position between the expanded soft anchor 220' and tunnel wall.

A method of use of the embodiment shown in FIGS. 18A and 18B may include drilling a bone tunnel and passing a repair suture through the torn soft tissue (252). A suture threader or snare may be used to pass repair suture 1850 through a passage of the anchor 220, the passage could be through the I-lock (second portion 1874) or through a longitudinal passage portion of extension suture 1830 or through the anchor 220. Anchor and I-lock is provided enclosed within an outer tube of a delivery device may then be delivered to pre-drilled bone tunnel and the repair suture adjusted to remove slack in the repair. Tension on the expansion suture 1830 may then expand the anchor 220 radially, with concomitant tension on the I-lock proximal end. During anchor expansion, I-lock proximal portion emerges out of anchor lumen and locks the axial length of anchor to maintain deployed state. I-lock keeps the assembly locked in place, maintaining high friction force between the anchor 220, expansion suture 1830 and repair suture 1850, providing the majority of suture sliding strength. Anchoring is provided by deployed anchor 220'.

Figure 19A:
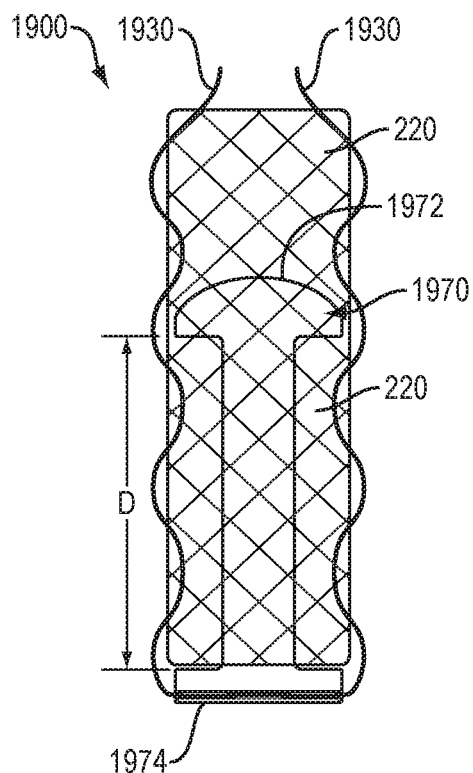
FIGS. 19A-19C illustrates an alternative embodiment with a rigid I-lock, in accordance with this disclosure.
Figure 19B:
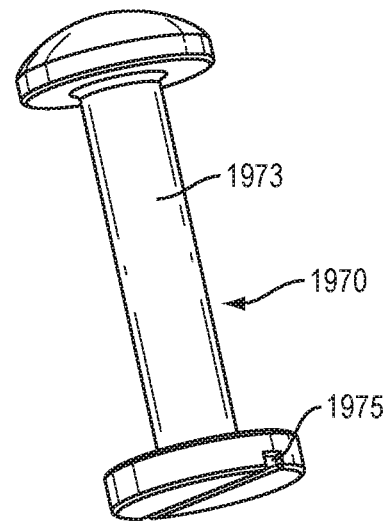
Figure 19C:
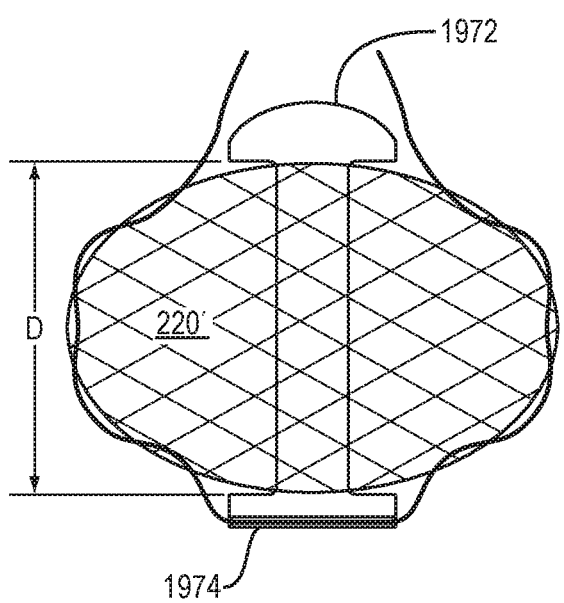

A further embodiment is shown in FIG. 19A-19C, illustrating an embodiment with a more rigid I-lock member 1970 relative to I-lock 1870; the tissue, repair suture and insertion instrument not shown for ease of discussion. Assembly 1900 may be inserted with insertion instrument (not shown) similar to previously shown embodiments.

Repair suture (not shown) may be routed around external portion of anchor 220 using a snare tool (not shown). The tissue repair assembly 1900 may include a soft anchor 220 and expansion suture 1930 similar to the tissue repair assembly 100 of FIGS. 1A-C, except as described below. Assembly 1900 also includes an I-lock 1970 that may comprise a rigid element having two locking portions 1972 and 1974. As provided a first locking portion 1972 may be disposed within the lumen of anchor 220 and between the proximal-most and distal-most end of anchor 220. Second locking portion 1974 may be disposed external to the anchor 220 at a distal most end. Second locking portion 1974 may include a channel 1975 to receive a length of suture such as the expansion suture and/or repair suture. Bridging portion 1973 extends between first and second locking portion 1972 and 1974 to maintain a distance "D" between the locking portions. Distance "D" is approximately the length of anchor 220 when anchor is axially reduced to its deployed configuration.

A repair suture may be selectively coupled to tissue 252 and then drawn or threaded through longitudinal passage portion (if present) and in-between second locking portion 1974 and distal end of anchor 220. Repair suture may be a similar flexible material to expansion suture, or may be different in braid, material and dimensions. A repair suture is configured to couple with tissue 252, and preferably be knotlessly secured with anchor 220, between second locking portion 1974 and anchor distal end, similar to repair suture shown in FIGS. 18A and 18B.

A rigid lock 1970 eliminates the need for tension on the locking member 1970 during deployment to maintain distance "D". FIG. 19C shows a portion of tissue repair assembly 1900 in a deployed configuration. At least one of the expansion suture ends 1930 has been withdrawn proximally so as to alter the configuration of the soft anchor to a radially expand state 220', configured to engage the walls of the tissue tunnel 260 and wedge the tissue repair assembly 1900 within the pre-formed tunnel 260, similar to configuration shown in FIG. 1C. As the soft 220 moves to an axially reduced state, the anchor lumen slides over the first locking portion 1972 and in the deployed configuration first locking portion 1972 is ejected from the anchor 220 and disposed on an outer surface of anchor 220 as shown. First locking portion 1972 is therefore configured to allow the soft anchor lumen to slide over it, and therefore may be tapered. First locking portion 1972 may also have sufficient cross sectional dimension to inhibit reentry of first locking portion 1974 back into the lumen. Lumen openings at the distal and proximal-most end may shrink during radial expansion, or may be provided with some heat treatment to keep braided ends from wearing, as disclosed in U.S. Publication No. 2013/0123810 (Brown et al.), incorporated by reference herein. Second locking portion 1974 may have an equivalent cross sectional dimension or diameter to first locking portion 1972. Second locking portion 1974 is configured to remain external to the anchor 220 and not enter anchor lumen. In the deployed configuration, the preferred axial length is substantially equivalent to distance "D". A repair suture (not shown) may extend along an outer surface portion of soft anchor 220, and through a passage 1975 along a distal end of locking member 1970.

A method of use of the embodiment shown in FIGS. 19A and 19B may include drilling a bone tunnel and passing a repair suture through the torn soft tissue (252). A suture threader or snare may be used to pass repair suture 1950 through a passage 1975 of the locking member 1970 (not shown). Anchor and I-lock may then be delivered to pre-drilled bone tunnel and the repair suture adjusted to remove slack in the repair. Tension on the expansion suture 1930 may then expand the anchor 220 radially. During anchor expansion, I-lock proximal portion may slide out of anchor lumen and lock the axial length of anchor 220 to maintain deployed state. I-lock keeps the assembly locked in place, maintaining high friction force between the anchor 220, expansion suture 1930 and repair suture, providing the majority of suture sliding strength. Anchoring strength is provided by bulged anchor 220'.

Figure 20A:
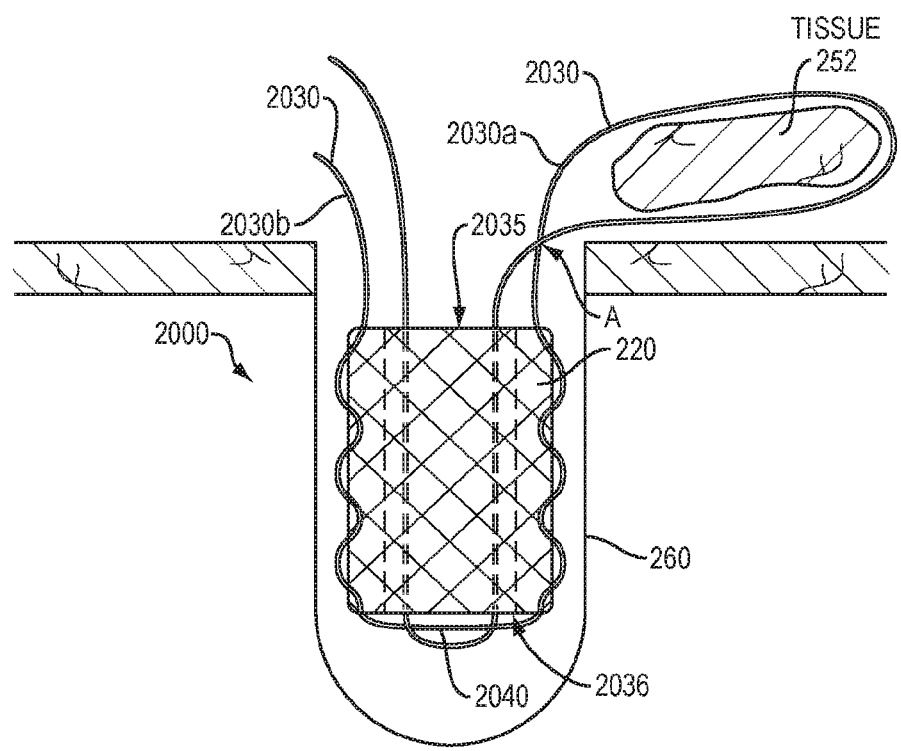
FIGS. 20A-20C illustrates an alternative embodiment of a knotless soft anchor, in accordance with this disclosure.
Figure 20B:
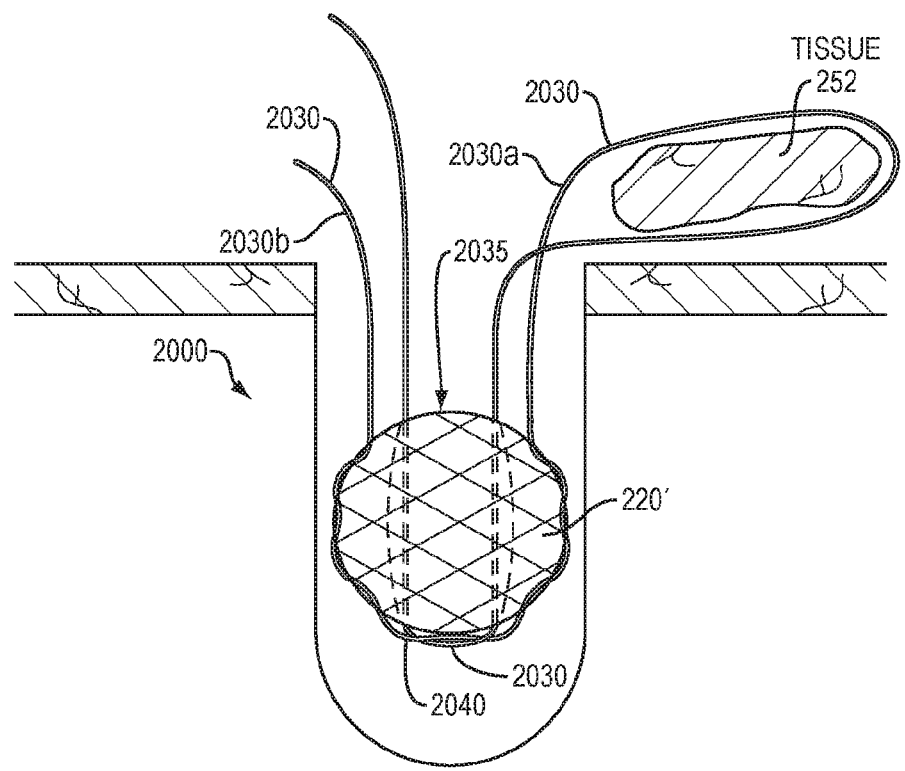

The discussion will now turn to FIGS. 20A-20B, illustrating a tissue repair system and a method of use that may be knotless. Knotless is defined as a system that does not require additional means of locking the anchor assembly within the bone tunnel and retaining the tissue in the desired location such as additional knots, clips or adhesive for example. In this embodiment, the system achieves a knotless state via a sufficiently tortuous path of the expansion suture 2030 through the anchor 220 and over itself at a distal end of anchor in this case. System may include an insertion instrument and snare tool, which is not shown for simplicity. Insertion instrument may be similar to that generally described in U.S. Publication No. 2013/0123810 (Brown et al.), herein incorporated in its entirety by reference. The tissue repair assembly 2000 may include a soft anchor 220 similar to the tissue repair assembly 100 of FIGS. 1A-C, and expansion suture 2030 is interwoven as provided through anchor 220, in a similar manner to that shown and described in FIGS. 1A-1C. Tissue 252 may be coupled to anchor 220 using expansion suture 2030.

FIG. 20B represents the tissue repair assembly 2000 in a deployed and knotlessly locked configuration. A method of repairing a tissue using assembly 200 may include looping at least one expansion suture end 2030a around or stitched through tissue 252, with the assembly 2000 still contained within instrument (not shown). End 2030a may then be threaded through a snare loop of a snare tool, similar to those described earlier. In this embodiment snare tool may extend through open proximal end of anchor lumen 2035 and along said lumen 2035. The lumen walls of the anchor 220 may be defined by extents of the braided threads. Snare tool may route suture end 2030a through anchor 220 in a loop almost entirely contained within the lumen 2035. This loop may exit anchor at the anchor distal end 2036 and loop over a distal-most surface of expansion suture portion 2040 that traverses the anchor distal end 2036, before re-entry into the lumen distal end and along lumen. This may retain the expansion suture loop from simply being pulled out of lumen 2035, and creates an increases tortuous path for the expansion suture and thereby a knotless anchor assembly. End 2030a may extend along lumen 2035 in a proximal direction thereafter and finally extend from proximal end of lumen and adjacent expansion suture end 2030b. The inventor has found that snaring the suture 2030 along a central core or lumen of anchor may be easier to manipulate than some other embodiments where the snare interweaves between braids along the anchor. There is less friction on the snare and less likelihood of getting the snare snagged on the anchor. Tissue approximation may therefore be easier and the whole assembly may be simpler to use.

The tissue repair system 2000 may then be placed into bone tunnel 260 (shown in earlier figures) and some further approximation of the tissue 252 may be preferable at this point before ejecting the assembly 2000 from insertion instrument. Similar to previous embodiments, a first tension may be applied to end 2030b while assembly 2000 is disposed within the insertion instrument and insertion instrument is disposed within or along the bone tunnel 260, as this limits deformation of the soft anchor 220 and may draw tissue 252 towards soft anchor 220. The inventor envisions an additional option including partial deployment of the assembly 2000 to partially expand the suture anchor 220. Tension on expansion suture end 2030b may alter the configuration of the soft anchor 220 to a partially radially expanded state and tension on end 2030a may further approximate tissue 252 while anchor is in the partially radially expanded state. Once fully expelled, tension on the end 2030b may fully deploy anchor 220 to engage or embed within the walls of the tissue tunnel 260 and wedge the tissue repair assembly 2000 within the pre-formed tunnel 260, similar to configuration shown in FIG. 1C and FIG. 20B. Shown in FIG. 20B (and throughout this disclosure) the deployed anchor 220' is shown smaller than bone tunnel 260. This is for ease of viewing the suture paths. In reality, these deployed anchors wedge into and may embed within the bone tunnel softer bone tissue. Applying tension to suture end 2030a may further draw tissue 252 towards anchor 220' and may knotlessly lock assembly 2000 in that it may also draw expansion suture portion 2040 into a distal end of lumen 2035 to form a kink or tight curve along portion 2040. This creates a tortuous path for expansion suture to limit sliding of expansion suture and thereby lock the anchor in the deployed configuration 220' and tissue in place. In alternative methods, the anchor 220 may first be placed into bone tunnel before suture end 2030a is coupled to soft tissue 252. End 2030a may then be drawn through anchor 220 in the loop along the lumen 2035 while anchor is within bone tunnel, and the anchor in an elongate configuration.

Figure 20C:
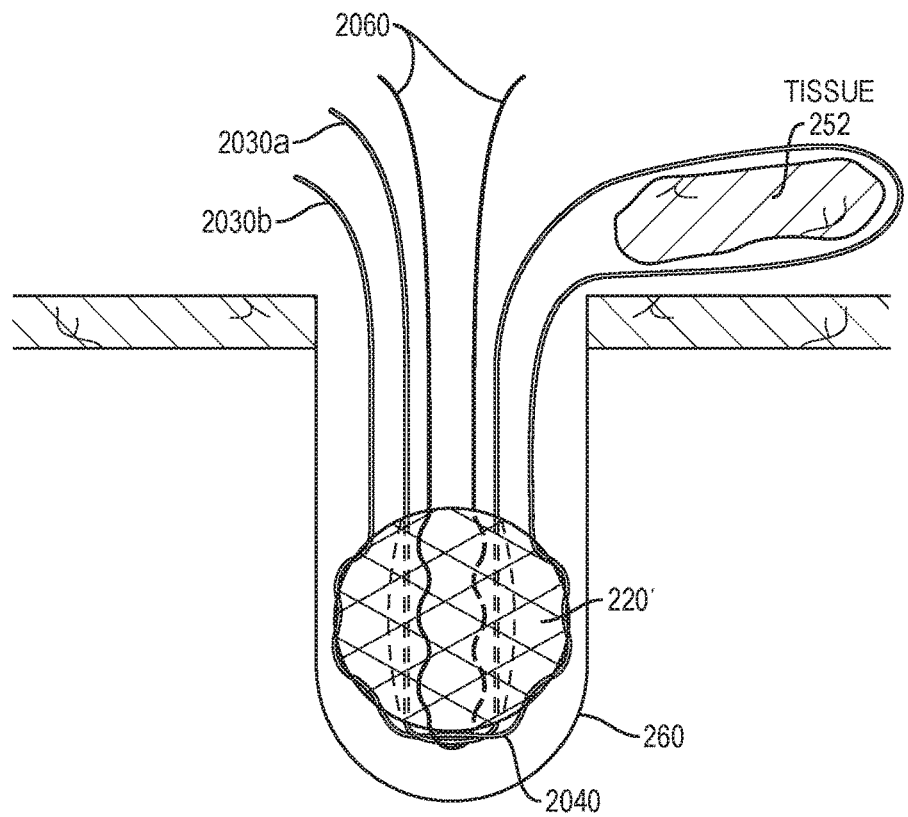

FIG. 20C shows an alternative embodiment to the embodiment shown in FIG. 20A and FIG. 20B, that includes a second suture 2060 that may extend or interweave through anchor 220. In this embodiment, suture 2030 would be operable primarily as a repair suture for approximating tissue and knotlessly locking anchor assembly, while second suture 2060 would be operable primarily as an expansion suture. This may be preferable, as a separate suture to deploy the anchor 220 may help to separate control of the location of the soft tissue 252 from the anchor deployment.

The discussion will now turn to an group of embodiments shown in FIG. 21-24 disclosing various embodiments of a knotless tissue repair system and a method of use, wherein the expansion suture is provided with a pre-formed slip knot configuration, the expansion suture tails extending through a loop of the pre-formed slip knot and at least one loop configured to receive and cinch around the repair suture. Portions of this system may be similar to tissue repair systems such as system 100 and 200 and insertion instrument 210. The tissue repair assembly 2100 may include a soft anchor 220 and expansion suture 2130 similar to the tissue repair assembly 100 of FIGS. 1A-C, except as described below. A portion of the expansion suture 2130 may form a slip knot 2138, comprising at least one loop that is configured to receive both an end 2132a and/or 2132b of the expansion suture 2130 and also a repair suture 2140, the repair suture similar to previously described repair sutures. As shown repair suture 2140 may enter through at least one loop of the slip knot 2138.

Expansion suture 2130 extends through and along the soft anchor 220 and both suture tails 2132a and 2132b extend from a proximal end 222 of soft anchor 220. Each suture tail 2132a and 2132b may interweave through a portion of the soft anchor 220 and also extend along a central inner lumen or core 221 of the anchor 220, such that each tail 2132a and 2132b forms its own looped pathway through and along the anchor 220. More specifically each looped pathway (2133a and 2133b) may include extending from the anchor proximal end 222 to the distal end 224, around the distal end 224 and back towards the proximal end 222. The expansion suture 2130 also forms the slipknot 2138 along a portion of the expansion suture 2130 spaced between the two tails 2132a and 2132b, formed approximately half way along the total suture looped pathway between loop 2133a and 2133b. The slipknot 2138 is disposed at the anchor proximal end 222. Whereas in FIGS. 2A-2D, expansion suture tails 234 and 236 may form a slip knot 238, in this embodiment the knot 2138 is formed along a portion of the expansion suture length spaced away from the tails 2132a and 2132b, both tails 2132a and 2132b and repair suture 2140 extending though at least one loop of the slip knot 2138. Additionally expansion suture 2130 extend from the slipknot 2138 into the anchor 220 and along the loops pathways along and through the anchor 220. Having the slip knot 2138 and thereby means of coupling repair suture 2140 at a proximal end 222 of soft anchor 220 is preferable as tissue tension between the anchor 220 and tissue 252 is maintained as the soft anchor 220 expands and shortens. As the anchor 220 shortens the distal end 224 of anchor 220 tends to move proximally having the potential to reduce tension between the tissue 252 and anchor 220. As the anchor 220 shortens the proximal end of the anchor 220 tends to remain stationary, partly due to the insertion instrument means of deployment, and therefore a repair suture 2140 coupled to a proximal end 222 of anchor 220 tends to retain the tension upon anchor radial expansion and axial contraction.

With repair suture 2140 extended through at least one loop of the slip knot 2138, tension on the expansion suture tails 2132a and 2132b, may reduce the looped pathway length (2133a and 2133b) associated with each tail of the expansion-suture 213 and expand the anchor 220 to engage and anchor with a bone tunnel wall, as described previously. Tension on the expansion suture tails 2138a and 2138b may reduce at least one loop of the slip knot 2138 to cinch around expansion suture tails and repair suture 2140 extending therethrough, and thereby prevent these sutures from sliding. Similar to previous embodiments, this therefore locks the anchor 220 in the radially expanded configuration (220') and also the repair suture 2140 with the anchor 220' and thereby the bone. Knot 2138 may move towards the soft anchor 220. Example sliding knots may include a tautline hitch knot, Duncan loop, Roeder Knot.

Figure 21:
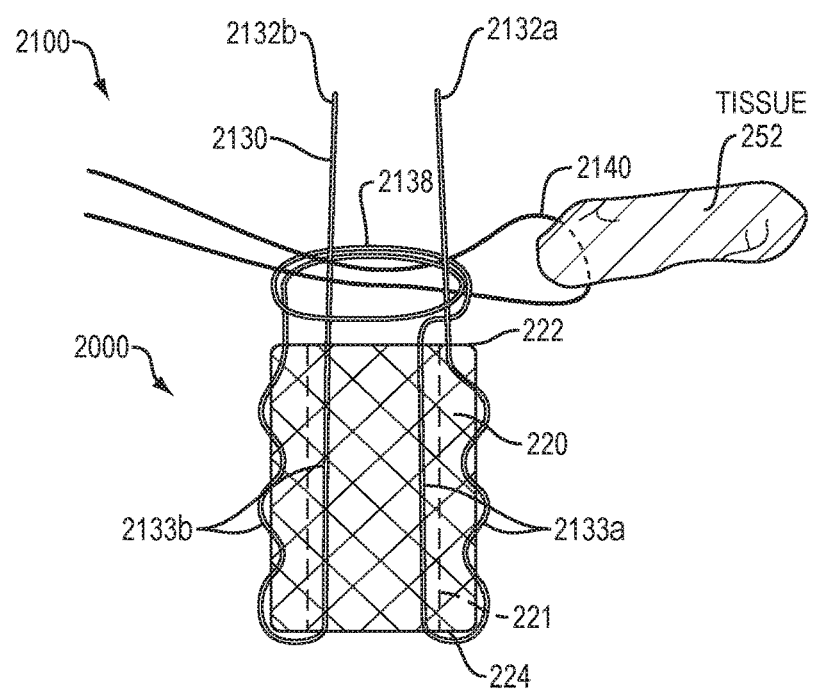
FIG. 21 illustrates an alternative embodiment of suture routing through a soft anchor, in accordance with this disclosure.
Figure 22A:
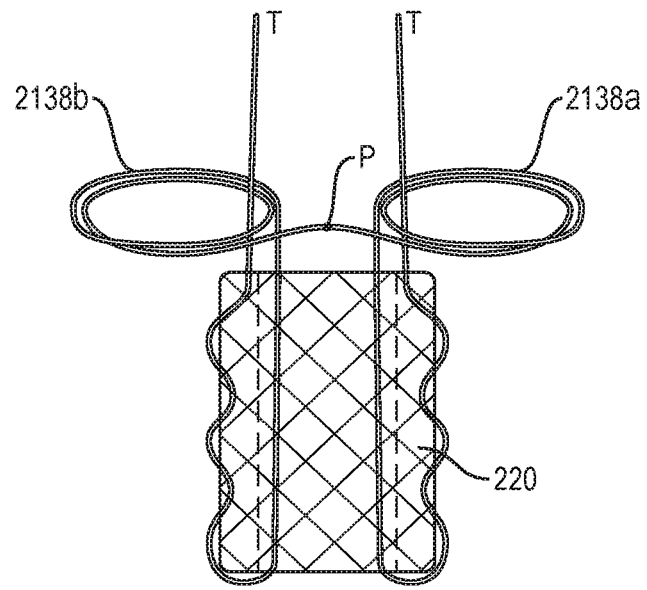
FIGS. 22A-22B illustrates an alternative embodiment of suture routing through a soft anchor, in accordance with this disclosure.
Figure 22B:
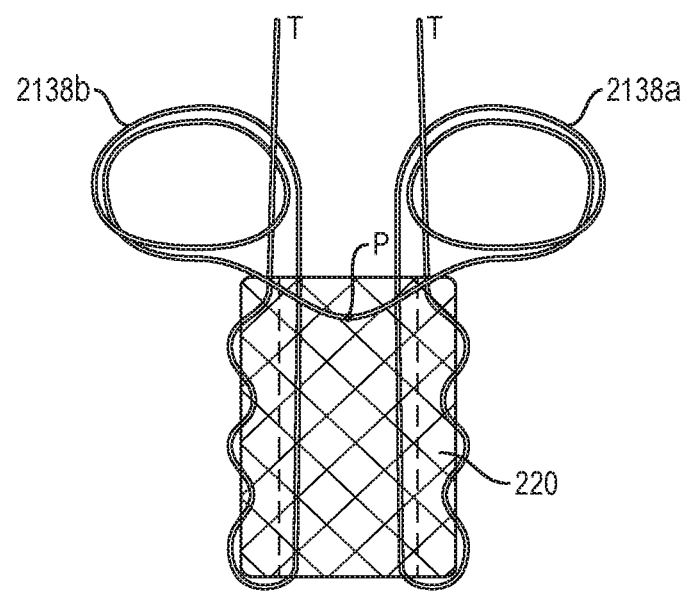

FIG. 21 shows a slipknot 2138 with at least one loop, and may include a plurality of loops substantially concentric with each other with both expansion suture tails 2132a and 2132b therethrough. FIGS. 22A and 22B are alternative slip knot embodiments, including a first slip knot 2138a and a second slip knot 2138b, each slip knot comprising one or more loops and each slip knot having a single expansion suture tail 2132a and 2132b respectively therethough. FIG. 22A shows the slipknots coupled to each other at point P. Point P may be a coupling means such as a knot, or the suture may simply be continuous between the two slipknots 2138a and 2138b. Incorporating two slipknots may reduce the force a single slipknot may need to react by sharing the load. Two knots would also provide a greater percentage of the slipknot being in contact with the expansion and repair sutures thus increasing the friction and reducing suture slip. FIG. 22B shows point P captured with the soft anchor 220, which may better maintain the position of each slipknot relative to the anchor 220 during deployment of the system. While these slip knots 2138 are shown as a plurality of loops, these figures are intended to schematically represent a variety of slip knots known in the art.

Figure 23A:
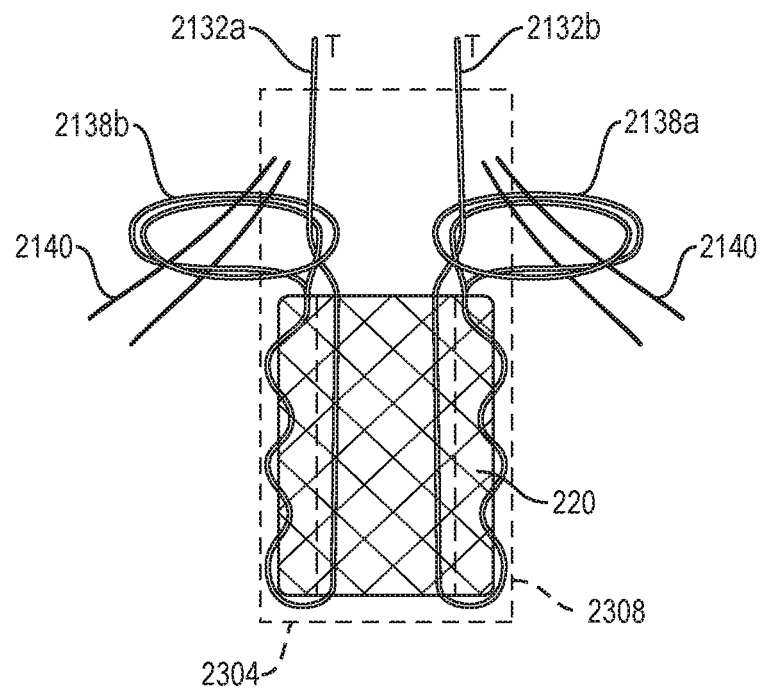
FIGS. 23A and 23B illustrates an alternative embodiment of an insertion instrument distal end configuration for a tissue repair assembly, in accordance with this disclosure.
Figure 23B:
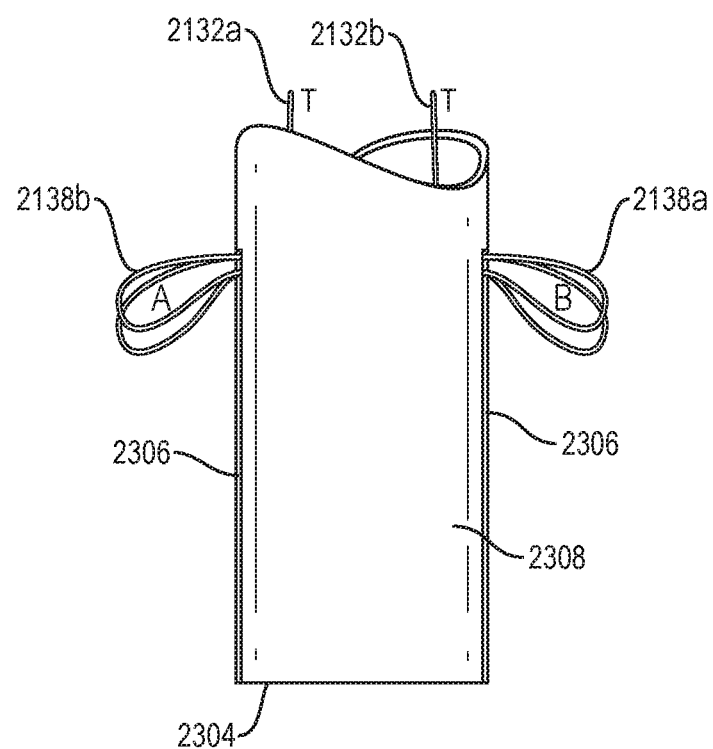

FIGS. 23A and 23B illustrates a tissue repair assembly within an outer tube 2308 of insertion instrument, similar to tube 108 shown and described in FIG. 1B, with the exception of a least one side slot 2306 (two shown), each extending up to and including a distal-most end 2304 of tube 108. These slots 2306 (one on each side) allow either the slip knots 2138a and 2138b to extend therethrough thus allowing the repair suture 2140 direct access to them. Alternatively, these slots may allow a suture snare therethrough, configured to draw the repair suture 2140 into the tube 2308 and through at least one loop of at least one slip knot 2138a/2138b. Expansion suture tails 2132a and 2132b are provided pre-routed through a portion of the slip knots 2138a and 2138b disposed within the insertion tube 2308. Slots 2306 allow the repair sutures to be loaded onto the anchor assembly before the anchor is delivered. Slots 2306 also allow tube 2308 to retract to release the anchor 220 along with the slipknots 2138a and 2138b/repair suture 2140. FIG. 23B shows an exterior, non-sectioned view of FIG. 23A showing slip knots 2138a and 2138b extending through the slots 2306. Expansion suture tails 2132a and 2132b may be provided threaded through slipknots 2138a and 2138b. Once tube 2308 and thereby repair system is disposed within a bone tunnel, tube 2308 may be retracted releasing the anchor 220 along with the slip knots 2138a and 2138b with the expansion suture tails 2132a and 2132b and repair suture 2140 extending therethough.

Figure 24:
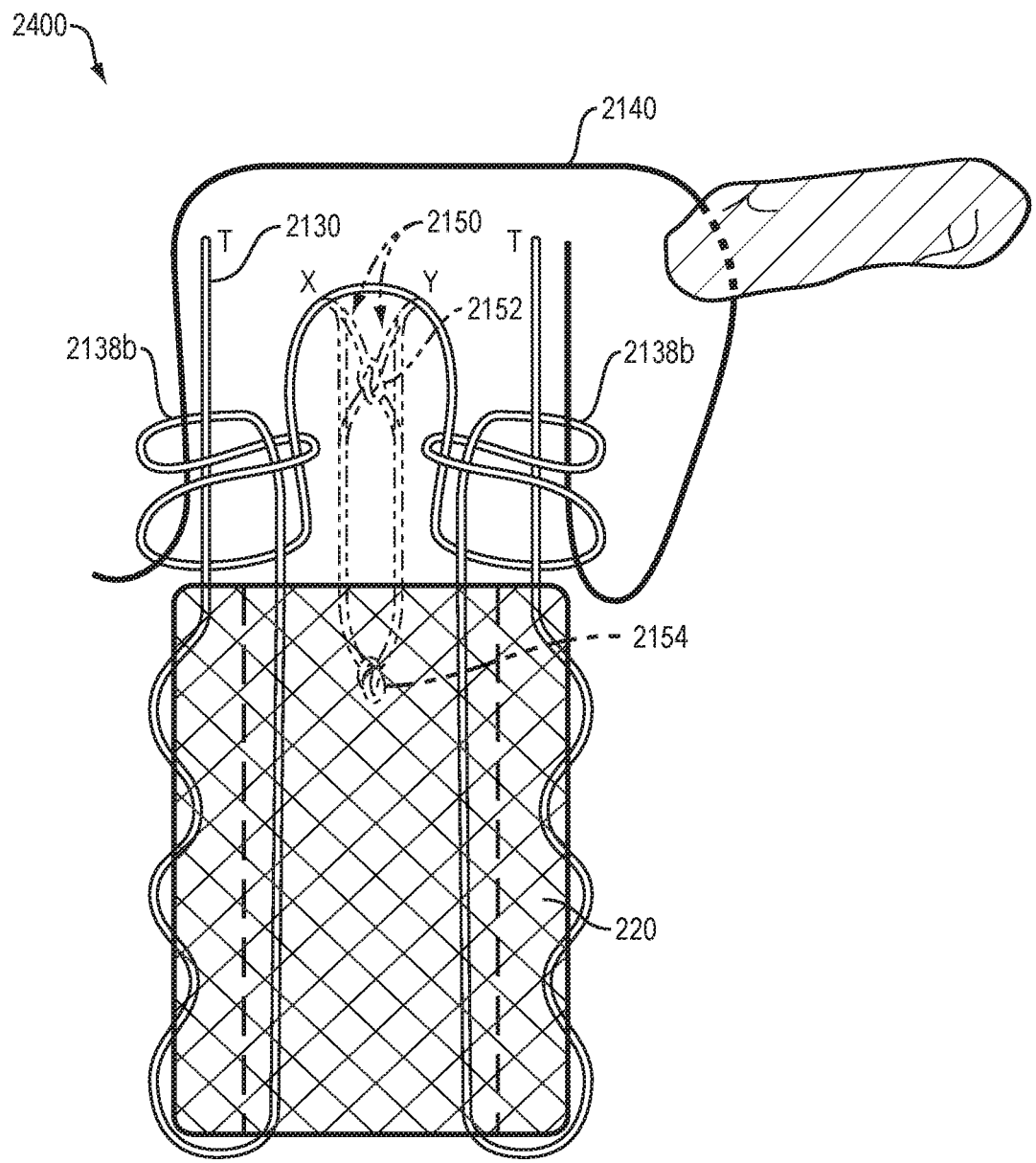
FIG. 24 illustrates an alternative embodiment of a suture routing for a tissue repair assembly, in accordance with this disclosure.

FIG. 24 shows a further embodiment including a series of alternative routings of slipknots 2138a and 2138b and a second suture construct 2150. Expansion suture 2130 may then extend between the two slipknots 2138a and 2138b and second construct 2150 is configured to center the slipknots 2138a and 2138b. Second suture construct 2150 is coupled to expansion suture 2130 at point X and Y and forms a knot 2152 external to the anchor 220 to center slipknots 2138a and 2138b. Alternatively, or additionally, second suture construct 2150 may include a second knot 2154 or Chinese finger cinch that resides within the anchor 220 to center slipknots 2138a and 2138b. Alternative routes for the repair suture 2140 are also shown in FIG. 24, including extending through a slip knot from a proximal end to a distal end such as that shown through skip knot 2138a and then making a U-turn vs extending from a distal end to a proximal end, as shown through slip knot 2138b, making the U-turn before entering the slipknot. This may increase the tortuous path between the sutures thereby improve the lock on the system and resistance to any loosening of the grip on the repair suture.

A method of repairing tissue including system 2100 or system 2400 for example may therefore start with system such as system 2100 or 2400 and threading a repair suture 2140 through at least one loop of a slip knot 2138, placing the system into a bone tunnel and expelling the anchor 220 from the instrument, the instrument having at least one elongate slot 2306 configured to slidingly receive at least one loop of the slip knot therethrough and allow the at least one loop to slide distally along the slot 2306, and release from the slot 2306. Tension on ends of repair suture 2140 may then be applied to approximate the tissue 252 towards the bone. Tension (T) on ends of expansion suture 2130 may then be applied to radially expand anchor 220 and anchor the system 2100 within the tunnel. Expansion suture ends 2130 may be operably coupled to a control in insertion instrument handle (not shown) that may control the applied tension. Expansion suture ends 2132a and 2132b may be incorporated into a handle of the system that may be a rotatable handle and that may initially retract the expansion suture 2130 at high speed then step down to a lower "gear" with higher mechanical advantage for the final anchor expansion. This "step down" could be based on tension or suture length. An integral knife (not shown) to the instrument may be incorporated into the delivery system such that the expansion suture 2130 or expansion and repair sutures 2140 may be cut upon reaching proper expansion tension. After deployment, the slipknot(s) may still reside at or below the bone surface. The instrument tubing diameter may be reduced in the region of the slipknot(s) to minimize insertion resistance.

Embodiments disclosed in FIGS. 25-31 generally describe a knotless tissue repair system 2600 including a Nail knot or Strangle knot. The Nail knot is preferable staged towards a proximal side of the soft anchor, although in alternative embodiments the Nail knot may be staged distally or within the soft anchor. Having the Nail knot proximally located may allow for a more consistent tension on the repair suture and thereby the soft tissue. A proximal location may also allow a staggered deployment in that the anchor may be deployed independently from the soft tissue adjustment. The Nail knot may in its final state, envelop both limbs of the expansion suture and both ends of repair suture through its center. The repair suture loop extending through tissue to the knotless anchor is ultimately reduced and locked via the cinching action of the Nail knot construct to secure the repair.

Figure 25A:
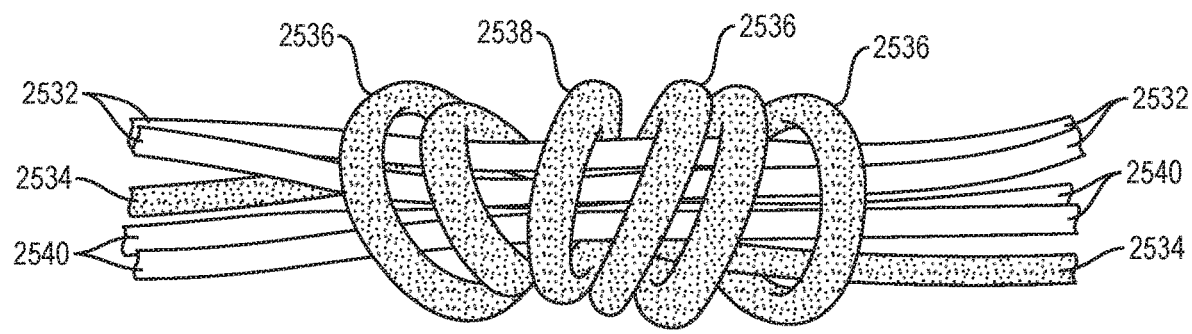
FIGS. 25A-25B illustrates a nail knot wrapped round a repair suture and an expansion suture, in a loose and a cinched configuration respectively.
Figure 25B:
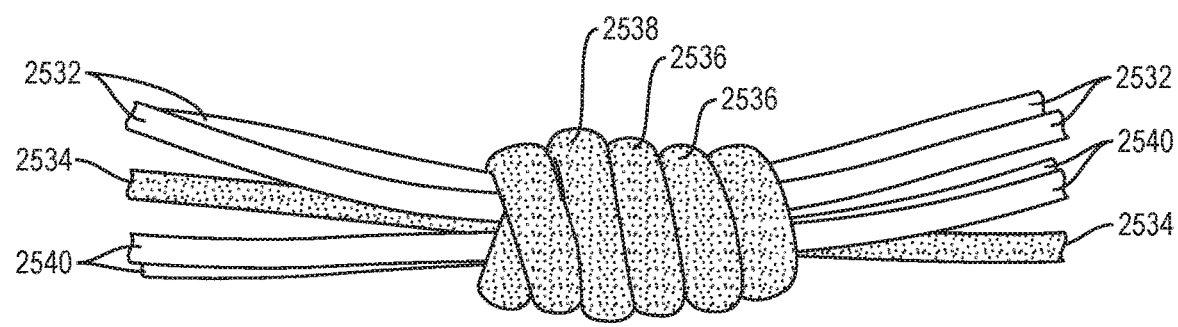
Figure 26A:
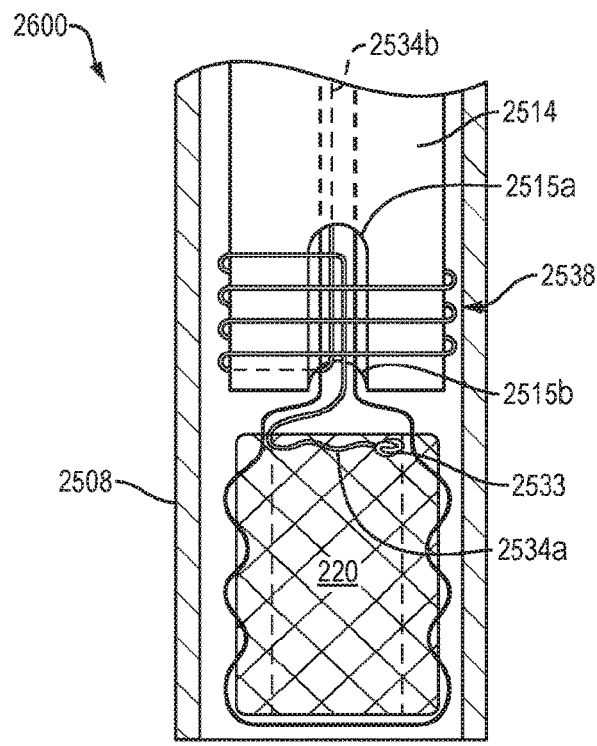
FIG. 26A illustrates an embodiment of a knotless suture system with a nail knot arranged around a portion of the insertion tube, in accordance with this disclosure.
Figure 26B:
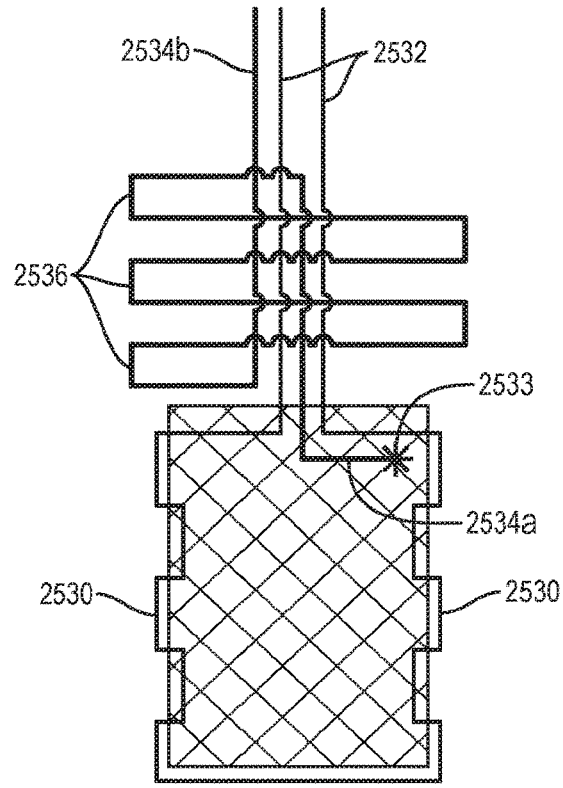
FIG. 26B schematically represents a tissue repair system that is knotless with a suture and nail knot routing of FIG. 26A (insertion tube removed for clarity), in accordance with this disclosure.

Nail knot is schematically shown in FIGS. 25A and 25B, with two limbs of the expansion suture 2532 therethrough and also two limbs of the repair suture 2540. In some embodiments only one limb of each of the repair suture 2540 and expansion suture 2532 may extend through the Nail knot 2538. A nail knot is a radially compressive binding knot comprised of a series of adjacent wraps 2536 derived from a strangle knot configuration that may vary in quantity depending on the compressive force required to prevent suture slide within. The wraps 2536 are cinched around the repair and expansion sutures by pulling axially on at least one of the limbs and preferably both opposing limbs 2534 of the Nail knot 2538. One free limb 2534 may extend from a first end of the column of wraps while the other may extend in a second opposing direction. For example a first free limb 2534a may extend from a proximal end of the column of wraps (see FIG. 26A) distally through the center of the column of wraps and out of a distal end of the Nail Knot 2538 and may be threaded with and thereby coupled to the soft anchor 220. The other free limb 2534b may extend from a distal end of the column of wraps in a proximal direction through the center of the column of wraps and proximally extend from a proximal end of the column of wraps and through insertion instrument, as shown in FIGS. 26A and 26B. Optionally or additionally, the distal most wrap 2534 of the Nail knot 2538 may be stitched through the soft anchor 220, which ensures that the Nail knot 2538 cinches, and stays abutted to the soft anchor 220 during tensioning. Having the Nail knot 2538 directly coupled to the soft anchor 220 is preferable, to keep the Nail knot 2538 adjacent the anchor 220 so that the deployed configuration remains beneath the bone surface when finished. Having a knot protrude from the external bone surface may irritate local tissue.

The proximal limb 2534b of the Nail knot 2538 can be either routed through the insertion tube and handle (see FIG. 26A) and coupled to a tensioning mechanism, or proximally on the outside of the handle. The force to tighten the Nail knot 2538 may be via tensioning the proximal free limb and may be delivered directly either by hand or by the mechanisms within the handle. Assistance of a knot pusher integrated with the shaft (see FIG. 27C) may be required to approximate the Nail knot 2538, so that it adjoins the soft anchor 220 that is deployed within the bone tunnel, and ideally, the Nail knot 2538 remains about 2 mm sub-flush to the bone surface.

FIG. 26A illustrates an insertion instrument distal end, similar to that shown in FIG. 1B, with the outer tube 2508 and all suture anchor 220 disposed therein. Repair suture is not shown in FIG. 26A or FIG. 26B. Expansion suture 2530 may be provided threaded through anchor 220 in a similar fashion to that shown and disclosed in FIG. 1B. Push tube 2514 may operate similar to push tube 114 in FIG. 1B, with the exception that it has a plurality of wraps of a Nail Knot 2538 arranged around an external surface of push tube 2514. Nail Knot first limb 2534a may be coupled to a proximal end of soft anchor 220 and may terminate with a knot 2533 or fixation means, configured to fix first limb 2534a with anchor 220. As shown, first limb 2534a may interweave circumferentially around soft anchor proximal end. In an alternative embodiment, at least one of the loops of wraps of the Nail Knot may loop through a portion of the soft anchor. Second limb 2534b extends proximally and may extend along push tube inner lumen. Second limb 2534b may be operatively coupled to a tensioning mechanism at a proximal end of instrument (not shown). Furthermore distal end of the push tube 2514 comprises a first slot 2515a on a first side of tube 2514 and may extend 4-5 mm proximally. Length of first slot 2515a is configured such that a proximal-most end of first slot 2515a coincides with a preferred proximal end of Nail knot 2538. Second slot 2515b is circumferentially spaced away from first slot 2515a and may be diametrically opposite first slot 2515a. Second slot 2515b may be significantly shorter than first slot 2515a, and is configured to provide a suture channel to limit motion of Nail knot second limb 2534b, and allow second limb 2534b to slide therethrough. Second slot terminates axially more distal than the first slot 2515a, the axial separation between the two slot terminal ends staging the wraps of the nail knot in the correct location. Second slot 2515b may be for example 1-2 mm long, measured along longitudinal axis of tube 2514. Together, the opposing slots form a shallow set of "tines" at the tube tip, which provides a pathway to string a proper Nail knot. In this embodiment, the Nail knot 2538 pathway is as follows (best seen in schematics in FIG. 26B); the first limb 2534a is coupled to soft anchor 220, and may extend circumferentially and interweave with anchor 220 before extending into and through lumen of push tube, and thereby through the core of plurality of nail knot wraps 2536 (column). At proximal end of plurality of nail knot wraps 2536 nail knot suture extends out of first slot 2515a, which may be a proximal-most end of slot 2515a and proceed to form the plurality of serially formed wraps 2536 around the outer circumferential surface of push tube 2514. Once the desired amount of wraps 2536 are formed, the Nail knot pathway extends through second slot 2515b and into the lumen of push tube 2514 and extends proximally through core of plurality of wraps 2536, before operatively coupling to a portion of instrument such as the handle (not shown). Wraps 2536 are shown wrapped around the left "tine" and clockwise, and proceeding with consecutive clockwise wraps, around the circumference of the push tube 2514. The short slot 2515b may help to maintain the column strength of the thin-walled push tube 2514, as it must withstand the force to deploy the anchor 220.

Figure 27A:
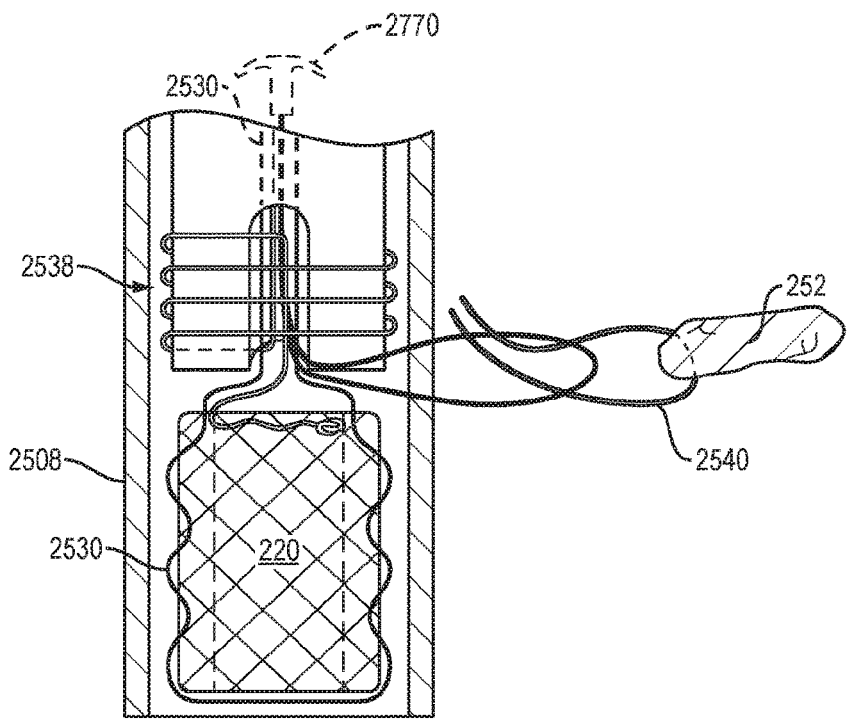
FIGS. 27A-27D illustrates a tissue repair system as shown in FIGS. 26A and 26B and method of threading a repair suture through a system including a nail knot, in accordance with this disclosure.
Figure 27B:
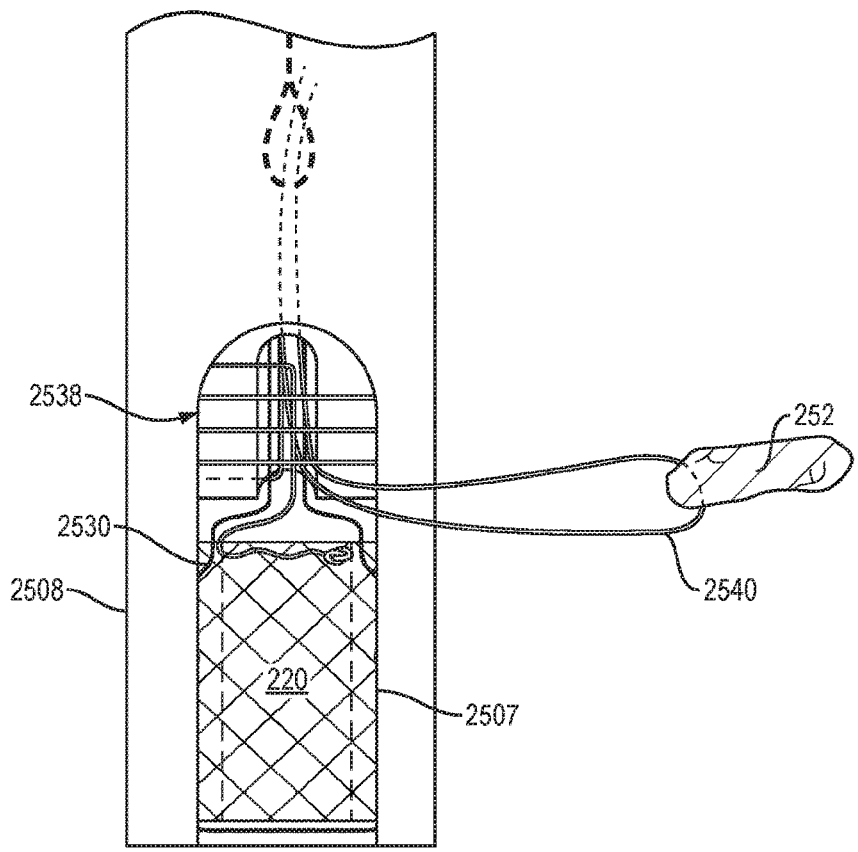
Figure 27C:
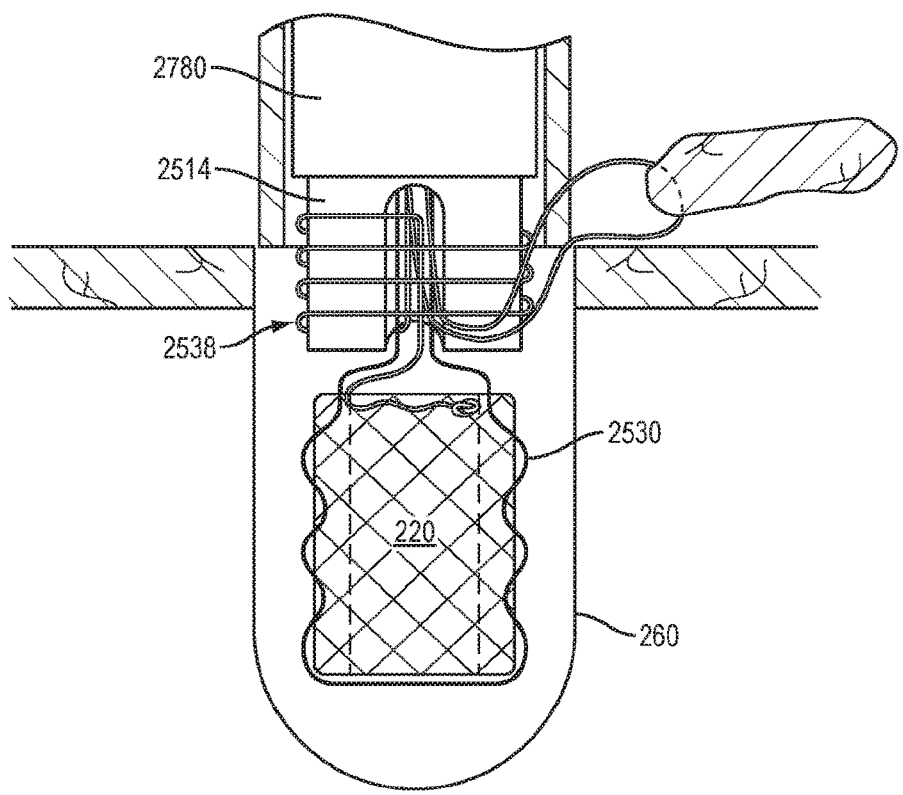
Figure 27D:
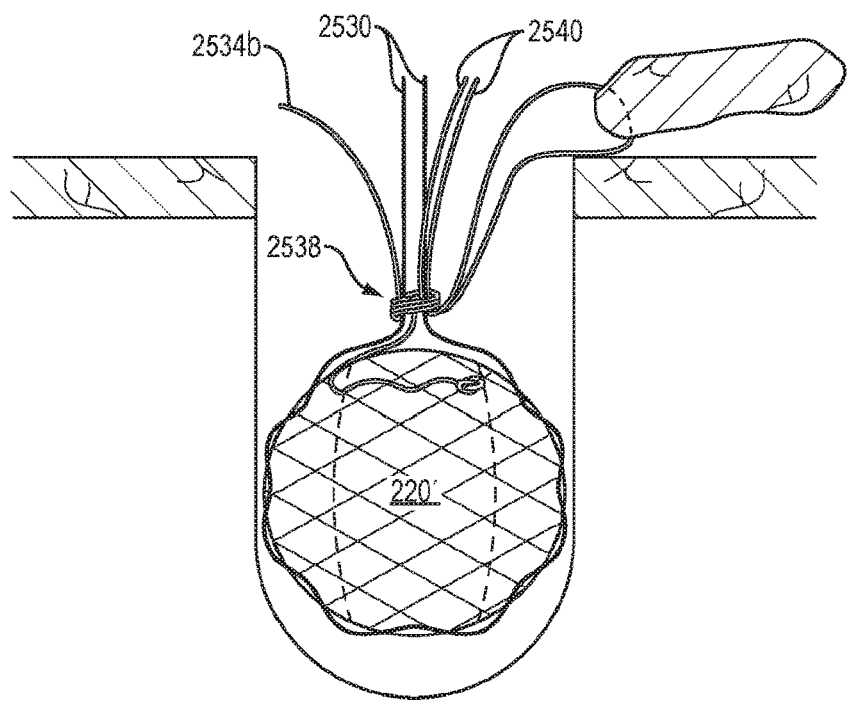

Additionally, the first slot 2515a may allow a pathway for a suture threader (2770) or snare wire to pass through, as shown in FIG. 27A, and ensures the inserter instrument can be disengaged from the anchor/knot construct when removed from the body. Similarly the outer shaft 2508 contains a slot (seen in FIG. 27B) spanning the length of the anchor 220 and Nail Knot 2538, to facilitate the pass-through of the suture threader 2770 and disengagement of the inserter instrument from the anchor/knot construct when removed from the body.

A method of tissue repair is represented in FIG. 27A-27. The method may therefore start with coupling a repair suture 2540 to tissue 252 and threading repair suture 2540 through a nail knot wrapped around an insertion instrument shaft. Threading may include extending the repair suture 2540 through a suture snare 2770. The suture snare 2770 may extend through an aperture or slot of insertion instrument and may extend through at least one wrap of a Nail knot 2538 such that drawing on the snare 2770 threads the repair suture 2540 though at least one wrap of a Nail knot 2538. In some embodiments, the snare may weave in and out of a plurality of wraps such that drawing on the snare 2770 weaves the repair suture 2540 under and over the plurality of wraps of the nail knot 2538 to create a more tortuous path. Drawing on the snare 2770 may further thread the repair suture 2540 through and along a lumen of the insertion instrument and may couple the repair suture 2540 to a tensioning means associated with the insertion instrument (not shown). Repair suture 2540 may be drawn along the Nail knot 2538 while the insertion instrument is placed within a prepared bone tunnel, or beforehand. The insertion instrument may include an elongate slot 2507 on the outer tube 2508 of the instrument, the outer tube 2508 housing a soft anchor 220 operatively coupled to the Nail knot 2538. Outer tube 2508 may be placed within bone tunnel 260 and withdrawn to expel the anchor 220 from the instrument, the elongate slot 2507 configured to allow release of outer tube from repair suture 2540 extending therethough. Repair suture 2540 may also extend through a lumen of inner tube 2514, and thereby extend through either slot 2515a or 2515b of inner tube 2515. Tension on ends of repair suture 2540 may then be applied to approximate the tissue 252 towards the bone 260. Tension on ends of expansion suture 2530 may then be applied to radially expand anchor 220 and anchor the system 2600 within the bone tunnel, as shown in FIG. 27D. Expansion suture ends 2530 may be operably coupled to a control in insertion instrument handle (not shown) that may control the applied tension. Expansion suture ends may be incorporated into the handle of the system that may be a rotational handle. Handle may be initially operated to retract the expansion suture 2530 at high speed, then step down to a lower "gear" with higher mechanical advantage for the final anchor expansion. This "step down" could be based on tension or suture length. An integral knot pusher 2780 coaxially disposed around inner tube 2514 may slide distally and push nail knot 2538 from inner tube 2515 either after anchor 220 has been deployed or concomitant with deployment. Tension on proximal limb 2534b of nail knot 2538 with simultaneous actuation of knot pusher 2780 may tighten nail knot 2538, and cinch the plurality of wraps 2536 around expansion suture 2530 and repair suture 2540. An integral knife (not shown) may be incorporated into the delivery system such that the expansion suture 2530 or expansion and repair sutures 2540 would be trimmed upon reaching proper expansion tension. After deployment, the Nail knot 2538 may preferably reside at or below the bone surface, as shown in FIG. 27D.

In an alternative embodiment, shown in FIG. 28A-28F, Nail knot 2538 may be wrapped around the outer shaft similar to tube 108 in FIG. 1B, except that this outer shaft 2808 includes an elongate slot 2814 cut out through one or both sides. This slot 2814 allows a suture passer 2870 or snare to pull the repair suture 2840 through at least one wrap of the nail knot 2538, while still allowing the push tube to eject from the anchor 220. If the slot 2814 were a 'hole' that was proximal to the anchor 220, there would be a bridge of tubing that prevented the distal end of the inserter (distal to the nail knot) from being removed from the tissue. One could however envision a scenario where the tube 2808 is slotted on one side, but has a through hole 2815 on the other side of the tubing which would still allow repair suture 2540 to be passed through the slot 2814 on the first side, through the nail knot 2538, and through the through hole 2815 on the back side of the tubing. This is shown in FIG. 29.

Figure 28A:
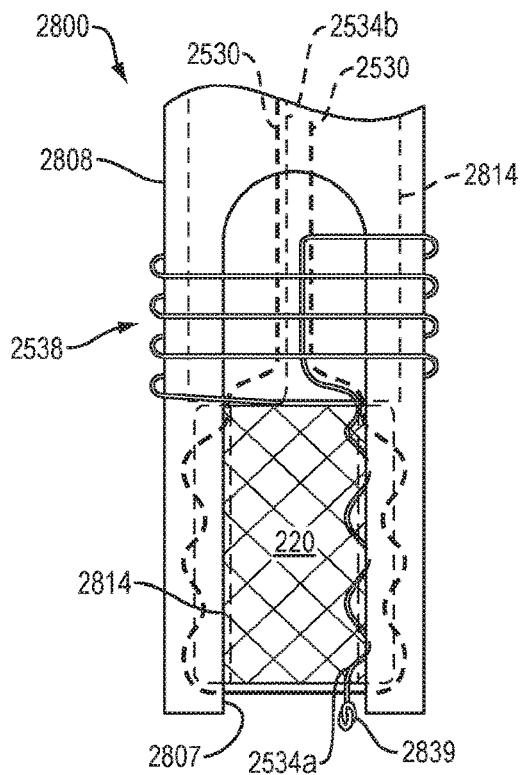
FIGS. 28A-28F illustrates a tissue repair system and method of knotlessly coupling soft tissue to the tissue repair system with a nail knot and thereby a portion of bone, in accordance with this disclosure.
Figure 28B:
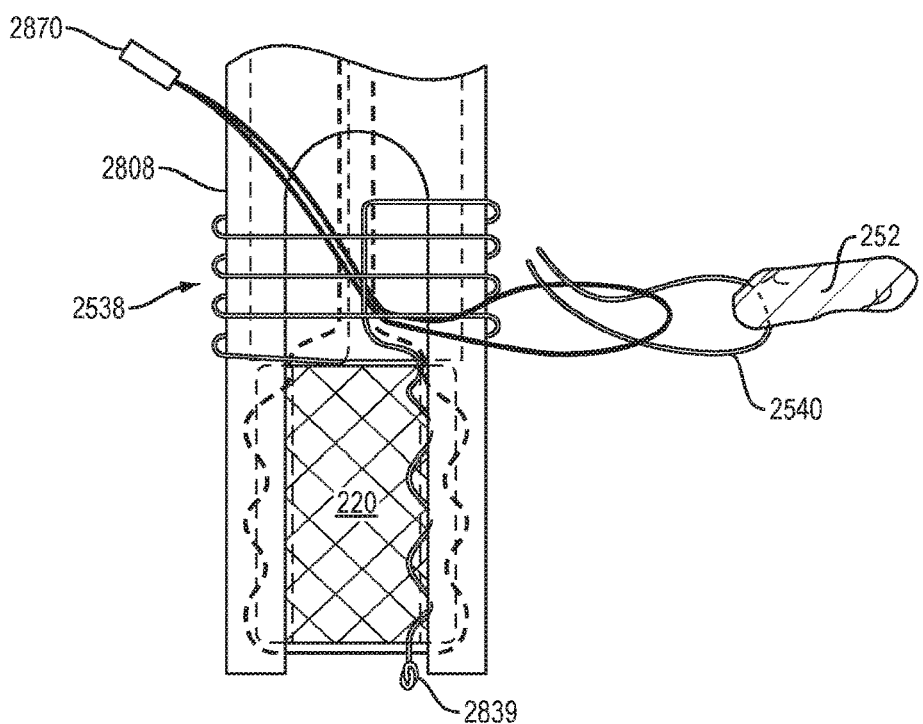
Figure 28C:
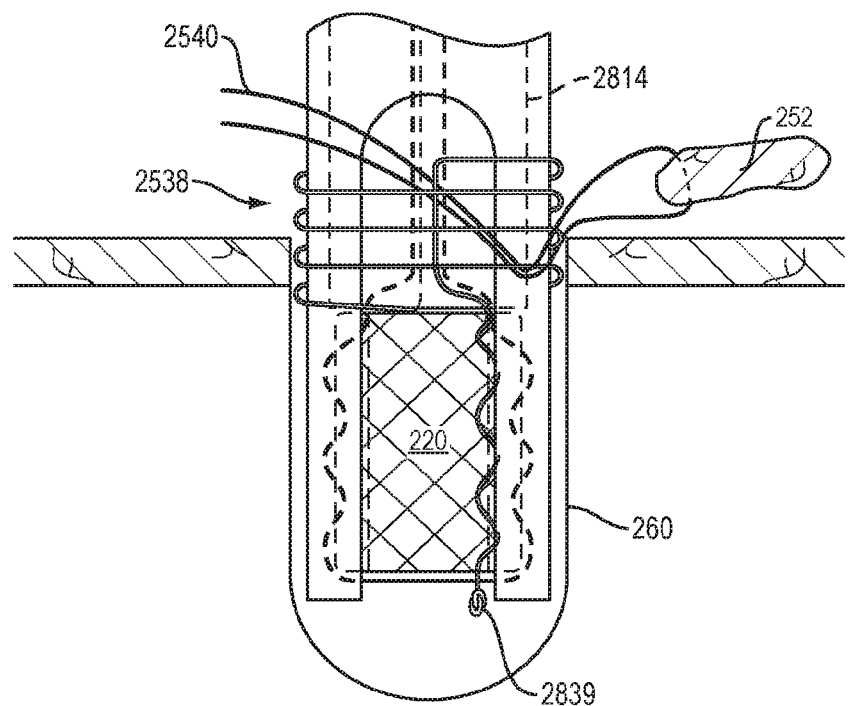
Figure 28D:
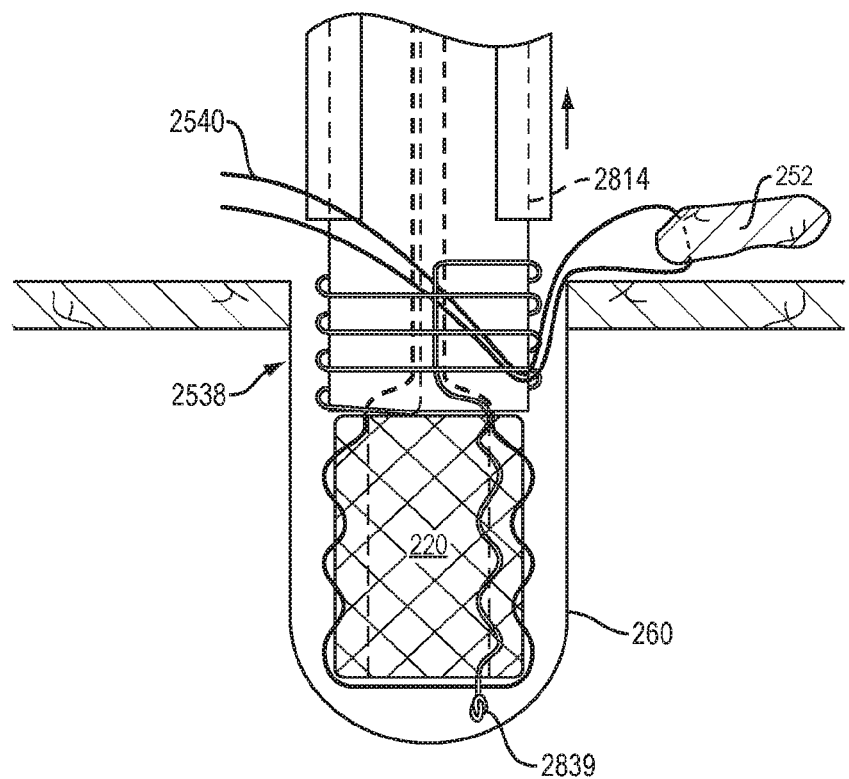
Figure 28E:
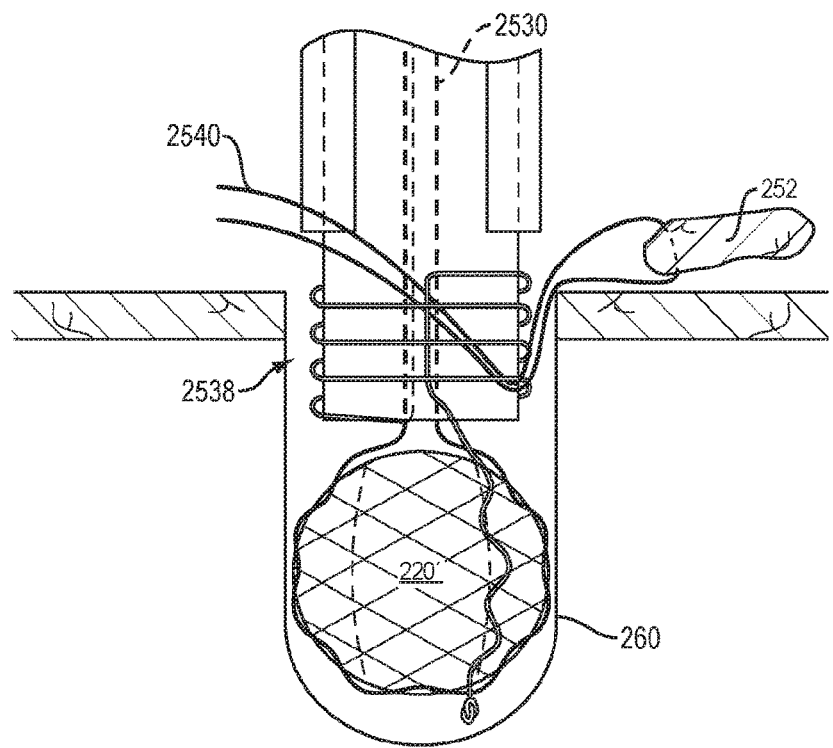
Figure 28F:
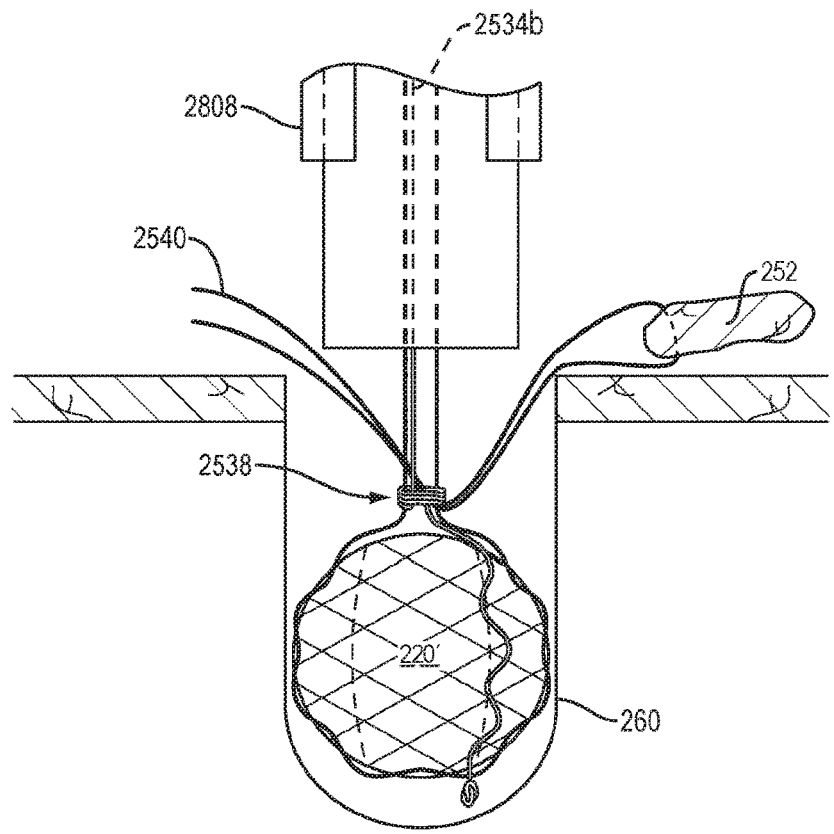
Figure 29:
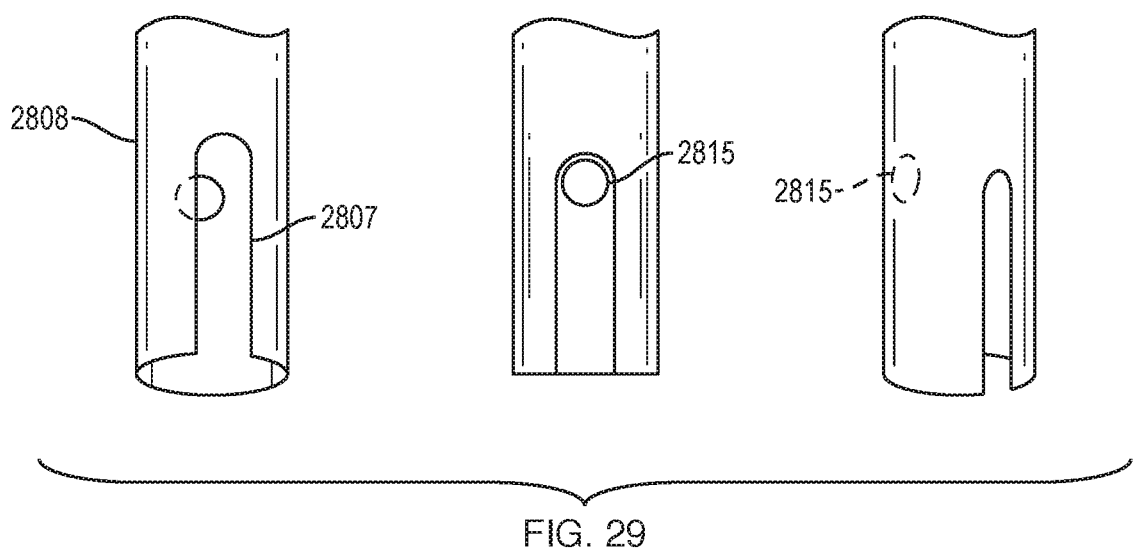
FIG. 29 shows an alternative embodiment of a tube of an insertion instrument.

A method of tissue repair is represented in FIG. 28A-28F including system 2800. The method may therefore start with coupling a repair suture 2540 to tissue 252 and threading repair suture 2540 through a nail knot wrapped around an insertion instrument shaft, which may be an outer shaft 2808 that houses an anchor 220. Threading may include extending the repair suture 2540 through a suture snare 2870, and the suture snare 2870 may extend through an aperture of an insertion instrument tube 2808 and may extend through at least one wrap of a nail knot 2538 such that drawing on the snare 2870 threads the repair suture 2540 though at least one wrap of a nail knot 2538. Drawing on the snare 2870 may further thread the repair suture through and along a lumen of the insertion instrument and couple the repair suture 2540 to a tensioning means associated with the insertion instrument. Repair suture 2540 may be drawn through the nail knot 2538 while the insertion instrument is placed within a prepared bone tunnel, or before the insertion instrument is disposed therein as shown in FIG. 28B. The insertion instrument aperture may include an elongate slot 2807 on the outer tube 2808 of the instrument, the outer tube 2808 housing a soft anchor operatively coupled to the nail knot 2538. Outer tube 2808 may be placed within bone tunnel 260 and withdrawn as to expell the anchor 220 from the instrument, the elongate slot 2807 configured to allow release of outer tube from repair suture 2540 extending therethough (FIG. 28D). Nail knot 2538 may be coupled to anchor 220. Nail knot 2538 may include a first limb 2534*a* that extends through a portion of anchor 220 and is tied to or operatively coupled to a distal end of anchor 220, forming a knot 2839. Repair suture 2540 may also extend through a lumen of inner tube 2814, and thereby extend through an elongate slot similar to inner tube 2515. Tension on ends of repair suture 2540 may then be applied to approximate the tissue 252 towards the bone 260 (FIG. 28CA). Tension on ends of expansion suture 2530 (only shown in FIG. 28E) may then be applied to radially expand anchor 220 and anchor the system 2800 within the bone tunnel, as shown in FIG. 28E. Expansion suture ends 2530 may be operably coupled to a control in insertion instrument handle (not shown) that may control the applied tension. Expansion suture ends may be incorporated into the a handle of the system that may be a rotational handle that may initially retract the expansion suture 2530 at high speed then step down to a lower "gear" with higher mechanical advantage for the final anchor expansion. This "step down" could be based on tension or suture length. An integral knot pusher (not shown) may slide distally and push nail knot 2538 from inner tube 2515 once anchor 220' is deployed, or simultaneously during deployment. Tension on proximal limb 2534*b* of nail knot 2538 while actuation of knot pusher 2780 may tighten nail knot 2538 and cinch the plurality of wraps 2536 around expansion suture 2530 and repair suture 2540 (FIG. 28F). An integral knife (not shown) to the instrument may be incorporated into the delivery system such that the expansion suture 2530 or expansion and repair sutures 2540 would be cut upon reaching proper expansion tension. After deployment, the Nail knot 2538 may still reside at or below the bone surface, as shown in FIG. 28F.

An alternative embodiment, not shown, may form the nail knot with the expansion suture 2530 member, such that a portion of expansion suture 2530 may form the plurality of wraps 2536 around a tube or shaft of the insertion instrument. Expansion suture 2530 may be provided operatively coupled to the anchor 220 to deploy the anchor via tension on the expansion suture limbs 2532. At least one of the expansion suture limbs may also form a plurality of wraps around a portion of the insertion instrument. This plurality of wraps may be wrapped around an outer circumferential surface of a tube or shaft of the insertion instrument, similar to that shown in FIG. 26A or FIG. 28A. Both limbs of expansion suture (2532) may preferably also extend along the plurality of wraps 2536 such that tightening of the plurality of wraps, locks around both expansion suture limbs 2532, similar to the construct disclosed in FIG. 21 for example. More preferably, both limbs 2532 extend from a distally disposed wrap to a proximal wrap of the plurality of wraps 2536. Tension on the expansion suture limbs 2532 therefore may simultaneously deploy the anchor 220 while tightening the wraps 2536 around expansion suture limbs 2532. Alternatively, with tension on the expansion suture limbs 2532 with the wraps remaining around the insertion instrument, the inventors envision some partial deployment of the anchor 220 before locking around the limbs 2532, and therefore some sequential deployment and then locking may be an option. Limbs 2532 may extend proximally along push tube inner lumen, while the plurality of wraps 2536 wrap may around an external circumference of the push tube. Furthermore distal end of the push tube 2514 may also comprises at least one slot such as a first slot 2515*a* and second slot 2515*b* to allow passage of expansion suture limb 2532 between the internal lumen of an inserter tube and external surface to form the wraps. A repair suture may also extend along the plurality of wraps of the expansion suture, in a similar fashion as shown in FIG. 27A, and tension on the expansion suture limbs 2532 may also lock the repair suture extending therealong.

In a further alternative embodiment, Nail knot 2538 may be formed by expansion suture 2530 at an anchor distal end (not shown). This embodiment is not specifically shown; however, reference to FIGS. 2A, 10 and FIG. 26A represent portions of this embodiment. As such, expansion suture 2530 may extend along and operatively couple to anchor 220, to selectively deploy anchor 220 as described herein. Expansion suture 2530 may form a plurality of loops along the anchor. A length of expansion suture 2530 at distal end of anchor 220, may form a plurality of wraps defining a longitudinal axis that may be orthogonal to the longitudinal axis of the anchor 220 and bone tunnel, and may be disposed along a distal-most end of anchor 220. Referencing FIGS. 2A and 2B, this embodiment may include a nail knot 2538 in a similar location to longitudinal passage 232 along the expansion suture and relative to the suture anchor 220. A loading tube or suture passer may extend along the plurality of wraps of the nail knot 2538 to maintain the plurality of wraps open to draw the repair suture 250 therethrough. The plurality of wraps may wrap around the loading tube, in a similar manner to insertion instrument in FIG. 26A. Loading tube may include slots similar to slots 2515a and 2515b in FIG. 26A to manage ends of the nail knot as it enters and exits the nail knot. Alternatively, no slots may be required and the suture and plurality of wraps may remain on an external surface of the loading tube. Expansion suture 2538 may also include a sliding knot similar to knot 238 adjacent a proximal end of anchor 220. Expansion suture may include external barbs along a portion that extends through anchor 220, to allow sliding through the anchor 220 in a first, deploying direction and resist sliding in the opposite direction that may allow the anchor to relax and elongate. Alternatively, similar to embodiment disclosed in FIG. 5-7, a separate locking suture may also operatively coupled to anchor 220 to knotlessly lock system. Locking suture may include a knot 238 or longitudinal passage to knotlessly lock the system. A method of knotlessly repairing tissue may therefore include drawing or pushing the repair suture 2540 through the nail knot 2538 before inserting the anchor 220 into a bone tunnel. The anchor 220 may then be inserted into a bone tunnel and tension on the expansion suture 2538 may simultaneously deploy the anchor and lock the repair suture in place. Having the nail knot at the distal end of anchor may reduce complexity of anchor deployment and the insertion device.

Figure 30A:
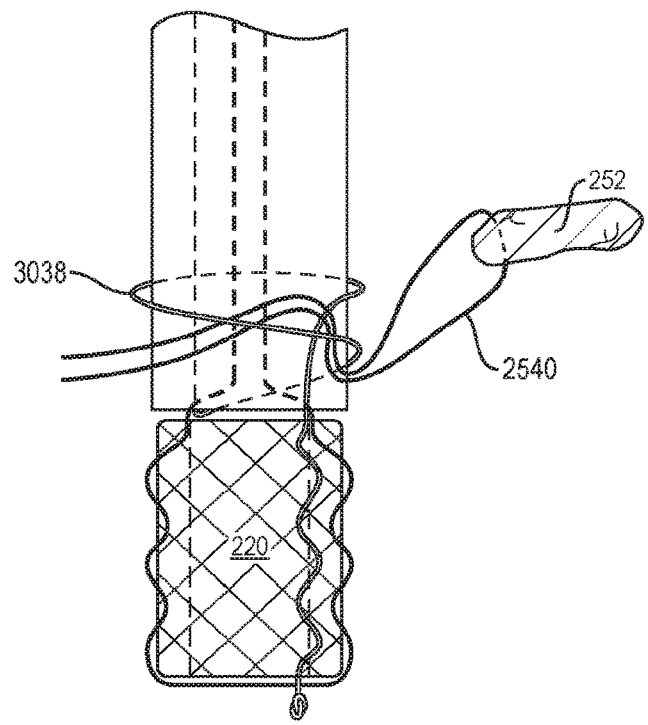
FIGS. 30A and 30B show alternative embodiments of a strangling knot arranged around an insertion instrument distal end, for knotlessly coupling soft tissue to a knotless soft system, in accordance with this disclosure.
Figure 30B:
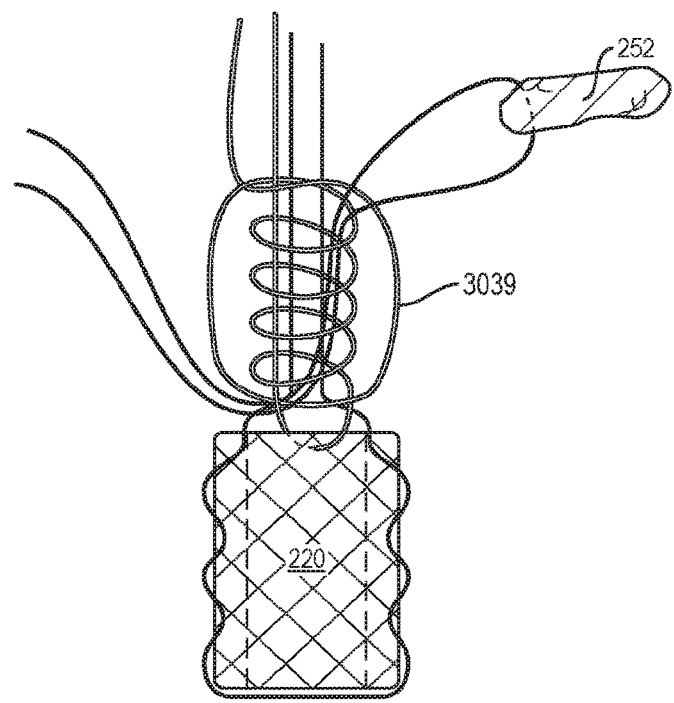
Figure 31:
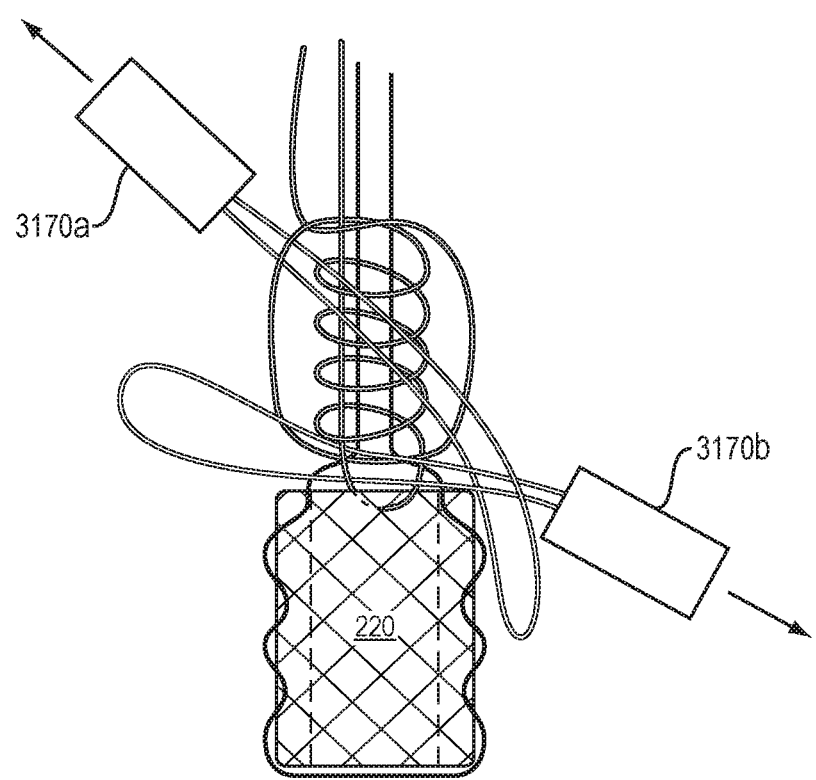
FIG. 31 shows an alternative embodiment of a series of snares associated with a knotless soft system, in accordance with this disclosure.

The Nail Knot in alternate embodiments may include alternative knots that are provided wrapped around an external surface of insertion instrument, shown in FIGS. 30A, 30B and 31. FIG. 30A shows a figure-of-eight knot 3038. FIG. 30B shows an improved Clinch Knot 3039 being attached to the anchor 220. Additionally, a knot such as the 'Modified' Figure-of-eight knot, as shown in FIG. 30, may require the use of a dual suture passer (3170). The passer 3170 includes a first looped suture passer 3170a that shuttles the free limb of repair suture(s) 2540 through the opening on the second suture passer 3170b, and the second suture passer shuttles the free limb of repair suture(s) 2540 through the second portion of the pre-configured knot weave 3038. Both of these suture passers may be coupled to the inserter such that they can be pulled in order. In a further embodiment, the second suture passer is hidden beneath the first suture passer such that the second can only be pulled after the first is pulled.

Figure 32A:
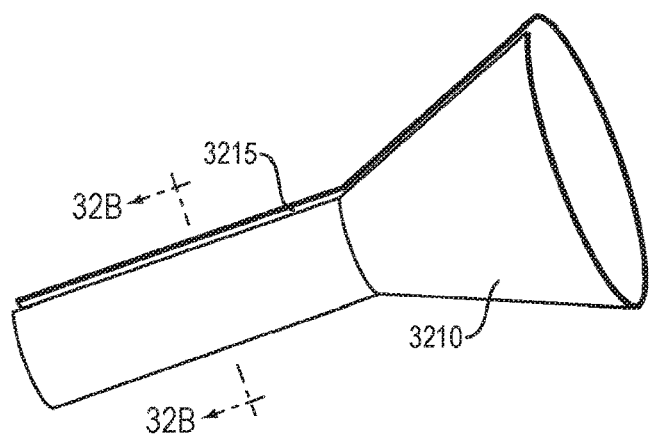
FIG. 32A-32C show a tissue repair system including a suture funnel in accordance with this disclosure.
Figure 32B:
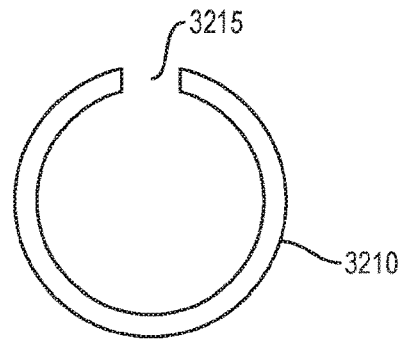
Figure 32C:
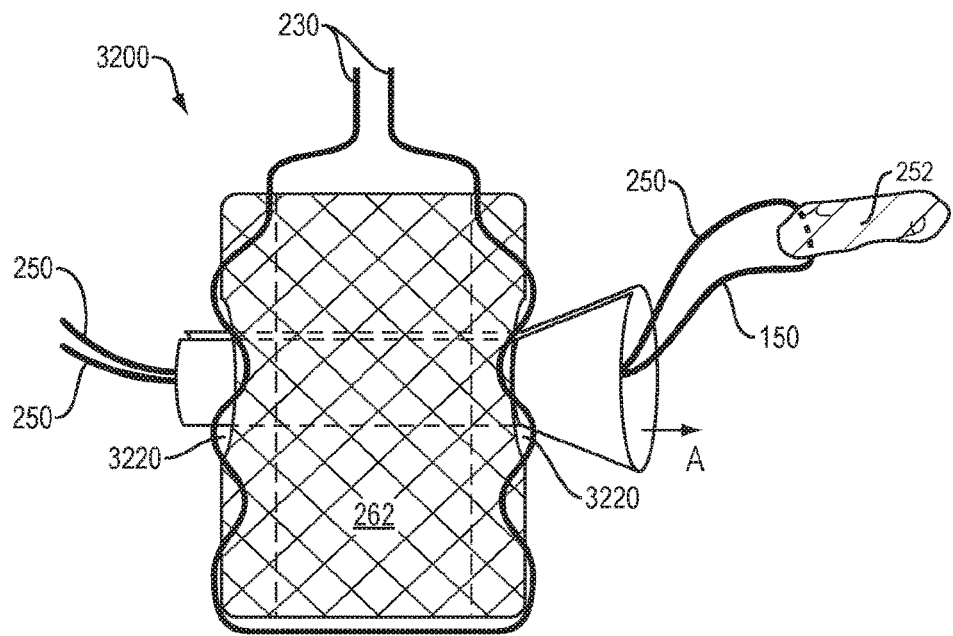

FIGS. 32A, 32B and 32C show a tissue repair system 3200 including a suture funnel 3210. This may be preferable for a system wherein the repair suture 250 simply extends across and through the body of suture anchor 220. Repair suture 250 may extend perpendicular to the longitudinal axis of the anchor 220. The repair suture 250 may be knotlessly locked as the anchor 220 deploys and the inter-braid friction and repair suture torsional path is sufficient to lock the repair suture in place. The inventors have found that a wired style suture snare tends to fray the braids or material of a soft anchor body and therefore is not a preferable means of threading a repair suture through the body of a soft body anchor 220. A funnel 3210 may therefore be provided with the system, extending across and through the anchor. Funnel 3210 may extend between braids, or an opening may be prepared using a dilation or expanding tool, or by cutting some braids for example. Funnel 3210 includes an elongate opening 3215 that extends the entire length of funnel 3210, shown best in FIGS. 32A and 32B. FIG. 32C illustrates a part of a tissue repair system 3200. An expansion member 230 may be provided, operatively coupled to anchor 220 and may extend along anchor 220, along a plane that is circumferentially spaced from the funnel 3210 so that the funnel 3210 does not interfere with expansion member as the expansion member extends through the anchor 220 or as the funnel is removed. Openings 3220 through anchor 220 are shown directly opposite each other. To increase the tortuous path, openings may be axially offset, such that funnel 3210 is angled non-perpendicularly to anchor longitudinal axis. Repair sutures 250 may be pushed through funnel using a small diameter rod (not shown). The funnel 3210 may then be removed in direction of arrow A. Slot 3215 allows the repair suture to release from funnel 3210. Funnel 3210 may be sufficiently rigid to withstand deformation or collapse due to anchor 220 and remain open to allow passage of repair suture 250 therethrough. Insertion instrument may include slots or holes similar to slots 2515 for example configured to allow ends of funnel to extend laterally therethough. Funnel 3210 is preferable removed before inserting anchor 220 into a bone tunnel.

While this disclosure has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

We claim:

1. A tissue repair assembly comprising:
   a soft anchor having a proximal end, a distal end, and a longitudinal axis extending therebetween;
   an expansion suture coupled to the soft anchor, a first end and a second end of the expansion suture exit the soft anchor adjacent to the proximal end of the soft anchor;
   a repair suture separately formed from the expansion suture for coupling a tissue with the soft anchor;
   a locking suture separately formed from both the expansion suture and repair suture, the locking suture coupled to the soft anchor and includes a pre-formed knot and wherein a portion of the pre-formed knot is configured to receive the repair suture and expansion suture therethrough;
   wherein tensioning on at least one of the first and second ends of the expansion suture causes the soft anchor to change to a deployed configuration; and wherein tension on the locking suture is configured to selectively tighten the pre-formed knot and lock the soft anchor in the deployed configuration.

2. The tissue repair assembly of claim 1 wherein the locking suture is interwoven with the soft anchor and the pre-formed knot is adjacent to the soft anchor proximal end.

3. The tissue repair assembly of claim 1 further comprising an insertion instrument for placing the soft anchor within a bone hole, and wherein the pre-formed knot defines a nail knot having a plurality of loops wrapped around the insertion instrument.

4. The tissue repair assembly of claim 3 wherein the insertion instrument has a first slot at a distal end of the insertion instrument and wherein the locking suture has a first tail that extends through the first slot and distally along a portion of the insertion instrument.

5. The tissue repair assembly of claim 3 wherein the expansion suture extends from the soft anchor and along the nail knot.

6. The tissue repair system of claim 4 wherein the first tail is operatively coupled to the soft anchor.

7. The tissue repair system of claim 4, wherein the insertion instrument comprises a second slot, circumferentially spaced from the first slot, and wherein the locking suture further comprises a second tail extending through the second opening and then proximally along the insertion instrument.

8. The tissue repair assembly of claim 1 wherein the pre-formed knot is a nail knot comprising a plurality of wraps and wherein at least one of the plurality of wraps is stitched to the soft anchor.

9. The tissue repair assembly of claim 1 further comprising a suture threader extending through the pre-formed knot, for coupling to the repair suture and drawing the repair suture through the pre-formed knot.

10. The tissue repair assembly of claim 3 further comprising a knot pusher integral with the insertion instrument for pushing the pre-formed knot from the insertion instrument.

11. A tissue repair assembly comprising:
- a soft anchor having a proximal end, a distal end, and a longitudinal axis extending therebetween;
- an expansion suture coupled to the soft anchor, a first end and a second end of the expansion suture extends proximally from the soft anchor proximal end;
- a repair suture separately formed from the expansion suture for coupling a tissue with the soft anchor;
- a locking suture separately formed from both the expansion suture and repair suture, the locking suture coupled to the soft anchor and includes a pre-formed knot disposed at a proximal end of the soft anchor;
- wherein tensioning on at least one of the first and second ends of the expansion suture is configured to deploy the soft anchor; and wherein tensioning an end of the locking suture is configured to tighten the pre-formed knot around at least one of the expansion suture and repair suture.

12. The tissue repair assembly of claim 11 wherein the locking suture is interwoven with the soft anchor and the pre-formed knot is external to the soft anchor proximal end.

13. The tissue repair assembly of claim 11 further comprising an insertion instrument for placing the soft anchor within a bone hole, and wherein the pre-formed knot has a plurality of loops wrapped around an outer surface of a tube of the insertion instrument.

14. The tissue repair assembly of claim 13 wherein the insertion instrument tube has a first longitudinal slot and wherein the locking suture has a first tail that extends through the first slot and distally into the soft anchor, to couple the locking suture to the soft anchor.

15. The tissue repair assembly of claim 11 wherein the pre-formed knot is a nail knot comprising a plurality of wraps and wherein at least one of the plurality of wraps is stitched to the soft anchor.

16. The tissue repair assembly of claim 11 further comprising a suture threader extending through the pre-formed knot, for coupling to the repair suture and drawing the repair suture through the pre-formed knot.

17. The tissue repair assembly of claim 13 further comprising a knot pusher integral with the insertion instrument for pushing the pre-formed knot from the insertion instrument.

18. A tissue repair assembly comprising:
- a soft anchor having a proximal end, a distal end, and a longitudinal axis extending therebetween;
- an expansion suture coupled to the soft anchor, a first end and a second end of the expansion suture extends proximally from the soft anchor proximal end;
- a repair suture separately formed from the expansion suture for coupling a tissue with the soft anchor;
- a locking suture separately formed from both the expansion suture and repair suture, the locking suture coupled to the soft anchor and includes a pre-formed knot at a proximal end of the soft anchor, the preformed knot configured to receive the repair suture, after the repair suture has been coupled to tissue;
- wherein tensioning on at least one of the first and second ends of the expansion suture is configured to deploy the soft anchor; and wherein tensioning an end of the locking suture is configured to tighten the pre-formed knot around repair suture and lock the tissue in place.

19. The tissue repair assembly of claim 18 wherein the pre-formed knot is external to the soft anchor proximal end.

20. The tissue repair assembly of claim 18 further comprising an insertion instrument for placing the soft anchor within a bone hole, and wherein the pre-formed knot has a plurality of loops wrapped around an outer surface of a tube distal end of the insertion instrument.

* * * * *